US012698357B2

(12) United States Patent
Lim

(10) Patent No.: US 12,698,357 B2
(45) Date of Patent: Aug. 4, 2026

(54) HIGH TEMPERATURE BENZOXAZINE RESINS, METHODS, AND USES THEREOF

(71) Applicant: KANEKA CORPORATION, Osaka (JP)

(72) Inventor: Young Hoon Lim, Pasadena, TX (US)

(73) Assignee: KANEKA CORPORATION, Osaka (JP)

( * ) Notice: Subject to any disclaimer, the term of this patent is extended or adjusted under 35 U.S.C. 154(b) by 710 days.

(21) Appl. No.: 18/026,997

(22) PCT Filed: Sep. 30, 2021

(86) PCT No.: PCT/IB2021/022220
§ 371 (c)(1),
(2) Date: Mar. 17, 2023

(87) PCT Pub. No.: WO2022/069948
PCT Pub. Date: Apr. 7, 2022

(65) Prior Publication Data

US 2023/0365730 A1 Nov. 16, 2023

Related U.S. Application Data

(60) Provisional application No. 63/107,828, filed on Oct. 30, 2020, provisional application No. 63/085,875, filed on Sep. 30, 2020.

(51) Int. Cl.

| | |
|---|---|
| *C08G 14/06* | (2006.01) |
| *C07D 413/14* | (2006.01) |
| *C08F 222/40* | (2006.01) |
| *C08F 234/02* | (2006.01) |
| *C08J 5/24* | (2006.01) |

(52) U.S. Cl.
CPC ........ *C08F 222/406* (2020.02); *C07D 413/14* (2013.01); *C08F 234/02* (2013.01); *C08J 5/24* (2013.01); *C08F 2810/20* (2013.01)

(58) Field of Classification Search
CPC ...................................................... C08G 14/06
See application file for complete search history.

(56) References Cited

U.S. PATENT DOCUMENTS

| | | | | |
|---|---|---|---|---|
| 5,973,144 A | 10/1999 | Ishida | | |
| 6,482,946 B1 * | 11/2002 | Dettloff | C07D 413/04 528/145 |
| 2017/0008994 A1 * | 1/2017 | Wang | C09D 161/34 |

FOREIGN PATENT DOCUMENTS

| | | |
|---|---|---|
| CN | 109679048 A | 4/2019 |
| JP | 2006265433 A | 10/2006 |
| WO | 2019/044977 A1 | 3/2019 |

OTHER PUBLICATIONS

Jin, Lin, et al.; Bis(benzoxazine-maleimide)s as a novel class of high performance resin: Synthesis and properties; European Polymer Journal; 46(2), pp. 354-363; Sep. 26, 2009; ISSN 0014-3057 (10 pages).
Zhang, Jing, et al.; Nitrile Functionalized Benzoxazine/Bismaleimide Blends and Their Glass Cloth Reinforced Laminates; Journal of Applied Polymer Science; 131(22), pp. 41072/1-41072/7; 2014; ISSN 0021-8995 (7 pages).
Brunovska, Zdenka, et al.; Thermal properties of phthalonitrile functional polybenzoxazines; Thermochimica Acta; 357-358, pp. 195-203; 2000; IISN 0040-6031 (9 pages).
International Search Report issued in corresponding International Application No. PCT/IB2021/022220, dated Dec. 21, 2021 (4 pages).
Written Opinion issued in corresponding International Application No. PCT/IB2021/022220, dated Dec. 21, 2021 (5 pages).
Notification of Reasons for Refusal issued in corresponding Japanese Patent Application No. 2023-519685, mailed May 7, 2024.

* cited by examiner

*Primary Examiner* — Michael J Feely
(74) *Attorney, Agent, or Firm* — Osha Bergman Watanabe & Burton LLP

(57) ABSTRACT

A benzoxazine resin composition is provided. The benzoxazine resin composition includes a benzoxazine resin that is a reaction product of an amine, a phenol, and an aldehyde. Either the amine is a diamine or the phenol is a bisphenol, and the benzoxazine resin has at least one nitrogen-containing crosslinking functional group or pyrocitric functional group. A method of preparing a benzoxazine resin composition is also provided. The method includes reacting an amine, a phenol, and an aldehyde at a temperature of above 60° C., for 1 h to 5 days to form a benzoxazine resin. The benzoxazine resin has at least one nitrogen-containing crosslinking functional group or pyrocitric functional group, and either the amine is a diamine or the phenol is a bisphenol. Also provided is a cured resin made from the benzoxazine resin composition.

16 Claims, 42 Drawing Sheets

1 RODA + 2 HPMI + 4 $CH_2O$ Aldehyde

RODA-Bis(MI-BZ)

1 BAPP + 2 HPMI + 4 $CH_2O$ Aldehyde

BAPP-Bis(MI-BZ)

1 p-TPE-Q + 2 HPMI + 4 $CH_2O$ Aldehyde pTPEQ-Bis(MI-BZ)

RODA-Bis(MI-BZ)

(c)

BAPP-Bis(Cl-BZ)

pTPEQ-Bis(CN-BZ)

DDS-Bis(CN-BZ)

HIGH TEMPERATURE BENZOXAZINE RESINS, METHODS, AND USES THEREOF

BACKGROUND

Polybenzoxazine resins exhibit high thermal stability, high chemical resistance, low water absorption, near-zero shrinkage and expansion upon thermal curing, high flame retardance with high char yield, and outstanding mechanical properties as compared to thermoset composites of epoxy, phenolics, and bismaleimide. Besides rich molecular design flexibility, the benzoxazine monomer itself is preferable for processing due to its low melt-viscosity, effective polymerization without harsh catalysts, and no formation of byproducts during polymerization. With the above characteristics, benzoxazine resins are promising as matrices for high performance thermoset composites in the fields of aerospace, electronics, adhesives, coatings, etc.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a benzoxazine resin composition comprising a benzoxazine resin that is a reaction product of an amine, a phenol, and an aldehyde. Either the amine is a diamine or the phenol is a bisphenol, and the benzoxazine resin has at least one nitrogen-containing crosslinking functional group or pyrocitric functional group.

In another aspect, embodiments disclosed herein relate to a method of preparing a benzoxazine resin composition, comprising reacting an amine, a phenol, and an aldehyde to form a benzoxazine resin, wherein the benzoxazine resin has at least one nitrogen-containing crosslinking functional group or pyrocitric functional group, and wherein either the amine is a diamine or the phenol is a bisphenol, at a temperature of above 60° C., for 1 h to 5 days.

In yet another aspect, embodiments disclosed herein relate to a cured resin comprising a cured benzoxazine resin. The benzoxazine resin, prior to curing, comprises a reaction product of an amine, a phenol, and an aldehyde. The benzoxazine resin has at least one nitrogen-containing crosslinking functional group or pyrocitric functional group, and either the amine is a diamine or the phenol is a bisphenol.

Other aspects and advantages of the claimed subject matter will be apparent from the following description and the appended claims.

DETAILED DESCRIPTION

Figure 1:
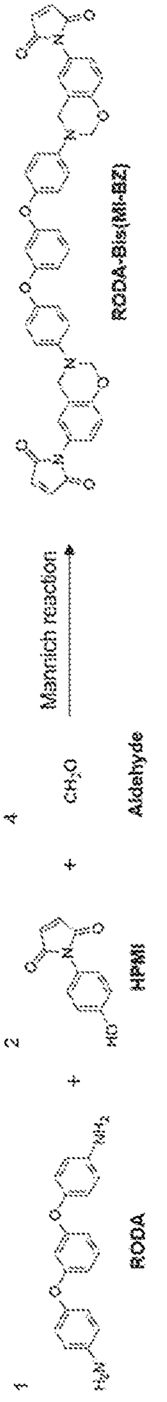
FIG. 1 shows a reaction scheme for the formation of RODA-Bis(MI-BZ) in accordance with embodiments of the present disclosure.

In one aspect, embodiments disclosed herein relate to benzoxazine resins, compositions thereof, composites thereof, and methods thereof. For example, embodiments are directed to a benzoxazine resin comprised of at least one benzoxazine ring and including at least one nitrogen-containing crosslinking functional group (meaning a nitrogen containing functional group with ability to crosslink), or functional group derived from a diacid or an anhydride, or furan functional group, or combinations of these groups. In another aspect, a benzoxazine resin may include a maleimide, a pyrocitric or a nitrile functional group, or a furan functional group. Pyrocitric functional groups may include nitrogen-containing functional groups (such as imide or amide derivatives of a pyrocitric acid), but it is also envisioned that embodiments may include other derivatives of a pyrocitric acid, a diacid, or an anhydride, as well. Embodiments are also directed to curable (and cured) compositions containing one or more components, including a benzoxazine resin; composite materials such as prepregs, including a benzoxazine resin; and methods of blending and curing a benzoxazine resin.

In particular, embodiments disclosed herein relate to a benzoxazine resin comprised of at least one benzoxazine ring and at least one nitrogen-containing crosslinking functional group or functional group derived from a diacid or an anhydride. The inclusion of benzoxazine ring(s) and at least one nitrogen-containing crosslinking functional group (such as at least one of a maleimide functional group, a pyrocitric functional group, and a nitrile functional group) or at least one functional group derived from a diacid or an anhydride (such as at least one pyrocitric functional group) in the resin advantageously result in a high crosslink density in a cured composite of the resin. In particular embodiments, the benzoxazine resin may be composed of two benzoxazine rings and at least one of a maleimide functional group, a pyrocitric functional group, and a nitrile functional group. In more particular embodiments, the benzoxazine resin may be composed of two benzoxazine rings and two (or more) maleimide functional groups, two (or more) pyrocitric functional groups, or two (or more) nitrile functional groups. Moreover, the resin may exhibit a low complex viscosity at low temperatures, allowing for facile processing. Thus, the resin of the present disclosure may overcome challenges present when using conventional thermosetting resins while also achieving superior mechanical properties. The benzoxazine resin may possess a temperature range in which it may be molded prior to reaching the elevated crosslinking temperature, at which point the crosslinking of the functional unit may be triggered. For example, while a benzoxazine resin conventionally softens or re-melts upon exposure to temperatures above the melt-processing temperatures for the given resin, making such resin unsuitable for articles in high temperature applications, the benzoxazine resin of the present disclosure may be crosslinked upon forming the article, thus preventing the softening or re-melting that would conventionally occur for the resin.

In general, there are two possible synthetic methods to form a benzoxazine resin containing two benzoxazine moieties: a first reaction employing bisphenol, amine, and paraformaldehyde as shown in reaction scheme (I) below, and a second reaction employing diamine, phenol, and paraformaldehyde as shown in reaction scheme (II) below.

(I)

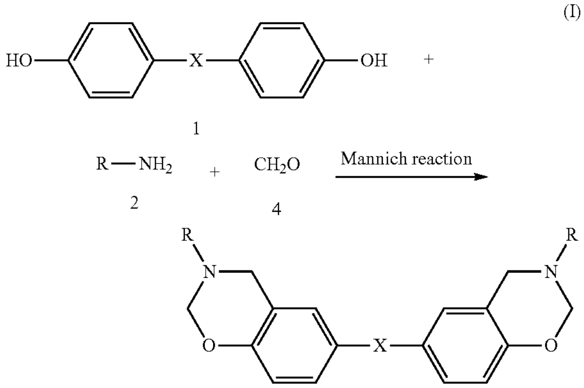

1 2 4

(II)

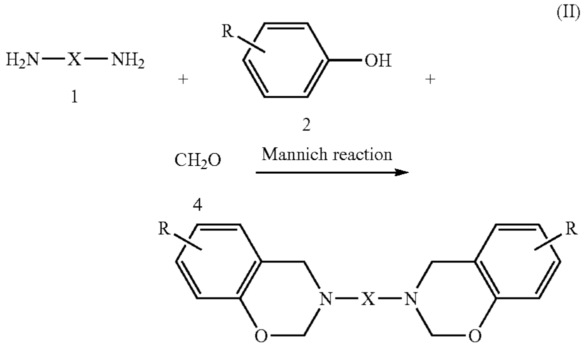

1 2 4

As mentioned above, embodiments of the present application are directed to a benzoxazine resin containing at least one benzoxazine ring and at least one nitrogen-containing crosslinking functional group (such as at least one of a maleimide functional group, a pyrocitric functional group or a nitrile functional group). Thus, in reaction schemes (I) and (II) shown above, the R group may be a nitrogen-containing crosslinking functional group, which may include, but is not limited to, a maleimide functional group, a pyrocitric functional group, and/or a nitrile functional group. With two benzoxazine groups and two nitrogen-containing crosslinking functional groups per molecule that may be maleimide functional groups, pyrocitric functional groups, and/or nitrile functional groups, each molecule may have four crosslinking sites, which upon crosslinking result in a cured thermoset having a high crosslinking density.

In one or more embodiments, a pyrocitric functional group includes derivatives of citraconic, itaconic, or mesaconic acid. In one or more embodiments, a pyrocitric functional group includes derivatives of citraconic, itaconic, or mesaconic anhydride. In some embodiments, derivatives of citraconic acid or citraconic anhydride may include citraconic imides. In some embodiments, derivatives of itaconic acid or itaconic anhydride may include an itaconic imide. In some embodiments, derivatives of mesaconic acid or mesaconic anhydride may include a mesaconic imide. As such, nitrogen-containing pyrocitric functional groups in accordance with one or more embodiments of the present disclosure may include citraconic, itaconic, and/or mesaconic imides. However, it is also envisioned that the pyrocitric functional group may also include amides or esters of a pyrocitric acid or anhydride.

In one or more embodiments, a nitrile functional group (—C≡N) is a cyano functional group. Three nitrile groups may react, by thermal activation, to form a triazine structure. Thus, thermal activation of nitrile functional group-containing benzoxazine resins may result in high crosslinking density in a cured composite due to, in part, this triazine formation.

In one or more embodiments, the benzoxazine resin may be synthesized by the reaction of a diamine, phenolic compound(s) containing a maleimide functional group, a pyrocitric functional group, or a nitrile functional group, and aldehyde (such as formaldehyde or paraformaldehyde). As previously described, examples of suitable pyrocitric functional groups include but are not limited to citraconic imide, itaconic imide, and mesaconic imide. The diamines may contain an ether linkage, including but not limited to an alkyl ether or aromatic ether, which in some embodiments may also include a pendant alkyl or phenyl group, or may have another type of heteroatom linkage. In another embodiment, the diamines may contain a sulfide linkage, including but not limited to an alkyl sulfide or aromatic sulfide, which in some embodiments may also include a pendant alkyl or phenyl group, or may have another type of heteroatom linkage. In some embodiments, the diamines may contain a sulfone linkage, including but not limited to an alkyl sulfone or aromatic sulfone, which in some embodiments may also include a pendant alkyl or phenyl group, or may have another type of heteroatom linkage. In some embodiments, the diamine may have an asymmetric structure. In some embodiments, the diamine may contain one or more maleimide functional groups, one or more pyrocitric functional groups, and/or one more nitrile functional groups, instead of or in addition to the phenolic compound(s).

In one or more embodiments, the phenol is a hydroxyl phenyl compound containing at least one nitrogen-containing crosslinking functional group. In one or more embodiments, the phenol is a hydroxyl phenyl compound containing at least one maleimide functional group. Examples of suitable phenols include but are not limited to N-(2-hydroxyphenyl)maleimide, N-(3-hydroxyphenyl)maleimide, N-(4-hydroxyphenyl)maleimide, N-(4-carboxy-3-hydroxyphenyl)maleimide, N-(4-carboxy-2-hydroxyphenyl)maleimide, N-(3-carboxy-2-hydroxyphenyl)maleimide, N-(3-carboxy-4-hydroxyphenyl)maleimide, N-(2-carboxy-3-hydroxyphenyl)maleimide, and N-(2-carboxy-4-hydroxyphenyl)maleimide.

In some embodiments, the phenol is a hydroxyl phenyl compound containing at least one pyrocitric functional group selected from a citraconic imide functional group, itaconic imide functional group, and a mesaconic imide functional group. Examples of suitable phenols include but are not limited to N-(2-hydroxyphenyl)citraconic imide, N-(3-hydroxyphenyl)citraconic imide, N-(4-hydroxyphenyl)citraconic imide, N-(4-carboxy-3-hydroxyphenyl)citraconic imide, N-(4-carboxy-2-hydroxyphenyl)citraconic imide, N-(3-carboxy-2-hydroxyphenyl)citraconic imide, N-(3-carboxy-4-hydroxyphenyl)citraconic imide, N-(2-carboxy-3-hydroxyphenyl)citraconic imide, N-(2-carboxy-4-hydroxyphenyl)citraconic imide, N-(2-hydroxyphenyl) itaconic imide, N-(3-hydroxyphenyl)itaconic imide, N-(4-hydroxyphenyl)itaconic imide, N-(4-carboxy-3-hydroxyphenyl)itaconic imide, N-(4-carboxy-2- hydroxyphenyl)itaconic imide, N-(3-carboxy-2-hydroxyphenyl)itaconic imide, N-(3-carboxy-4-hydroxyphenyl)itaconic imide, N-(2-carboxy-3-hydroxyphenyl)itaconic imide, N-(2-carboxy-4-hydroxyphenyl)itaconic imide, N-(3-hydroxyphenyl) mesaconic imide, N-(4-hydroxyphenyl)mesaconic imide, N-(4-carboxy-3-hydroxyphenyl)mesaconic imide, N-(4-carboxy-2-hydroxyphenyl)mesaconic imide, N-(3-carboxy-2-hydroxyphenyl)mesaconic imide, N-(3-carboxy-4-hydroxyphenyl)mesaconic imide, N-(2-carboxy-3-hydroxyphenyl) mesaconic imide, N-(2-carboxy-4-hydroxyphenyl) mesaconic imide, or combinations thereof.

In one or more embodiments, the phenol is a hydroxyl phenyl compound containing at least one nitrile functional group. Examples of suitable phenols include but are not limited to 2-hydroxybenzonitrile (also known as 2-cyanophenol), 3-hydroxybenzonitrile (also known as 3-cyanophenol), 4-hydroxybenzonitrile (also known as 4-cyanophenol), 2-hydroxy-4-methoxybenzonitrile, 2-hydroxyphenylacetonitrile, 3-hydroxyphenylacetonitrile, 4-hydroxyphenylacetonitrile, 2-hydroxyphthalonitrile, 3-hydroxyphthalonitrile, 4-hydroxyphthalonitrile, 3,5-dimethyl-4-hydroxybenzonitrile, hydroxy(4-hydroxyphenyl)acetonitrile, 2,4,5-trichloro-6-hydroxyisophthalonitrile, 3-bromo-2-hydroxybenzonitrile, 5-bromo-2-hydroxybenzonitrile, 2-chloro-4-hydroxybenzonitrile, 2,6-difluoro-4-hydroxybenzonitrile, 2-chloro-6-fluoro-3-hydroxybenzonitrile, 3-bromo-5-cyclohexyl-2-hydroxybenzonitrile, 3-chloro-5-cyclohexyl-2-hydroxybenzotnitrile, 6-cyano-2-naphthol, 4-hydroxy-3-nitrobenzonitrile, or combinations thereof.

When reacting with diamine, the previously described phenols may be present in a molar ratio ranging from 1:1 to 2:1, relative to the diamine. For example, in one or more embodiments, the molar ratio of phenol to diamine may have a lower limit of any of 1:1, 1.2:1, or 1.4:1, to an upper limit of any of 1.6:1, 1.8:1, or 2:1, where any lower limit can be used in combination with any mathematically-compatible upper limit. In one or more embodiments, a single species of phenol may be used or a combination may be used. When using a combination of phenols, it is envisioned that a portion (but not all) of the phenol used may have at least one maleimide functional group, at least one pyrocitric functional group, or at least one nitrile group. In such embodiments, the presence of a quantity of phenolic compounds without maleimide groups, pyrocitric groups, or nitrile groups, in combination with phenolic compounds having maleimide groups, pyrocitric groups, or nitrile groups may, result in a resin having fewer than four crosslinking sites. Thus, an amount of phenol without maleimide functional groups, pyrocitric functional groups, or nitrile functional groups may be used in some embodiments to achieve varied properties in the benzoxazine resin or cured thermoset, including a reduced crosslinking density.

In one or more embodiments, the diamine is an alkyl or aromatic diamine, including aliphatic or aromatic ether diamines, which may optionally contain an alkyl or phenyl pendant group(s); aliphatic or aromatic sulfide diamines, which may optionally contain an alkyl or phenyl pendant groups; aliphatic or aromatic sulfone diamines, which may optionally contain an alkyl or phenyl pendant group(s); a silicone-based diamine; and/or polyetheramines. Examples of suitable diamines include but are not limited to 1,3-bis(4-aminophenoxy)benzene (RODA), 2,2-bis(4-aminophenoxyphenyl)propane (BAPP), 1,4-bis(4-aminophenoxy) benzene (TPE-Q), 4-[4-(4-aminophenoxy)-3-phenylphenoxy]aniline (p-TPE-Q), 1,4-bis(3-aminophenoxy)benzene, 4-[4-[4-(4-aminophenoxy)phenoxy]phenoxy]aniline, bis[4-(3-aminophenoxy)phenyl] sulfone (BAPS-m), bis[4-(4-aminophenoxy)phenyl]sulfone (BAPS-p), (3,4-diaminodiphenylether (3,4-ODA) 4,4'-diaminodiphenylether (4,4'-ODA), 3,4'-diaminodiphenylether (DPE), 4,4'-bis(4-aminophenyl) sulfide (4,4-ASD), 4,4'-diaminodiphenyl sulfone (ASN or 4,4'-DDS), 4,4'-diaminobenzanilide (DABA), 1,3-bis(4-aminophenoxy)-2,2-dimethylpropane (DANPG), 1,2-bis[2-(4-aminophenoxy)ethoxy] ethane (DA3EG), 1,5-bis(4-aminophenoxy) pentane (DA5MG), 1,3-bis(4-aminophenoxy) propane (DA3MG), 1,3-bis(3-aminophenoxy)benzene (APB), 4,4'-bis(4-aminophenoxy) biphenyl (BAPB), 4,4'-bis(3-aminophenoxy)biphenyl, 2,2-bis[4-(4-aminophenoxy)phenyl]hexafluoropropane (HFBAPP), 3,3'-dicarboxy-4,4'-diaminodiphenylmethane (MBAA), 4,6-dihydroxy-1,3-phenylenediamine (also known as 4,6-diaminoresorcin), 3,3'-dihydroxy-4,4'-diaminobiphenyl (HAB), 3,3',4,4'-tetraminobiphenyl (TAB), or combinations thereof; aliphatic or alicyclic diamine compounds having a carbon number of 6 to 24, such as 1,6-hexamethylenediamine (HMD), 1,8-octamethylenediamine (OMDA), 1,9-nonamethylene diamine, 1,12-dodecamethylene diamine (DMDA), 1-amino-3-aminomethyl-3,5,5-trimethylcyclohexane, 4,4'-dicyclohexylmethanediamine, cyclohexanediamine, or combinations thereof; and silicone-based diamine compounds, such as 1,3-bis(3-aminopropyl)-1,1,3,3-tetramethyldisiloxane, polydimethyl siloxane (PDMS), or combinations thereof. Other embodiments may use one or more flexible comonomers that include: aromatic diamines (III) or (IV) (wherein each $R^3$ is independently selected from H, $CH_3$, or halogen, and n is an integer in the range of 1 to 7) and alkyl diamines, such as hexamethylene diamine (V):

(III)

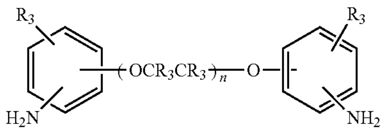

(IV)

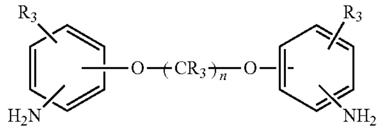

(V)

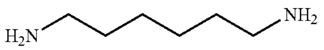

As mentioned above, in one or more embodiments of the application, the benzoxazine resin may be synthesized by the reaction of a bisphenol; amine(s) containing a maleimide functional group, a pyrocitric functional group, or a nitrile functional group; and an aldehyde (such as formaldehyde or paraformaldehyde). The bisphenol may optionally contain a heteroatom linkage. In some embodiments, the bisphenol may contain one or more maleimide functional groups, pyrocitric functional groups, and/or nitrile functional groups, instead of or in addition to the amine.

The bisphenol of one or more embodiments may be one or more selected from the group consisting of bisphenol A, bisphenol B, bisphenol C, bisphenol E, bisphenol AF, bisphenol AP, bisphenol Z, bisphenol S, bisphenol M, and substituted derivatives thereof.

In one or more embodiments, the amine is a primary amine containing at least one nitrogen-containing crosslinking functional group, such as a maleimide functional group or a pyrocitric functional group. Suitable amines may include primary amines including but not limited to a pyrocitric functional group selected from a citraconic imide functional group, an itaconic imide functional group, and a mesaconic imide functional group. Examples of suitable amines include but are not limited to 1-(4-aminophenyl)-3-methyl-1H-pyrrole-2,5-dione, 1-(3-aminophenyl)-3-methyl-1H-pyrrole-2,5-dione, 1-(2-aminophenyl)-3-methyl-1H-pyrrole-2,5-dione, 1-(4-aminophenyl)-3-methylenepyrrolidine-2,5-dione, 1-(3-aminophenyl)-3-methylenepyrrolidine-2,5-dione, 1-(2-aminophenyl)-3-methylenepyrrolidine-2,5-dione, 1-(4-aminophenyl)-3-methyl-1H-pyrrole-2,5-dione, 1-(3-aminophenyl)-3-methyl-1H-pyrrole-2,5-dione, 1-(2-aminophenyl)-3-methyl-1H-pyrrole-2,5-dione.

In one or more embodiments, the amine is a primary amine containing at least one nitrile functional group. Examples of suitable phenols include but are not limited to 4-aminobenzonitrile, 3-aminobenzonitrile, 2-aminobenzonitrile, 4-aminophenylacetonitrile, 3-aminophenylacetonitrile, 2-aminophenylacetonitrile, or combinations thereof.

When reacting with bisphenol, the amine may be present in a molar ratio ranging from 1:1 to 2:1, relative to the bisphenol. For example, in one or more embodiments, the molar ratio of amine to bisphenol may have a lower limit of any of 1:1, 1.2:1, or 1.4:1, to an upper limit of any of 1.6:1, 1.8:1, or 2:1, where any lower limit can be used in combination with any mathematically-compatible upper limit. In one or more embodiments, a single species of amine may be used or a combination may be used. When using a combination of amines, it is envisioned that a portion (but not all) of the amine used has at least one nitrogen-containing crosslinking functional group such as a maleimide functional group, a pyrocitric functional group, or a nitrile functional group. In such embodiments, the presence of a quantity of amine-containing compounds without maleimide groups, pyrocitric groups, and/or nitrile groups, in combination with amine-containing compounds having maleimide groups, pyrocitric groups, and/or nitrile groups, may result in a resin having fewer than four crosslinking sites. Thus, an amount of amine without maleimide groups, pyrocitric groups, and/or nitrile groups may be used in some embodiments to achieve varied properties in the benzoxazine resin or cured thermoset, including a reduced crosslinking density.

In any of the aforementioned reactions, the aldehyde or formaldehyde may be an aldehyde added directly or formed in situ. For example, the formaldehyde could be formed in situ from paraformaldehyde, polyoxymethylene, hexamethylenetetramine, or trioxane. Examples of suitable aldehydes include but are not limited to formaldehyde, paraformaldehyde, polyoxymethylene, hexamethylenetetramine, and trioxane.

In one or more embodiments, the benzoxazine resin may have a molecular weight ranging from 400 to 2000 Da, preferably 500 to 1000 Da.

The benzoxazine resin may form in the presence of one or more solvents (or co-solvents) in the temperature range of above 60° C. while stirring from hours to days. Examples of suitable solvent include but are not limited to chloroform, tetrahydrofuran, 2-methoxyethanol, benzene, dichloromethane, xylene, toluene, N-methyl-2-pyrrolidone, N,N-dimethylformamide, pyrrole, pyrrolidine, 1,4-dioxane, or combinations thereof. In particular embodiments, a combination of 1,4-dioxane and 2-methoxyethanol may allow for a homogeneous reaction phase and minimal formation of undesired byproducts, such as triazine, while maintaining the desired reaction temperatures.

For illustrative purposes, one or more embodiments of the benzoxazine resin of the present disclosure may be prepared according to reaction scheme (VI) shown below.

(VI)

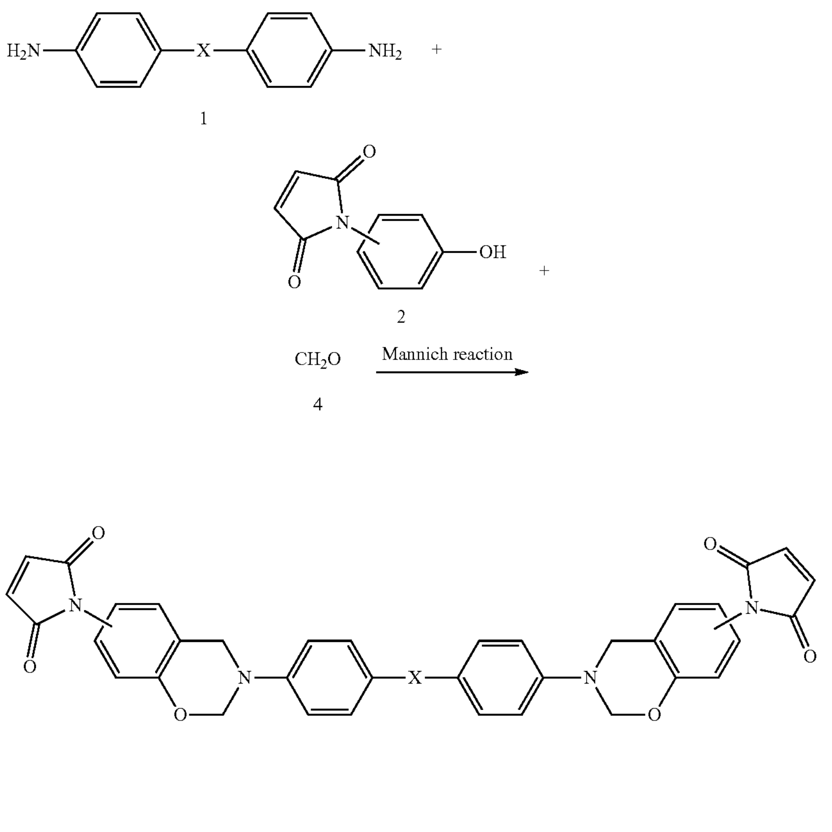

In particular embodiments of reaction scheme (VI), X may be selected from one or more of the following groups:

X =

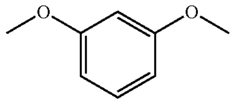

RODA-Bis(MI-BZ)

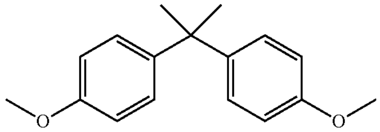

BAPP-Bis(MI-BZ)

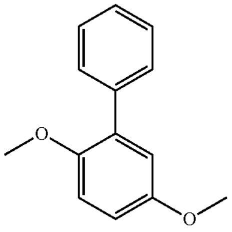

pTPEQ-Bis(MI-BZ)

In one or more embodiments, the benzoxazine resin may comprise at least one ether, sulfide, sulfone, or amide linkage, at least one benzoxazine ring, and at least one maleimide functional group. Examples of compounds include the following formula (VII)-(X):

(VII)

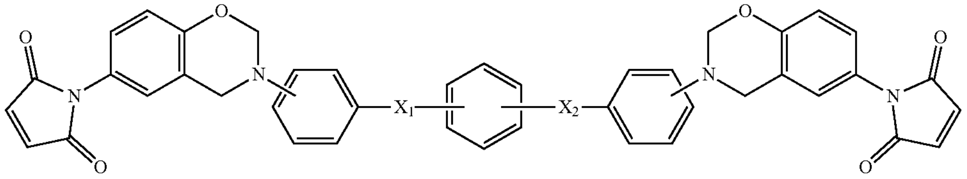

(VIII)

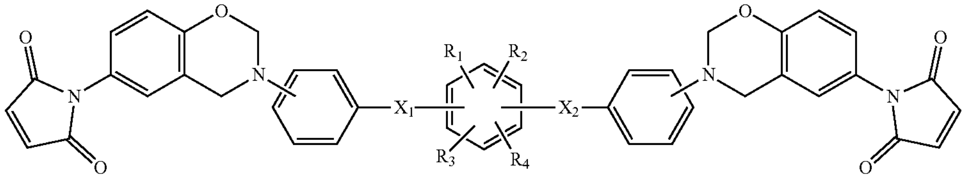

(IX)

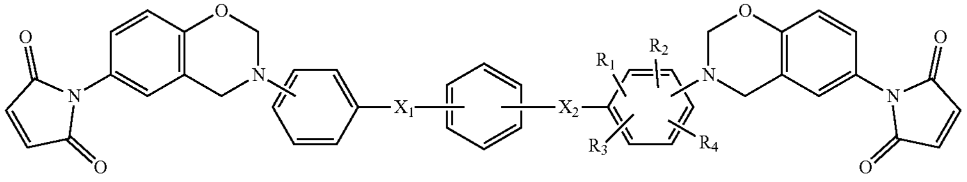

(X)

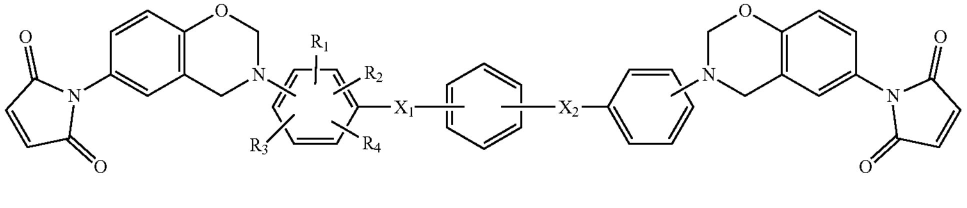

wherein $R_1$, $R_2$, $R_3$, and/or $R_4$ may be the same or different and represent a hydrogen, a linear or branched alkyl group having a carbon number of 1 to 20, an aromatic ring, and/or a substituent containing one or more maleimide functional group; $X_1$ and $X_2$ may be the same or different and represent an oxygen atom, a sulfur atom, a sulfone group (—OS(═O)$_2$ O—), and/or an amide (—N—C(═O)—) group.

Similarly, for illustrative purposes, one or more embodiments of the benzoxazine resin of the present disclosure may be prepared according to reaction scheme (XI) shown below.

(XI)

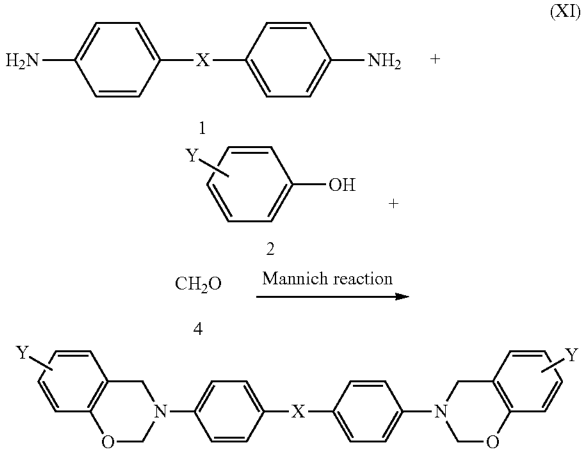

In particular embodiments of reaction scheme (XI), X and Y may be selected from one or more of the following groups:

X =

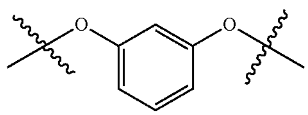

RODA

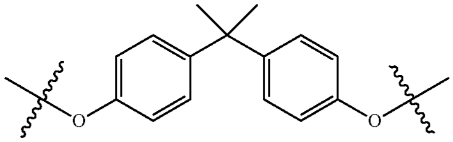

BAPP

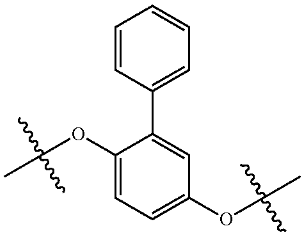

pTPE-Q

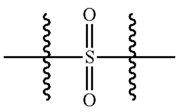

DDS

Y =

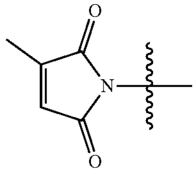

Citraconic imide
or
Mesaconic imide

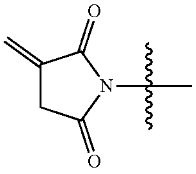

Itaconic imide

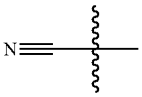

Nitrile

In one or more embodiments, the benzoxazine resin may comprise at least one alkyl, aromatic, cycloaliphatic, ether, sulfide, sulfone, or amide linkage, at least one benzoxazine ring, and at least one of maleimide functional groups, pyrocitric functional groups, and/or nitrile functional groups. Examples of compounds include the following formula (XII)-(XV):

(XII)

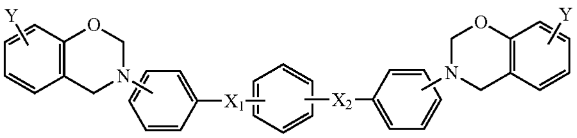

(XIII)

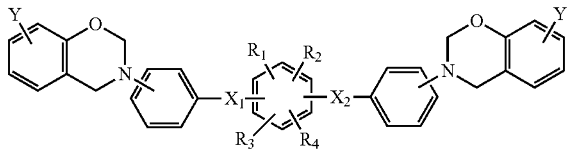

-continued (XIV)

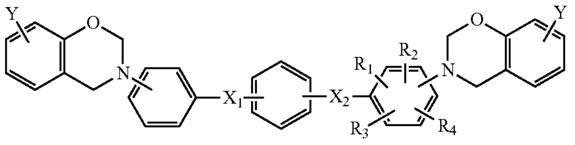

(XV)

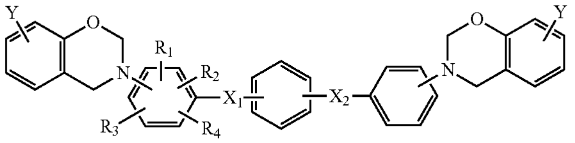

wherein $R_1$, $R_2$, $R_3$, and/or $R_4$ may be the same or different and represent a hydrogen, a linear or branched alkyl group having a carbon number of 1 to 20, an aromatic ring, and/or a substituent containing one or more maleimide functional groups, one or more pyrocitric functional groups and one or more nitrile functional groups; $X_1$ and $X_2$ may be the same or different and represent an oxygen atom, a sulfur atom, a sulfone group (—OS(═O)$_2$O—), and/or an amide (—N—C(═O)—) group; and Y may be a nitrogen-containing crosslinking functional group including one or more maleimide functional groups, one or more pyrocitric functional groups, and/or one or more nitrile functional groups.

The shape of the benzoxazine resin may involve a powder that includes, but is not limited to, a film, chunk, fiber, and so on. The film, chunk, or fiber can be made by thermal treatment of the powder of the benzoxazine resin or its solution using a press molding or casting method.

Embodiments disclosed herein also relate to curable compositions that include blends of a first compound having at least one imide functional group with at least one unsaturated carbon-carbon bond, and a second compound having at least one furan functional group. In such embodiments, at least one of the first compound and the second compound includes at least one benzoxazine functional group. Thus, the curable compositions disclosed herein include a benzoxazine resin.

In particular, embodiments disclosed herein relate to curable compositions that are non-solvent blends of a first compound comprising at least one imide functional group with at least one unsaturated carbon-carbon bond, and a second compound comprising at least one furan functional group, wherein one or more of the first compound and the second compound includes at least one benzoxazine functional group. The curable compositions may advantageously have good processability, including high melt-flowability at low temperatures, and be thermally curable at temperatures lower than conventional benzoxazine resins. Further, upon curing, the cured compositions may have high crosslinking density and high glass transition temperature, while also possessing good mechanical properties, including tensile properties.

In one or more embodiments, the curable composition may include a first compound comprising at least one imide functional group with at least one unsaturated carbon-carbon bond. In one or more embodiments, the first compound comprising at least one imide functional group that has at least one unsaturated carbon-carbon bond may also include at least one benzoxazine functional group. However, the benzoxazine group is not required in the first compound. The first compound may be one of the previously described benzoxazine resins, provided it has at least one imide functional group with at least one unsaturated carbon-carbon bond.

In one or more particular embodiments, in the first compound, the imide functional group that has at least one unsaturated carbon-carbon bond may be a maleimide functional group. Exemplary structures include structures (VII)-(X) above. Additional examples of first compounds having maleimide functional groups include, but are not limited to, the structures shown in formulas (XVI)-(XXII):

(XVI)

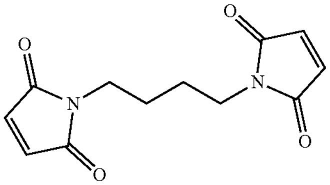

(XVII)

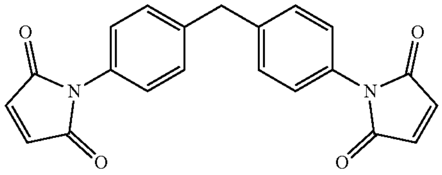

(XVIII)

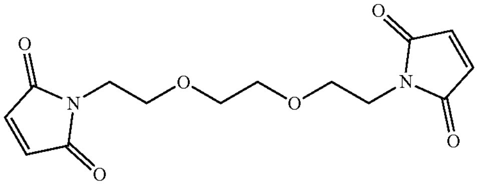

(IXX)

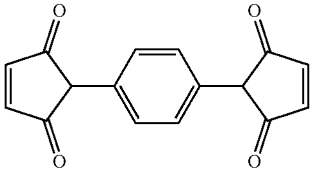

(XX)

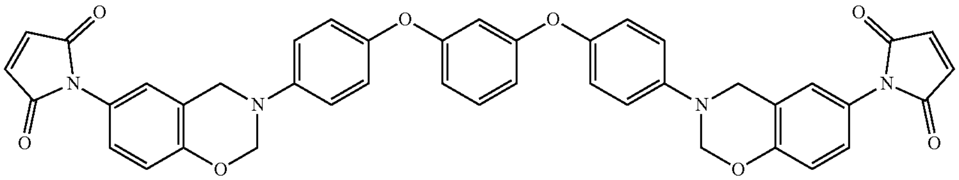

(XXI)

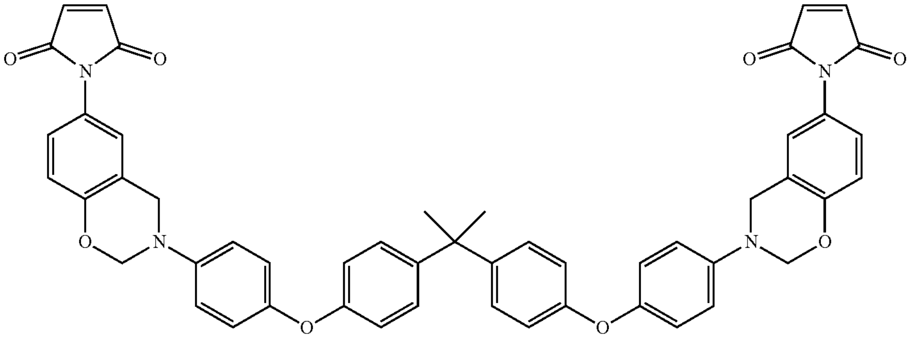

(XXII)

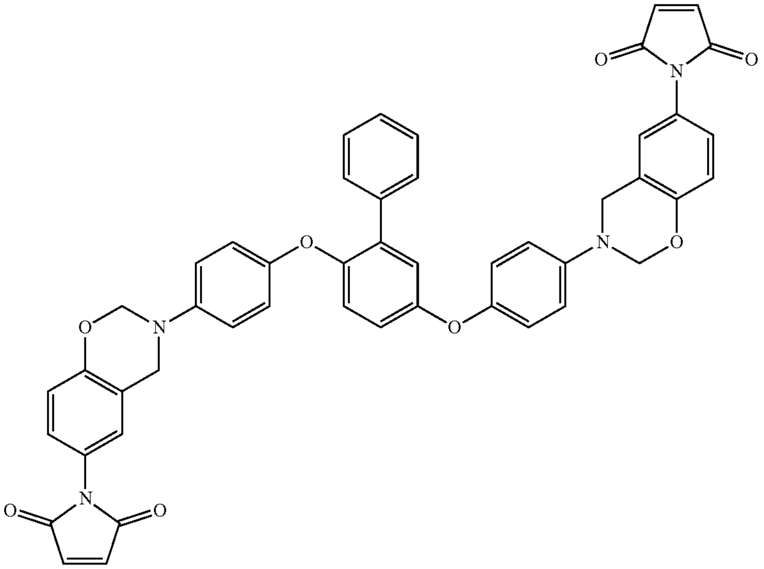

In other embodiments, in the first compound, the imide functional group having at least one unsaturated carbon-carbon bond may be a pyrocitric imide functional group. Exemplary structures include structures (XII)-(XV) above where Y is a pyrocitric functional imide group. Additional examples of first compounds having pyrocitric imide functional groups include, but are not limited to, the structures shown in formulas (XXIII)-(XXXVI):

(XXIII)

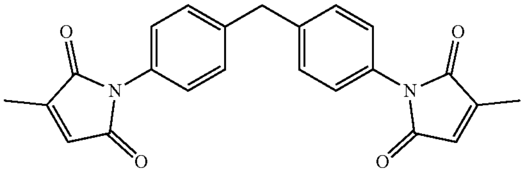

(XXIV)

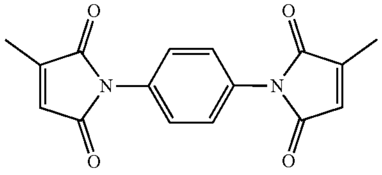

(XXV)

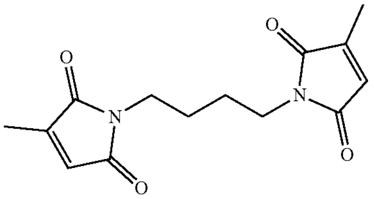

(XXVI)

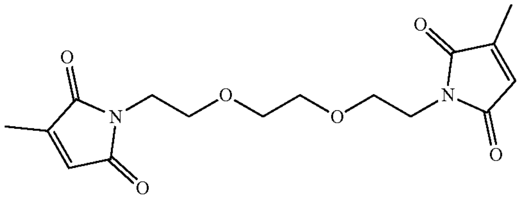

(XXVII)

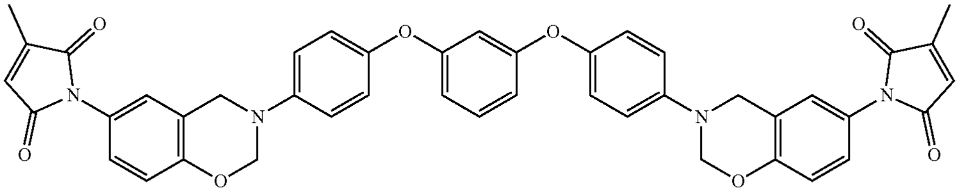

(XXVIII)

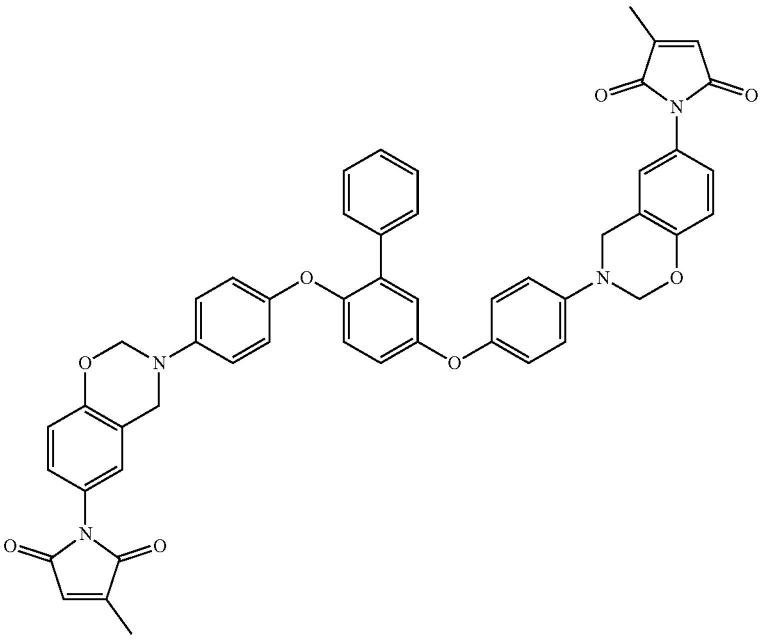

-continued
(IXXX)
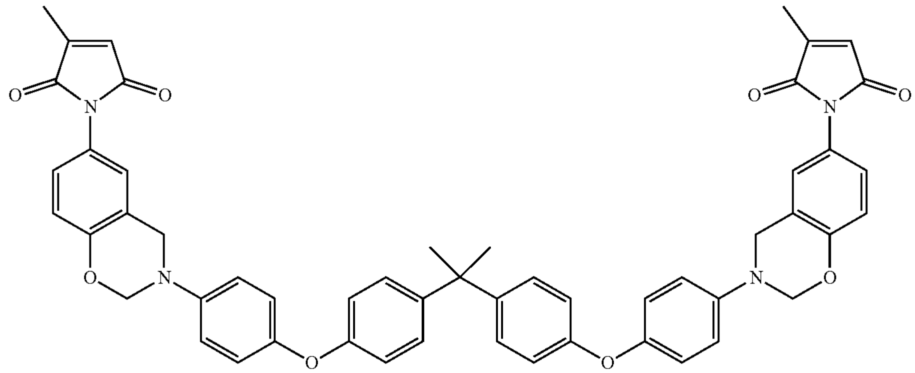
(XXX)
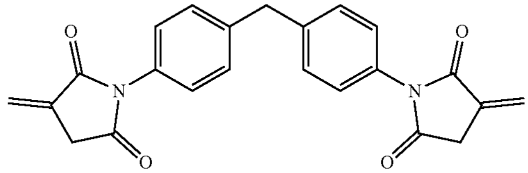
(XXXI)
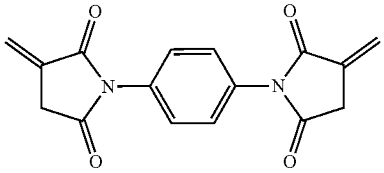
(XXXII)
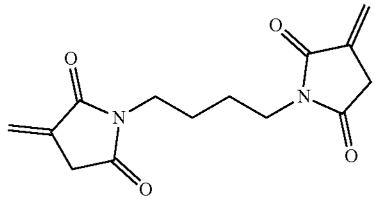
(XXXIII)
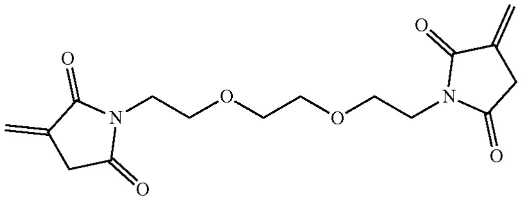
(XXXIV)
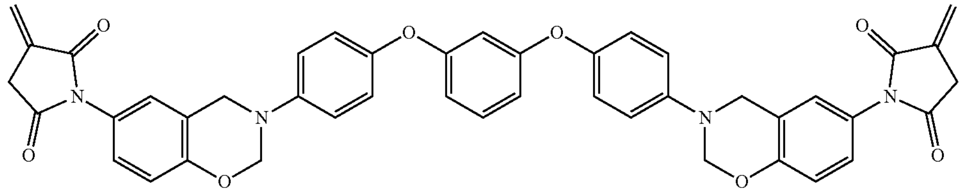
(XXXV)
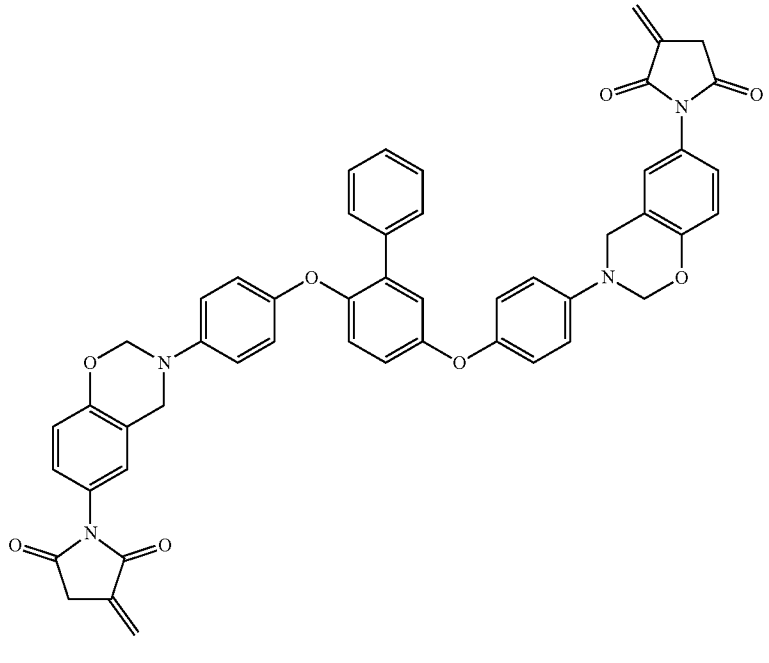

-continued (XXXVI)

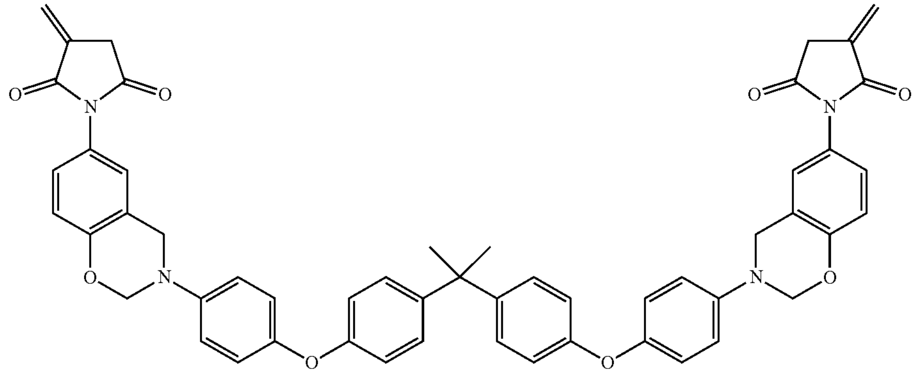

As noted above, the curable composition may include a first compound comprising at least one imide functional group with at least one unsaturated carbon-carbon bond, and a second compound comprising at least one furan functional group. In one or more embodiments, the curable composition may include a second compound comprising at least one furan functional group and at least one benzoxazine functional group. In particular embodiments, the curable composition may include a second compound comprising two furan functional groups and two benzoxazine functional groups. An exemplary structure is represented by formula (XXXVII):

(XXXVII)

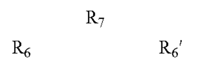

wherein $R_6$ may represent one or more of a hydrocarbon group and a substituted hydrocarbon group, containing at least one furan functional group. $R_6$' may be a group that is the same as, or different from, $R_6$. In one or more embodiments, with two benzoxazine groups and two furan functional groups, each molecule may have four crosslinking sites, which upon crosslinking result in a cured thermoset having a high crosslinking density. $R_7$ may be selected from, but is not limited to, a hydrocarbon, substituted hydrocarbon, ether, secondary-amino, amido, thioether, sulfonyl, sulfonamide, substituted sulfonamide, carbonyl, carbamyl, fluorenyl, alkoxycarbonyl groups, and mixtures thereof. In particular embodiments, $R_7$ may represent an aromatic group, including but not limited to a selection from benzene, bibenzyl, diphenylmethane, naphthalene, anthracene, diphenyl ether, diphenyl sulfone ether, bis(phenoxy) benzene, stilbene, phenanthrene, and fluorine groups, and substituted variants thereof. In particular embodiments, $R_7$ may represent a benzoxazine-containing moiety, resulting in an oligomeric or polymeric benzoxazine having a molecular weight less than 100,000 Da. In particular embodiments, $R_7$ may represent an oligomer or polymer, with a molecular weight less than 100,000 Da, including ring-opened benzoxazine-containing monomer units. In one or more embodiments, $R_7$ may represent a group with a molecular weight of a range of about less than 100,000 Da. In one or more embodiments, one or more compounds represented by formula (XXXVII) may be used in combination.

In one or more embodiments, the curable composition may include a second compound having a structure represented by formula (XVII):

(XXXVIII)

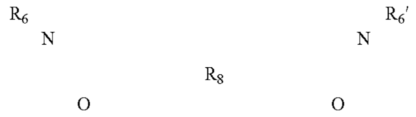

wherein $R_8$ represents a group as discussed above with regard to formula (XXXVII). $R_6$' may be a group that is the same as, or different from, $R_6$. $R_8$ may be selected from, but is not limited to, a hydrocarbon, substituted hydrocarbon, ether, secondary-amino, amido, thioether, sulfonyl, sulfonamide, substituted sulfonamide, carbonyl, carbamyl, fluorenyl, alkoxycarbonyl groups, and mixtures thereof. In particular embodiments, $R_6$ may represent a benzoxazine-containing moiety, resulting in an oligomeric or polymeric benzoxazine with a molecular weight less than 100,000 Da. In particular embodiments, $R_8$ may represent an oligomer or polymer, with a molecular weight less than 100,000 Da, including ring-opened benzoxazine-containing monomer units. In one or more embodiments, $R_8$ may represent a group with a molecular weight of less than 100,000 Da. In one or more embodiments, one or more compounds represented by formula (XXXVIII) may be used in combination. In one or more embodiments, one or more benzoxazines represented by formula (XXXVII) and (XXXVIII) may be used in combination.

Examples of the second compound may include, but are not limited to, the structures represented by formulas (IXXXX)-(XXXXI):

(IXXXX)

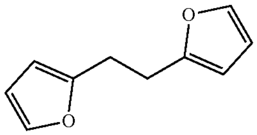

(XXXX)

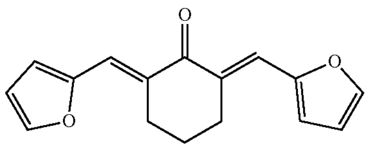

-continued (XXXXI)

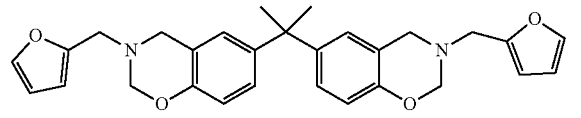

In one or more embodiments, the second compound may be included in the benzoxazine resin composition in an amount ranging between about 5% to about 90% by molar ratios (mol %), based on the total molar amount of the resin composition. In another embodiment, the second compound may be included in the resin composition in an amount ranging from a lower limit of one of 5 mol %, 10 mol %, 20 mol %, 30 mol %, and 50 mol %, and an upper limit of one of 50 mol %, 60 mol %, 70 mol %, 80 mol %, and 90 mol %, based on the total molar amount of the resin composition, where any lower limit can be used in combination with any mathematically-compatible upper limit. In embodiments where lower melt-viscosity, less shrinkage during curing, higher crosslinking density, and higher mechanical strength are desired in the cured article, the second compound may be included in the curable composition in an amount about 50 mol %, based on the total mole of the resin composition.

As previously described, curable compositions in accordance with one or more embodiments of the present disclosure generally include a benzoxazine functional group on at least one of the first compound and the second compound. However, in some embodiments, benzoxazine functionality may be introduced into the curable composition as an additional (i.e., a third) compound. In such embodiments, the curable composition may include a first compound having at least one imide functional group with at least one unsaturated carbon-carbon bond, a second compound with at least one furan functional group, and a third compound with at least one benzoxazine functional group.

In one or more embodiments, upon curing, the second compound comprising at least one furan functional group may crosslink, providing thermoset properties. In particular embodiments, the second compound used in the resin composition may include those that cure in a temperature range of 150 to 300° C., or at a temperature of 290° C. or less, 270° C. or less, or 250° C. or less in more particular embodiments. The curing temperature and other properties of the second compound comprising at least one furan functional group and at least one benzoxazine functional group are heavily affected by the selection of the benzoxazine, in particular, the structure of the benzoxazine and the selection of the molar ratio of the first compound in the curable composition. Therefore, the suitability of a given compound comprising at least one furan functional group and at least one benzoxazine functional group is dependent upon the rheological behavior of the compound and the resulting tensile, mechanical and thermal properties of the cured article of that compound. A low melting temperature may enable the second compound to be homogeneously mixed with other resins to form the resin composition of the present disclosure, and to be converted to the cured structure easily by thermal molding using a hot press, oven, autoclave, etc. It is also envisioned that the second compound may be blended with a non-reactive diluent to lower the melting temperature and melt-viscosity of the second compound. The non-reactive diluent may include, but is not limited to, a selection from non-polar solvents, such as 1,4-dioxane, benzene, toluene, and chloroform; polar aprotic solvents, such as dimethyl sulfoxide, N-methylpyrrolidone, tetrahydrofuran, ethyl acetate, N,N-dimethylformamide, acetonitrile, propylene carbonate, and N,N-dimethylacetamide; polar protic solvents, such as methanol, ethanol, isopropanol, nitromethane; and combinations thereof.

While curable compositions of the present disclosure generally include the first compound and the second compound, as previously described, in some embodiments, a curable composition may only include the second compound. In such embodiments, the cured composition may include at least one furan functional group and at least one benzoxazine functional group. Such compounds may also undergo crosslinking as a result of thermal activation, and result in resins having desirable properties. In another embodiment, a curable composition may only include the first compound. In such embodiments, the cured composition may include at least one imide functional group with at least one unsaturated carbon-carbon bond and at least one benzoxazine functional group. Such compounds may also undergo crosslinking as a result of thermal activation, and result in resins having desirable properties.

The benzoxazine resin of the present disclosure may be cured via thermal activation. In one or more embodiments, the resin undergoes curing by ring-opening of benzoxazine moiety upon thermal activation. In one or more embodiments, the resin undergoes curing by [2+2] Cycloaddition of maleimide or pyrocitric functional groups. In one or more embodiments, the resin undergoes curing by triazine ring formation of nitriles. In one or more embodiments, the resin undergoes curing by Michael addition-type reaction of a phenolic group of ring-opened benzoxazine moiety to an $\alpha,\beta$-unsaturated carbonyl component of maleimide or pyrocitric moiety. In one or more embodiments, the curing of the benzoxazine moiety is conducted at a temperature less than the resin degradation temperature. In one or more embodiments, the curing is conducted at a temperature less than about 300° C.

In embodiments in which the second compound including furan functionality is included in the composition, thermal curing of the benzoxazine resin may occur by the following curing mechanisms: ring-opening of benzoxazine moieties; reaction between a maleimide or pyrocitric imide moiety and a furan moiety by the Diels-Alder [4+2] Cycloaddition reaction; reaction between two maleimide and/or pyrocitric moieties by [2+2] cycloaddition; reaction between a maleimide or pyrocitric imide moiety and a phenol of the ring-opened benzoxazine by the Michael addition-type reaction; and reaction between a furan moiety and a phenol of the ring-opened benzoxazine by the Michael addition-type reaction. The first compound and the second compound reduce the curing temperature of the curable composition by favorable Diels-Alder [4+2] Cycloaddition reaction between a maleimide or pyrocitric imide functional group in the resin and a furan functional group in the second compound, and the Michael addition-type reaction between a furan functional group in the second compound and a phenol of a ring-opened benzoxazine. The above-mentioned series of crosslinking reactions between the resin components increase crosslinking density, and allow for improvement of thermal and mechanical properties of the cured article of the curable composition.

In one or more embodiments, the benzoxazine resin may be cured in a variety of manners, including but not limited to a cure cycle, solution casting, hot-melt pressing, etc. The cure mechanism may be selected depending on the type of article and the way in which the benzoxazine resin is to be used, for example, as an impregnator (such as in composite fibers to form a prepreg), composite, adhesive, coating, etc.

As used herein, a cured resin refers to a resin that has undergone one of the previously described curing processes to be cured to an extent of between 5% cured and 100% cured. A "fully cured" resin is a resin with a 100% degree of curing, any resin with a degree of curing below 100% is a "partially cured" resin. In one or more embodiments, the benzoxazine resin may be cured to a curing extent ranging from 5% to 100%. The curing extent in the cured benzoxazine resin may have a lower limit of one of 5%, 10%, 15%, 20%, 25%, 30%, 35%, and 40% and an upper limit of one of 45%, 50%, 55%, 60%, 65%, 70%, 75%, 80%, 85%, 90%, 95% and 100%, where any lower limit may be paired with any mathematically-compatible upper limit.

In one or more embodiments, the benzoxazine resin may be formulated with additives, tougheners made from thermoplastic resins, thermosetting resins, inorganic salts, organic compounds, and so on. The formulation can be performed by a powder dry mixing, melt mixing, or mixing in solution. The shape of both the additives and the tougheners may involve a particle that may include, but is not limited to, a plate or a fiber, for example. One or more additives, tougheners, and fibers may be formulated together with the benzoxazine resin. For example, one or more thermoplastic resins can be formulated together with the benzoxazine resin. Such thermoplastic resin may include, but is not limited to, poly(ether ether ketone), poly(ether ketone), poly(phenylene sulfide), poly(ether imide), polycarbonate, polysulfone, and so on. In another example, one or more thermosetting resins can be formulated together with the benzoxazine resin and thermally co-cured. Such thermosetting resin may include, but is not limited to, epoxy, benzoxazine, bismaleimide, cyanate ester, and so on. It is also envisioned that the thermoplastic and the thermosetting resins can be used together with the benzoxazine resin of the present disclosure. In one or more embodiments, inorganic salts, organic compounds, or a combination thereof may be used with the benzoxazine resin to lower the curing temperature. For example, the organic compound involves a functional group including, but not limited to, an amino group, imidazole group, carboxylic group, hydroxy group, sulfonyl group, and so on.

In one or more embodiments, the curable composition may be optionally formulated with one or more amine compound(s), such as diamines. The formulation can be performed by a powder dry mixing, melt mixing, or mixing in solution. Such diamines may include, but are not limited to, aromatic diamine compounds having a carbon number of 6 to 27, such as bis[4-(3-aminophenoxy)phenyl]sulfone (BAPS-m), bis[4-(4-aminophenoxy)phenyl]sulfone (BAPS-p), 1,4-diaminobenzene (PPD), 1,3-diaminobenzene (MPD), 2,4-diaminotoluene (2,4-TDA), 4,4'-diaminodiphenylmethane (MDA), 4,4'-diaminodiphenylether (ODA), 3,4'-diaminodiphenylether (DPE), 3,3'-dimethyl-4,4'-diaminobiphenyl (TB), 2,2'-dimethyl-4,4'-diaminobiphenyl (m-TB), 2,2'-bis(trifluoromethyl)-4,4'-diaminobiphenyl (TFMB), 3,7-diamino-dimethyldibenzothiophen-5,5-dioxide (TSN), 4,4'-diaminobenzophenone, 3,3'-diaminobenzophenone, 4,4'-bis(4-aminophenyl) sulfide (ASD), 4,4'-diaminodiphenyl sulfone (ASN), 4,4'-diaminobenzanilide (DABA), 1,n-bis(4-aminophenoxy)alkane (n=3, 4, or 5, DAnMG), 1,3-bis(4-aminophenoxy)-2,2-dimethylpropane (DANPG), 1,2-bis[2-(4-aminophenoxy)ethoxy]ethane (DA3EG), 1,5-bis(4-aminophenoxy) pentane (DA5MG), 1,3-bis(4-aminophenoxy) propane (DA3MG), 9,9-bis(4-aminophenyl)fluorene (FDA), 5(6)-amino-1-(4-aminomethyl)-1,3,3-trimethylindan, 1,4-bis(4-aminophenoxy)benzene (TPE-Q or APB-144), 1,3-bis(4-aminophenoxy)benzene (TPE-R or APB-134 or RODA), 1,3-bis(3-aminophenoxy)benzene (APB or APB-133)), 4,4'-bis(4-aminophenoxy) biphenyl (BAPB), 4,4'-bis(3-aminophenoxy)biphenyl, 2,2-bis(4-aminophenoxyphenyl) propane (BAPP), 2,2-bis[4-(4-aminophenoxy)phenyl] hexafluoropropane (HFBAPP), 3,3'-dicarboxy-4,4'-diaminodiphenylmethane (MBAA), or 4,6-dihydroxy-1,3-phenylenediamine (known as 4,6-diaminoresorcin), 3,3'-dihydroxy-4,4'-diaminobiphenyl (HAB) and 3,3',4,4'-tetraminobiphenyl (TAB); aliphatic or alicyclic diamine compounds having a carbon number of 6 to 24 such as 1,6-hexamethylenediamine (HMD), 1,8-octamethylenediamine (OMDA), 1,9-nonamethylene diamine, 1,12-dodecamethylene diamine (DMDA), 1-amino-3-aminomethyl-3,5,5-trimethylcyclohexane, 4,4'-dicyclohexylmethanediamine and cyclohexanediamine; silicone based diamine compounds such as 1,3-bis(3-aminopropyl)-1,1,3,3-tetramethyldisiloxane and polydimethyl siloxane (PDMS); or combinations thereof. One or more embodiments may use one or more flexible comonomers that include: aromatic diamines (for example, the diamines having formula (III) and IV) above), and alkyl diamines (for example, the diamines having formula (V) above).

In one or more embodiments, the curable composition may be optionally formulated with one or more bisphenol-containing compound(s). The formulation can be performed by a powder dry mixing, melt mixing, or mixing in solution. Such bisphenol-containing compounds of one or more embodiments may have a structure as represented by formula (XXXXII):

(XXXXII)

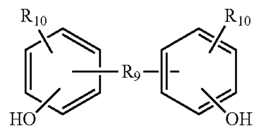

where $R_9$ may represent a hydrocarbon group or a substituted hydrocarbon group. Rio is not particularly limited and can represent one or more of a hydrogen atom, a hydrocarbon group, a substituted hydrocarbon group, and/or a functional group. The bisphenol-containing compounds of one or more embodiments may include one or more substituents represented by Rio. The bisphenol-containing compound of one or more embodiments may be one or more of the group consisting of 2,2'-bis(4-hydroxyphenyl)propane (bisphenol A), 2,2'-bis(4-hydroxyphenyl)butane (bisphenol B), 1,1'-bis (4-hydroxyphenyl)ethane (bisphenol E), 2,2'-bis(4-hydroxy-3-isopropylphenyl)propane (bisphenol G), bis(4-hydroxyphenyl)methane (bisphenol F), 2,2'-bis(4-hydroxyphenyl) hexafluoropropane (bisphenol AF), 4,4'-(1-phenylethylidene)bisphenol (bisphenol AP), 4,4'-cyclohexylidenebisphenol (bisphenol Z), bis(4-hydroxyphenyl) sulfone (bisphenol S), 4,4'-(9-fluorenylidene) diphenol (bisphenol FL), 4,4'-(1,3-phenylenediisopropylidene) bisphenol (bisphenol M), 4,4'-(1,4-phenylenediisopropylidene) bisphenol (bisphenol P), and substituted derivatives thereof. In particular embodiments, the bisphenol-containing compound may be one or more of 3,3'-dimethylbisphenol A (bisphenol C), 3,3'-diallylbisphenol A, and 2,2'-bis(2-hydroxy-5-biphenylyl)propane (Bisphenol PH). In one or more embodiments, one or more bisphenol-containing monomers represented by formula (XXXXII) may be used in combination.

In one or more embodiments, the benzoxazine resin may be formulated with epoxy compounds. The formulation can be performed by a powder dry mixing, melt mixing, mixing in solution, and so on. For example, one or more epoxy compounds can be formulated together with the benzoxazine resin. Such epoxy compounds may include, but are not limited to, polyglycidyl epoxy compound, such as polyglycidyl ether or polyglycidyl ester.

In one or more embodiments, the benzoxazine resin may be thermally cured in the temperature range of 150 to 300° C.; it may be subjected to a longer period of curing time at the lower end of the range, and a shorter period of time at the upper end of the range, based on the desired application.

In one or more embodiments, the benzoxazine resin may be thermally cured for a time of a range of 10 min to 30 hours. In some embodiments, the cure condition may involve several continuing steps.

In one or more embodiments, the shape of the cured article of the benzoxazine resin may involve a powder that includes, but is not limited to, a film, chunk, fiber, and so on. The cured article is partially or fully cured with other resins together at both of the surfaces. The benzoxazine resin may be partially or fully cured with other resins such as thermoplastic resins, thermosetting resins, glass plates, fibers, or metals, at either or both of the surfaces of the resulting articles.

In one or more embodiments, the benzoxazine resin may have a 5% decomposition temperature (Td5%) above 250° C., above 300° C., above 320° C., above 340° C., above 350° C., or above 400° C.

In one or more embodiments, the melt-viscosity of the benzoxazine resin (or curable composition) may be altered, for example, through selection of the above reactants (such as a diamine, amine, bisphenol, or phenol forming the benzoxazine resin), and additional compounds (such as the second compound comprising at least one furan functionality). Thus, for example, in the temperature range of 50 and 300° C., the melt-viscosity may range from 1 Pa·s to over 1700-Pa·s. In one or more embodiments, the melt-viscosity of the benzoxazine resin may be lower than 5000 Pa·s in the temperature range of 80 and 280° C., and lower than 100 Pa·s in the temperature range of 110 and 260° C.

In one or more embodiments, the curable composition may have an on-set curing temperature of less than about 150° C., or less than about 140° C., or less than about 130° C.

In one or more embodiments, the cured article of the benzoxazine resin may have a glass transition temperature (Tg) above 200° C., preferably above 220° C., preferably above 240° C., more preferably 260° C.

In one or more embodiments, the cured article of the benzoxazine resin may have a tensile strength, measured according to ASTM D1708, ranging from 30 to 150 MPa. The tensile strength of the cured article may have a lower limit of one of 30, 40, 50, 60, 70, and 80 MPa and an upper limit of one of 90, 100, 110, 120, 130, 140 and 150 MPa, where any lower limit may be used in combination with any mathematically-compatible upper limit.

In one or more embodiments, the cured article of the benzoxazine resin may have a tensile modulus, measured according to ASTM D1708, ranging from 1 to 10 GPa. The tensile modulus of the cured article may have a lower limit of one of 1, 2, 3, 4, and 5 GPa and an upper limit of one of 6, 7, 8, 9 and 10 GPa, where any lower limit may be used in combination with any mathematically-compatible upper limit.

In one or more embodiments, the cured article of the benzoxazine resin may have an elongation at break, measured according to ASTM D1708, ranging from 1 to 10%. The elongation at break of the cured article may have a lower limit of one of 1%, 2%, 3%, 4%, and 5% and an upper limit of one of 6%, 7%, 8%, 9%, and 10%, where any lower limit may be used in combination with any mathematically-compatible upper limit.

In one or more embodiments, the benzoxazine resin (or the curable composition) of the present disclosure may be used to form prepregs, composite materials, adhesives, coatings, etc. Specifically, the benzoxazine resin as discussed above may be included in a curable matrix resin that is combined with reinforcement fibers to form a composite material or structure, including prepregs formed by impregnating a layer or weave of fibers. A resin film may be formed from the curable matrix resin that comprises the benzoxazine resin by, for example, compression molding, extrusion, melt-casting, or belt-casting, followed by laminating such film to one or both opposing surfaces of another layer, including for example a layer of reinforcement fibers in the form of, for example, a non-woven mat of relatively short fibers, a woven fabric of continuous fibers, or a layer of unilaterally aligned fibers (i.e., fibers aligned along the same direction), at temperature and pressure sufficient to cause the resin film to flow and impregnate the fibers. Alternatively, a prepreg may be fabricated by providing the curable matrix resin that comprises the benzoxazine resin in liquid form, and passing the layer of fibers through the liquid resin composition to infuse the layer of fibers with the heat curable composition, and removing the excess resin from the infused fibrous layer.

In one or more embodiments, to fabricate a composite part from prepregs, plies of impregnated reinforcing fibers are laid up on a tool and laminated together by heat and pressure, for example by autoclave, vacuum, or compression molding, or by heated rollers, at the curing temperature range of the benzoxazine rein and at a pressure in particular in excess of 1 bar, preferably in the range of 1 to 10 bar.

In one embodiment, the benzoxazine resin of the present disclosure may be included in the resin system used for the manufacture of structural composites, such as in the automotive, marine, or aerospace industries. Such resin system may be advantageous to a wide variety of different manufacturing processes for such structural composites, including but not limited to autoclave molding and hot press molding using prepreg, filament winding, pultrusion, resin infusion (various techniques including resin transfer molding (RTM), vacuum-assisted resin transfer molding (VARTM), seemann composites resin infusion molding process (SCRIMP), etc.), and compression molding.

In the formation of a coating or adhesive layer, application of the formulated coating may be made via conventional methods, such as spraying, roller coating, dip coating, etc., and then, the coated system may be cured by baking.

EXAMPLES

The following examples are provided to illustrate embodiments of the present disclosure. The examples are not intended to limit the scope of the present invention, and they should not be so interpreted.

Materials 1,3-bis(4-aminophenoxy) benzene (RODA), 2,2-bis[4-(4-aminophenoxy)phenyl]propane (BAPP), 4-[4-(4-aminophenoxy)-3-phenylphenoxy]aniline (p-TPE-Q), and 4,4'-diaminodiphenyl sulfone (DDS) were obtained from Wakayama Seika Kogyo Co. Ltd. Paraformaldehyde, citraconic anhydride, p-toluenesulfonic acid monohydrate, 4-aminophenol, 2-hydroxybenzonitrile (2-HIBN), 1,4-dioxane, 2-methoxyehtanol, acetone, tetrahydrofuran (THF), hexane, N,N-dimethylformamide (DMF), 2-methoxyehtanol, ethyl acetate, sodium hydroxide, furfuryl amine, and deuterated diemethylsulfoxide (DSMO-$d_6$) are commercially available from Sigma Aldrich, TCI America, and VWR. N-(4-hydroxyphenyl)maleimide is commercially available from Biosynth CarboSynth and ALFA Chemistry.

Measurements

Nuclear Magnetic Resonance Spectroscopy (NMR)

$^1$H nuclear magnetic resonance (NMR) spectra were acquired in DMSO-$d_6$ and recorded on Varian Inova 500 MHz console with an Oxford magnet interfaced to UNIX computers using VnmrJ software. Chemical shifts were referenced to solvent resonance signals.

Thermogravimetric Analyzer (TGA)

A TGA (TA Q500) using TA Universal Analysis software was operated at a heating rate of 5° C./min, in the range of 50 to 800° C., at $N_2$ atmosphere.

Differential Scanning Calorimeter (DSC)

DSC (TA Q20) using TA Universal Analysis software was operated at a scan rate of 5° C./min, in the range of 50 to 320° C., at $N_2$ atmosphere. Weight loss measurements ($T_{d,5\%}$) were carried out under the same conditions.

Rheology (Melt-Viscosity)

A dynamic mechanical analysis (DMA) (Discovery HR-2 Hybrid Rheometer) using Trios software was operated at a heating rate of 5° C./min, in the range of 50 to 300° C., an angular frequency of 6.283 rad/s (1.0 Hz), and a strain of 0.1%. A parallel plate having a 25 mm diameter was used.

Dynamic Mechanical Analysis (DMA)

DMA with tensile thin-film configuration was applied. The measurement condition was amplitude 15 μm, preload 0.01 N, force track 125%, ramp from 50 to 400° C. at 5° C./min.

Tensile Test

A tensile testing machine (product name: eXpert 4200, manufactured by ADMET), was used for measurement of elastic modulus, tensile strength, and elongation—at beak at room temperature at a tensile speed of 1 mm/min. The test pieces had a film-like shape having a length of 40 mm, a width of 5 mm, and a thickness of 80 to 120 microns.

Example 1: Synthesis of 1,3-bis(4-aminophenoxy) benzene-bis(maleimide-benzoxazine) (RODA-Bis (MI-BZ)) Shown in FIG. 1

In a 50 mL of round-bottom flask equipped with a magnetic stir bar, N-(4-hydroxyphenyl)maleimide (1.3242 g, 0.0070 mol), 1,3-bis(4-aminophenoxy) benzene (RODA) (1.0232 g, 0.0035 mol), and paraformaldehyde (0.4204 g, 0.0140 mol) were placed, and then xylene (11 mL) was added. After stirring for 30 min at ambient temperature, the solution was refluxed for 3-5 h while vigorously stirring. Once the solution was cooled down to room temperature, the solution was poured into hexane while stirring. After removal of solvent, the collected powder product was re-dissolved in tetrahydrofuran, and then, it was re-precipitated into hexane. Finally, the desired product, RODA-Bis(MI-BZ), was obtained after drying in vacuo overnight (Yield ~30%).

Example 2: Synthesis of 1,3-bis(4-aminophenoxy) benzene-bis(maleimide-benzoxazine) (RODA-Bis (MI-BZ))

In a 50 mL of round-bottom flask equipped with a magnetic stir bar, N-(4-hydroxyphenyl)maleimide (1.3242 g, 0.0070 mol), 1,3-bis(4-aminophenoxy) benzene (RODA) (1.0232 g, 0.0035 mol), and paraformaldehyde (0.4204 g, 0.0140 mol) were placed and then 1,4-dioxane (11 mL) was added. After stirring for 30 min at ambient temperature, the solution was refluxed for 2-3 days while vigorously stirring. Once the solution was cooled down to room temperature, it was precipitated into hexane while stirring. After removal of solvent, the collected powder product was re-dissolved in tetrahydrofuran, and then it was re-precipitated into hexane. Finally, the desired product, RODA-Bis(MI-BZ), was obtained after drying in vacuo overnight (Yield ~90%).

Example 3: Synthesis of 1,3-bis(4-aminophenoxy) benzene-bis(maleimide-benzoxazine) (RODA-Bis (MI-BZ))

In a 50 mL of round-bottom flask equipped with a magnetic stir bar, N-(4-hydroxyphenyl)maleimide (1.3242 g, 0.0070 mol), 1,3-bis(4-aminophenoxy) benzene (RODA) (1.0232 g, 0.0035 mol), and paraformaldehyde (0.4204 g, 0.0140 mol) were placed, and then 1,4-dioxane and 2-methoxyehtanol (2:1 volume ratio) (11 mL) were added. After stirring for 30 min at ambient temperature, the solution was refluxed for 2-3 days while vigorously stirring. Once the solution was cooled down to room temperature, it was precipitated into hexane while stirring. After removal of solvent, the collected powder product was re-dissolved in tetrahydrofuran, and then it was re-precipitated into hexane. Finally, the desired product, RODA-Bis(MI-BZ), was obtained after drying in vacuo overnight (Yield ~90%).

Figure 2:
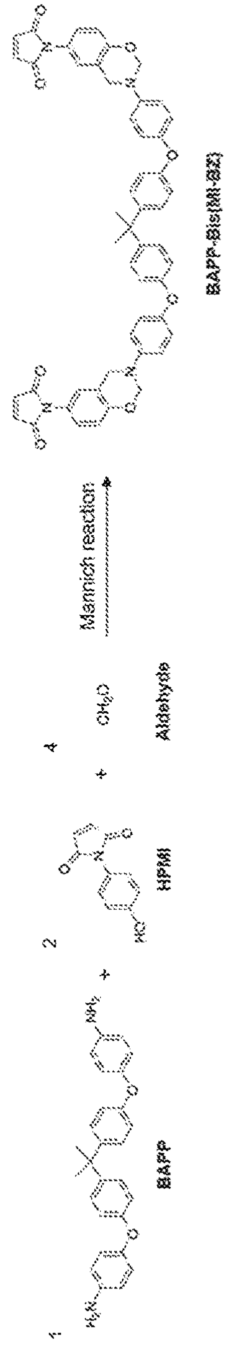
FIG. 2 shows a reaction scheme for the formation of BAPP-Bis(MI-BZ) in accordance with embodiments of the present disclosure.

Example 4: Synthesis of 2,2-bis[4-(4-aminophenoxy)phenyl]propane-bis(maleimide-benzoxazine) (BAPP-Bis(MI-BZ)) Shown in FIG. 2

In a 50 mL of round-bottom flask equipped with a magnetic stir bar, N-(4-hydroxyphenyl)maleimide (1.3242 g, 0.0070 mol), 2,2-bis[4-(4-aminophenoxy)phenyl]propane (BAPP) (1.4368 g, 0.0035 mol), and paraformaldehyde (0.4204 g, 0.0140 mol) were placed, and then xylene (11 mL) was added. After stirring for 30 min at ambient temperature, the solution was refluxed for 3-5 h while vigorously stirring. Once the solution was cooled down to room temperature, the solution was poured into hexane while stirring. After removal of solvent, the collected powder product was re-dissolved in tetrahydrofuran, and then it was re-precipitated into hexane. Finally, the desired product, BAPP-Bis(MI-BZ), was obtained after drying in vacuo overnight (Yield ~30%).

Example 5: Synthesis of 2,2-bis[4-(4-aminophenoxy)phenyl]propane-bis(maleimide-benzoxazine) (BAPP-Bis(MI-BZ))

In a 50 mL of round-bottom flask equipped with a magnetic stir bar, N-(4-hydroxyphenyl)maleimide (1.3242 g, 0.0070 mol), 2,2-bis[4-(4-aminophenoxy)phenyl]propane (BAPP) (1.4368 g, 0.0035 mol), and paraformaldehyde (0.4204 g, 0.0140 mol) were placed, and then 1,4-dioxane (11 mL) was added. After stirring for 30 min at ambient temperature, the solution was refluxed for 2-3 days while vigorously stirring. Once the solution was cooled down to room temperature, it was precipitated into hexane while stirring. After removal of solvent, the collected powder product was re-dissolved in tetrahydrofuran, and then it was re-precipitated into hexane. Finally, the desired product, BAPP-Bis(MI-BZ), was obtained after drying in vacuo overnight (Yield ~90%).

Example 6: Synthesis of 2,2-bis[4-(4-aminophenoxy)phenyl]propane-bis(maleimide-benzoxazine) (BAPP-Bis(MI-BZ))

In a 50 mL of round-bottom flask equipped with a magnetic stir bar, N-(4-hydroxyphenyl)maleimide (1.3242 g, 0.0070 mol), 2,2-bis[4-(4-aminophenoxy)phenyl]propane (BAPP) (1.4368 g, 0.0035 mol), and paraformaldehyde (0.4204 g, 0.0140 mol) were placed, and then 1,4-dioxane and 2-methoxyehtanol (2:1 volume ratio) (11 mL) were added. After stirring for 30 min at ambient temperature, the solution was refluxed for 2-3 days while vigorously stirring. Once the solution was cooled down to room temperature, it was precipitated into hexane while stirring. After removal of solvent, the collected powder product was re-dissolved in tetrahydrofuran, and then it was re-precipitated into hexane. Finally, the desired product, BAPP-Bis(MI-BZ), was obtained after drying in vacuo overnight (Yield ~90%).

Figure 3:
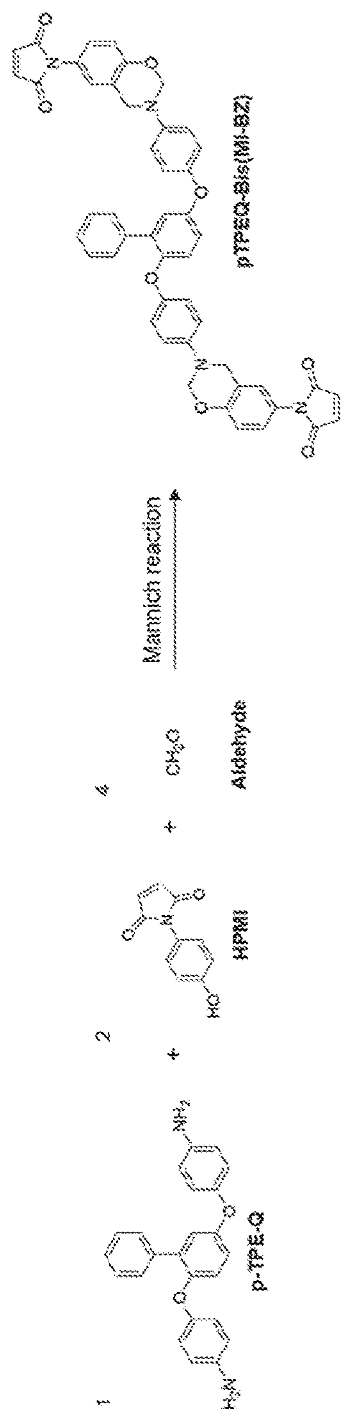
FIG. 3 shows a reaction scheme for the formation of pTPEQ-Bis(MI-BZ) in accordance with embodiments of the present disclosure.

Example 7: Synthesis of 4-[4-(4-aminophenoxy)-3-phenylphenoxy]aniline-bis(maleimide-benzoxazine) (pTPEQ-Bis(MI-BZ)) Shown in FIG. 3

In a 50 mL of round-bottom flask equipped with a magnetic stir bar, N-(4-hydroxyphenyl)maleimide (1.3242 g, 0.0070 mol), 4-[4-(4-aminophenoxy)-3-phenylphenoxy] aniline (pTPEQ) (1.2895 g, 0.0035 mol), and paraformaldehyde (0.4204 g, 0.0140 mol) were placed, and then xylene (11 mL) was added. After stirring for 30 min at ambient temperature, the solution was refluxed for 3-5 h while vigorously stirring. Once the solution was cooled down to room temperature, the solution was poured into hexane while stirring. After removal of solvent, the collected powder product was re-dissolved in tetrahydrofuran, and then it was re-precipitated into hexane. Finally, the desired product, pTPEQ-Bis(MI-BZ), was obtained after drying in vacuo overnight (Yield ~30%).

Example 8: Synthesis of 4-[4-(4-aminophenoxy)-3-phenylphenoxy]aniline-bis(maleimide-benzoxazine) (pTPEQ-Bis(MI-BZ))

In a 50 mL of round-bottom flask equipped with a magnetic stir bar, N-(4-hydroxyphenyl)maleimide (1.3242 g, 0.0070 mol), 4-[4-(4-aminophenoxy)-3-phenylphenoxy] aniline (pTPEQ) (1.2895 g, 0.0035 mol), and paraformaldehyde (0.4204 g, 0.0140 mol) were placed, and then 1,4-dioxane (11 mL) was added. After stirring for 30 min at ambient temperature, the solution was refluxed for 2-3 days while vigorously stirring. Once the solution was cooled down to room temperature, it was precipitated into hexane while stirring. After removal of solvent, the collected powder product was re-dissolved in tetrahydrofuran, and then it was re-precipitated into hexane. Finally, the desired product, pTPEQ-Bis(MI-BZ), was obtained after drying in vacuo overnight (Yield ~90%).

Example 9: Synthesis of 4-[4-(4-aminophenoxy)-3-phenylphenoxy]aniline-bis(maleimide-benzoxazine) (pTPEQ-Bis(MI-BZ))

In a 50 mL of round-bottom flask equipped with a magnetic stir bar, N-(4-hydroxyphenyl)maleimide (1.3242 g, 0.0070 mol), 4-[4-(4-aminophenoxy)-3-phenylphenoxy] aniline (pTPEQ) (1.2895 g, 0.0035 mol), and paraformaldehyde (0.4204 g, 0.0140 mol) were placed, and then 1,4-dioxane and 2-methoxyehtanol (2:1 volume ratio) (11 mL) were added. After stirring for 30 min at ambient temperature, the solution was refluxed for 2-3 days while vigorously stirring. Once the solution was cooled down to room temperature, it was precipitated into hexane while stirring. After removal of solvent, the collected powder product was re-dissolved in tetrahydrofuran, and then it was re-precipitated into hexane. Finally, the desired product, pTPEQ-Bis(MI-BZ), was obtained after drying in vacuo overnight (Yield ~90%).

Example 10: Synthesis of 1,3-bis(4-aminophenoxy) benzene-bis(maleimide-benzoxazine) (RODA-Bis (MI-BZ))

In a 50 mL of round-bottom flask equipped with a magnetic stir bar, N-(4-hydroxyphenyl)maleimide (1.3242 g, 0.0070 mol), 1,3-bis(4-aminophenoxy) benzene (RODA) (1.0232 g, 0.0035 mol), and paraformaldehyde (0.4204 g, 0.0140 mol) were placed, and then 1,4-dioxane (11 mL) was added. After stirring for 30 min at ambient temperature, the solution was refluxed for 2-3 days while vigorously stirring. Once the solution was cooled down to room temperature, it was precipitated into hexane while stirring. After removal of solvent, the collected powder product was re-dissolved in ethyl acetate, and the solution was washed with 1N NaOH aqueous solution three times, followed by deionized water three times. Subsequently, the product in the organic layer was added dropwise into hexane for precipitation. Finally, the desired product, RODA-Bis(MI-BZ), was obtained after drying in vacuo overnight (Yield ~80%).

Film Molding for RODA-Bis(MI-BZ) (a Film of 100 μm in Thickness)

Two grades of thin films were made on a hot press using the following cure cycle: preheated press to 150° C.→placed sample and applied bumping (10 bumps) at 1 MPa after the sample was fully melted→ramped to 180° C. at 3° C./min→held for 50 min→ramped to 220° C. at 3° C./min→held for 56 min→ramped to 300° C. at 3° C./min→held for 60 min→cooled down to room temp at 3° C./min at 1 MPa pressure Film Molding for BAPP-Bis(MI-BZ) (a Film of 190 μm in Thickness)

A thin film was made on a hot press using the following cure cycle: preheated press to 160° C.→placed sample and applied bumping (10 bumps) at 1 MPa after the sample was fully melted→ramped to 220° C. at 5° C./min→held for 40 min→ramped to 290° C. at 5° C./min→held for 50 min→cooled down to room temp at 5° C./min at 1 MPa pressure Film Molding for pTPEQ-Bis(MI-BZ) (a Film of 195 μm in Thickness)

A thin film was made on a hot press using the following cure cycle: preheated press to 160° C.→placed sample and applied bumping (10 bumps) at 1 MPa after the sample was fully melted→ramped to 220° C. at 5° C./min→held for 40 min→ramped to 290° C. at 5° C./min→held for 50 min→cooled down to room temp at 5° C./min at 1 MPa pressure All of the benzoxazine resins synthesized herein were easily dissolved in common organic solvents, such as, acetone, chloroform, ethyl acetate, 1,4-dioxane, tetrahydrofuran, and N,N-dimethylformamide, demonstrating easy processability.

Figure 4:
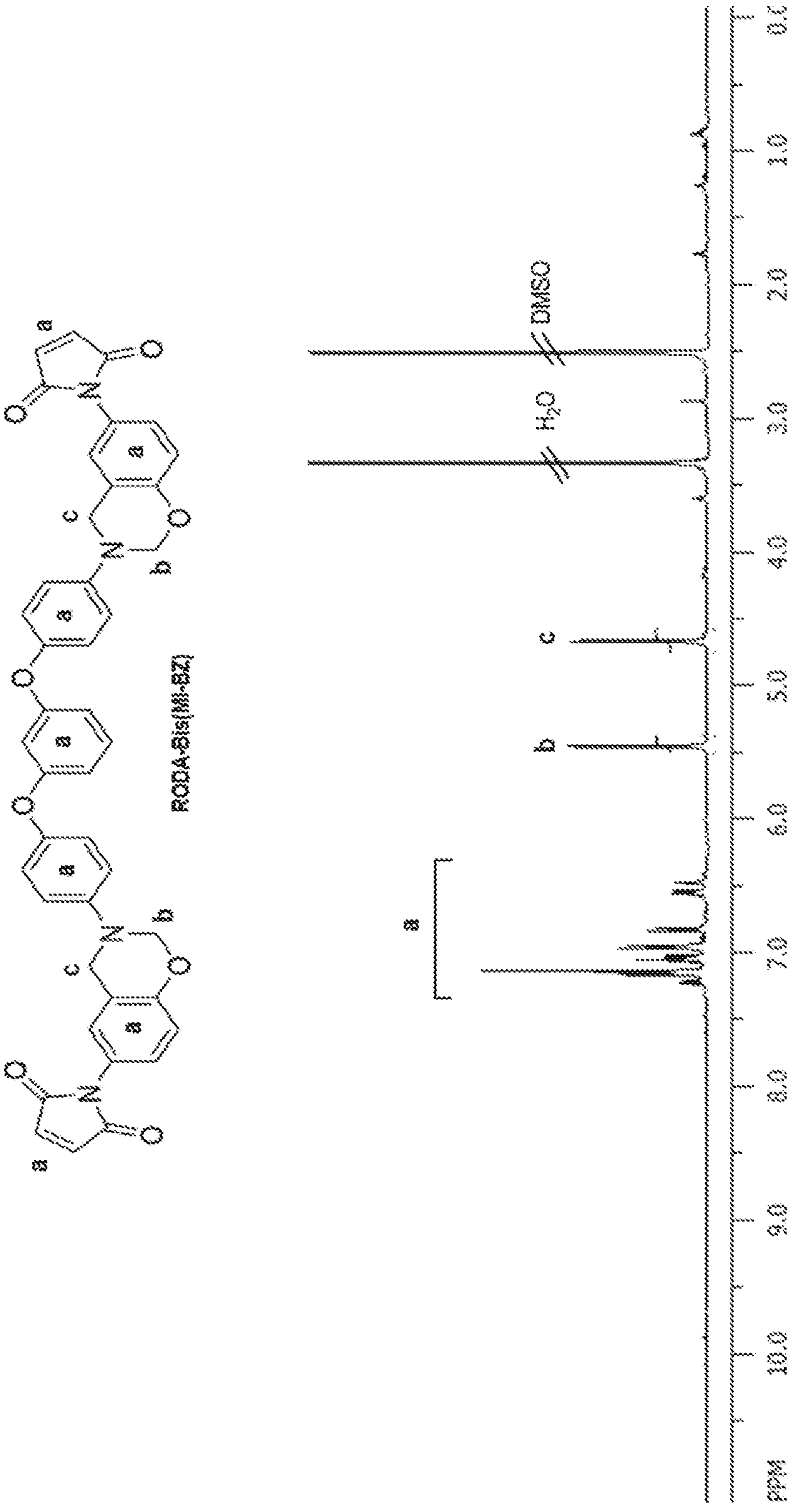
FIG. 4 shows 1H NMR spectra of RODA-Bis(MI-BZ).
Figure 5:
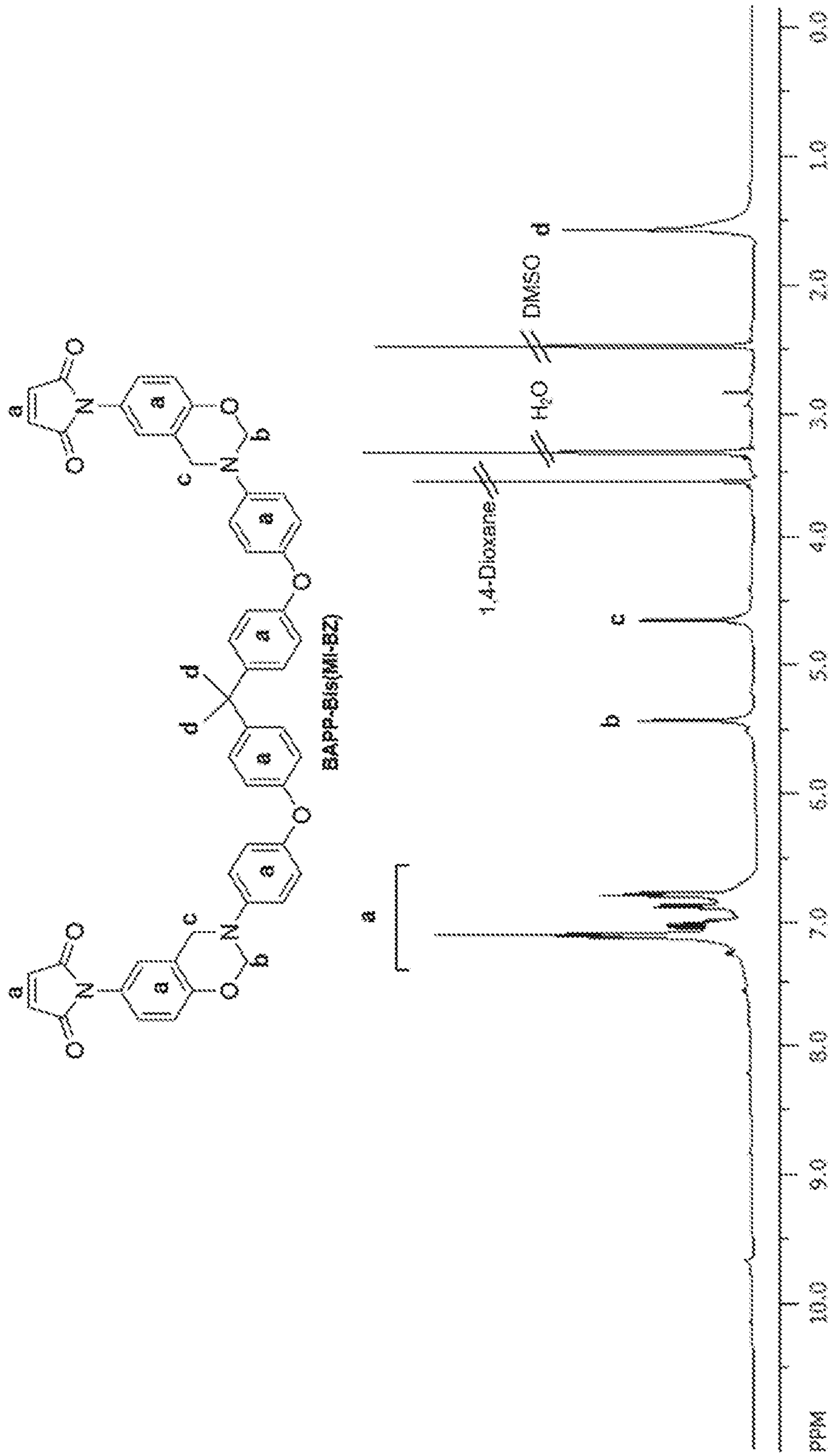
FIG. 5 shows 1H NMR spectra of BAPP-Bis(MI-BZ).
Figure 6:
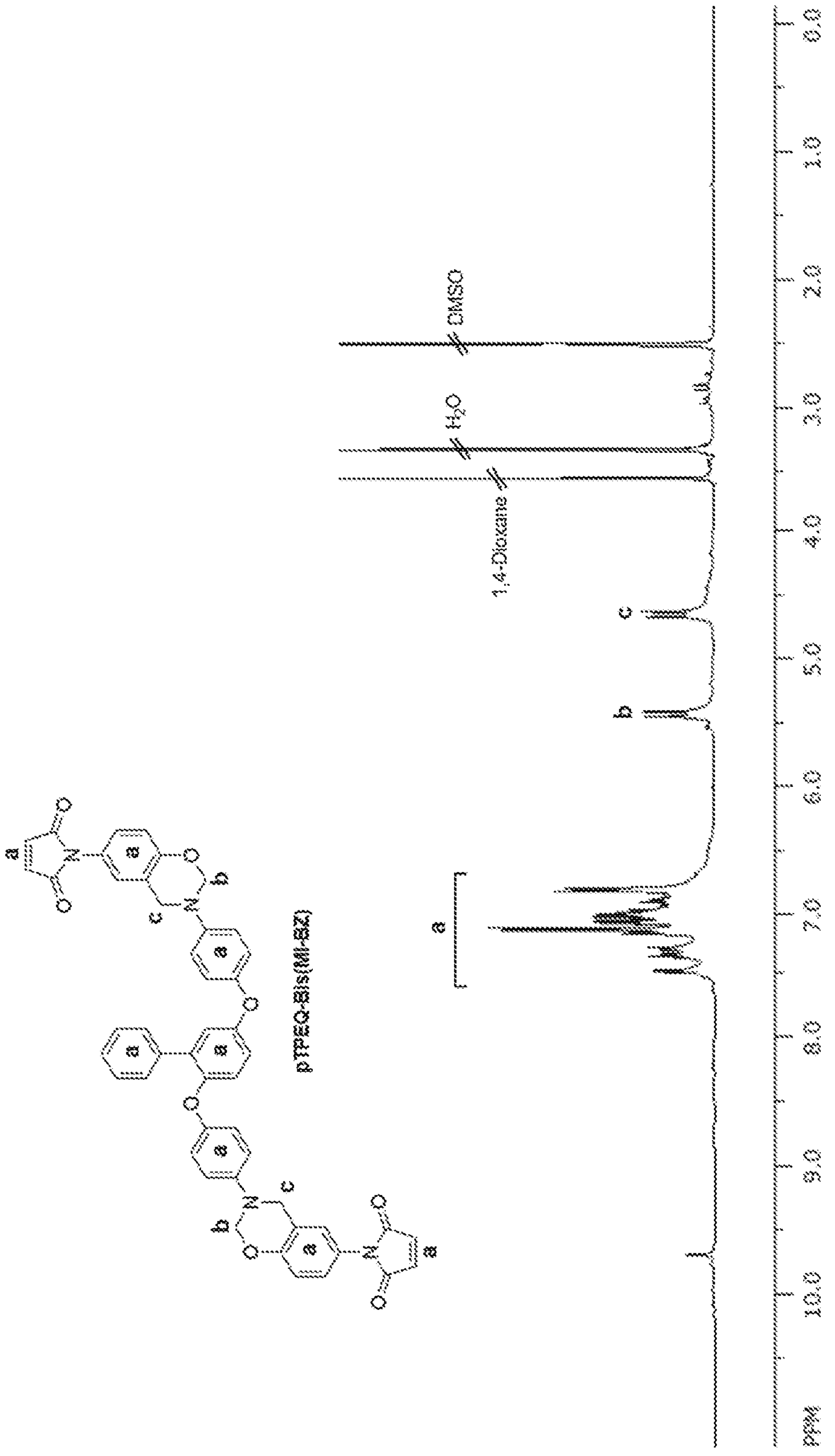
FIG. 6 shows 1H NMR spectra of pTPEQ-Bis(MI-BZ).

FIGS. 4, 5, and 6 show the $^1$H NMR spectra of the benzoxazine resins prepared in Examples 2, 5, and 8. The formation of benzoxazine ring via Mannich reaction was confirmed by the assignment of two resonance peaks at 4.7 and 5.5 ppm with equivalent integration ratio to $CH_2$ groups in the benzoxazine ring in the $^1$H NMR spectra. The residual unreacted phenolic starting material (i.e., HPMI) was occasionally observed in the $^{1}H$ NMR spectra. However, it is not anticipated to be detrimental to the properties of the resin and the cured resin, considering that the residual starting material may act as an additional crosslinker. Meanwhile, alkenyl proton resonance peaks from maleimide moieties overlapped with multiplets in the range of 6.3-7.5 ppm assigned to aromatic rings.

Figure 7:
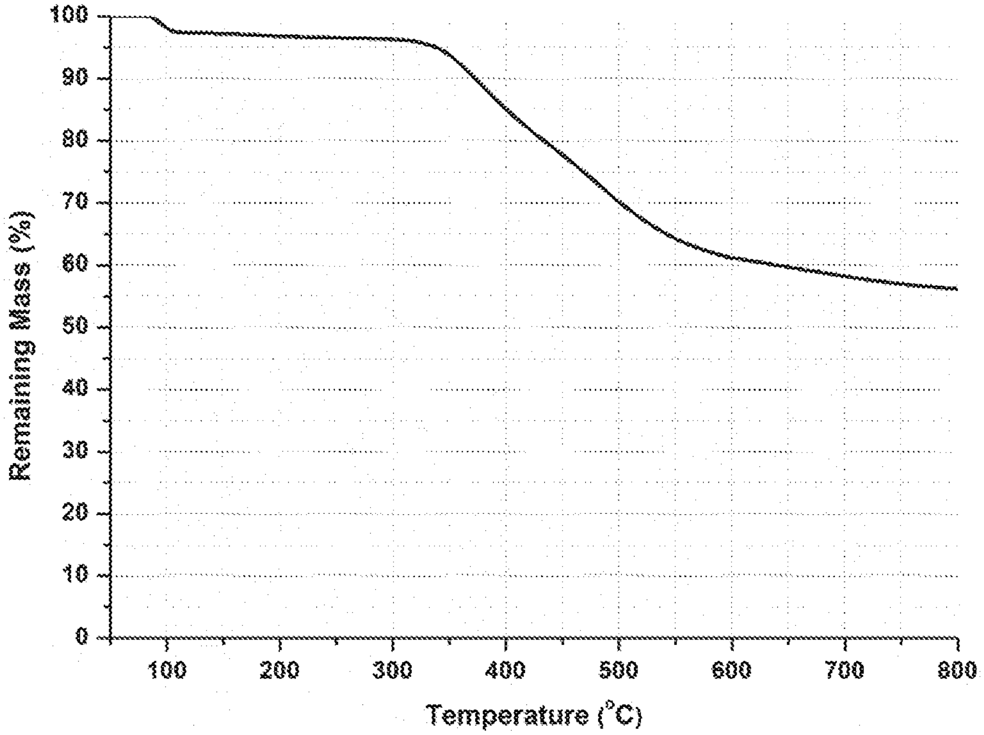
FIG. 7 shows TGA thermogram of RODA-Bis(MI-BZ).
Figure 8:
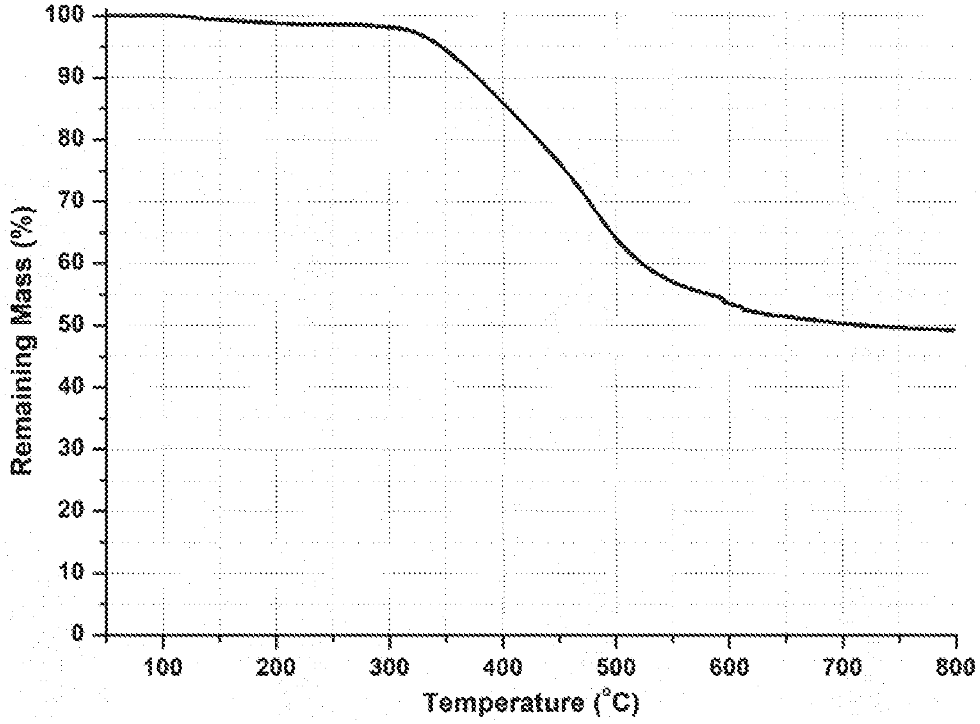
FIG. 8 shows TGA thermogram of BAPP-Bis(MI-BZ).
Figure 9:
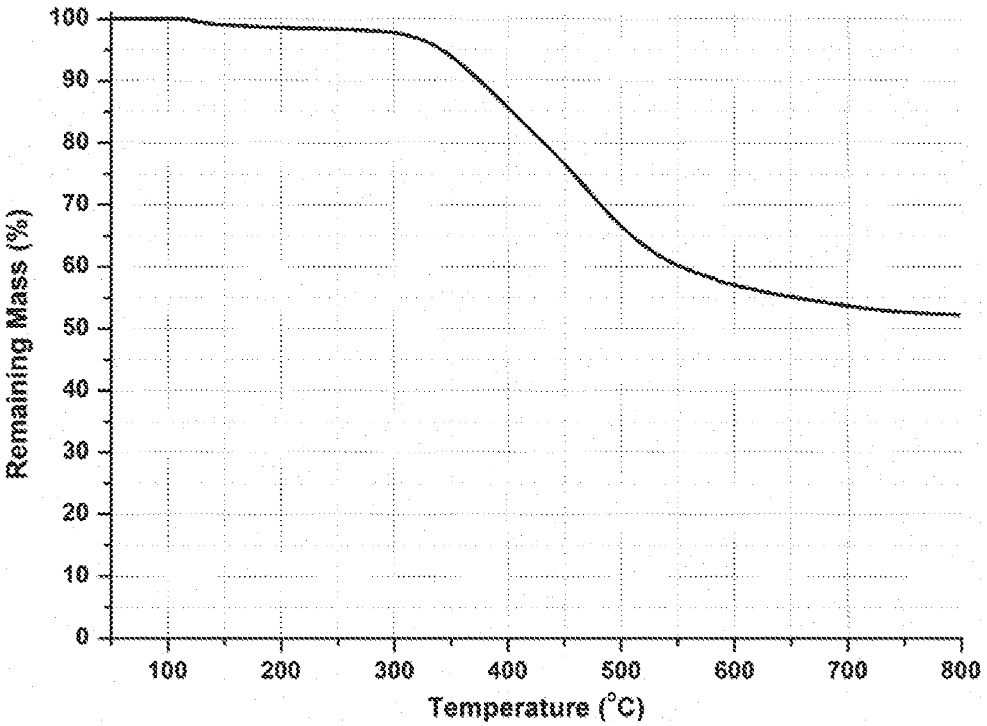
FIG. 9 shows TGA thermogram of pTPEQ-Bis(MI-BZ).

Thermal stability of the benzoxazine resins was determined by TGA, as shown in FIGS. 7-9. Table 1 summaries the TGA thermograms of the resins under $N_2$ atmosphere. The char yield illustrated in this disclosure indicates the remaining mass of the resin at 800° C. under $N_2$ atmosphere. Upon heating at 5° C./min on TGA, RODA-Bis(MI-BZ) showed 5% mass loss ($T_{d,5\%}$) at 362° C. and 10% mass loss ($T_{d,10\%}$) at 389° C. The char yield at 800° C. was 58%. BAPP-Bis(MI-BZ) displayed $T_{d,5\%}$ at 354° C., $T_{d,10\%}$ at 385° C., and 51% of char yield at 800° C. pTPEQ-Bis(MI-BZ) revealed $T_{d,5\%}$ at 345° C., $T_{d,10\%}$ at 383° C., and 54% of char yield at 800° C. In comparison, P-d, a commercial benzoxazine resin, was thermally less stable (i.e., $T_{d,5\%}$ at 343° C. and $T_{d,10\%}$ at 384° C.) than Examples 2, 5, and 8 while CYCOM® 4250, a commercial bismaleimide resin, was more stable ($T_{d,5\%}$ at 462° C. and $T_{d,10\%}$ at 474° C.) than Examples 2, 5, and 8. Meanwhile, char yields of P-d and CYCOM® 4250 at 800° C. were slightly lower than those of Examples 2, 5, and 8 (i.e., 49%).

TABLE 1

TGA ($T_{d,5\%}$, $T_{d,10\%}$, and char yield at 800° C.) of benzoxazine resins or bismaleimide resin

| | P-d | CYCOM ® 4250 (BMI) | RODA-Bis(MI-BZ) (Example 2) | BAPP-Bis(MI-BZ) (Example 5) | pTPEQ-Bis(MI-BZ) (Example 8) |
|---|---|---|---|---|---|
| $T_{d,5\%}$ (° C.) | 343 | 462 | 362 | 354 | 345 |
| $T_{d,10\%}$ (° C.) | 384 | 474 | 389 | 385 | 383 |
| Char yield at 800° C. | 49 | 49 | 58 | 51 | 54 |

Figure 10:
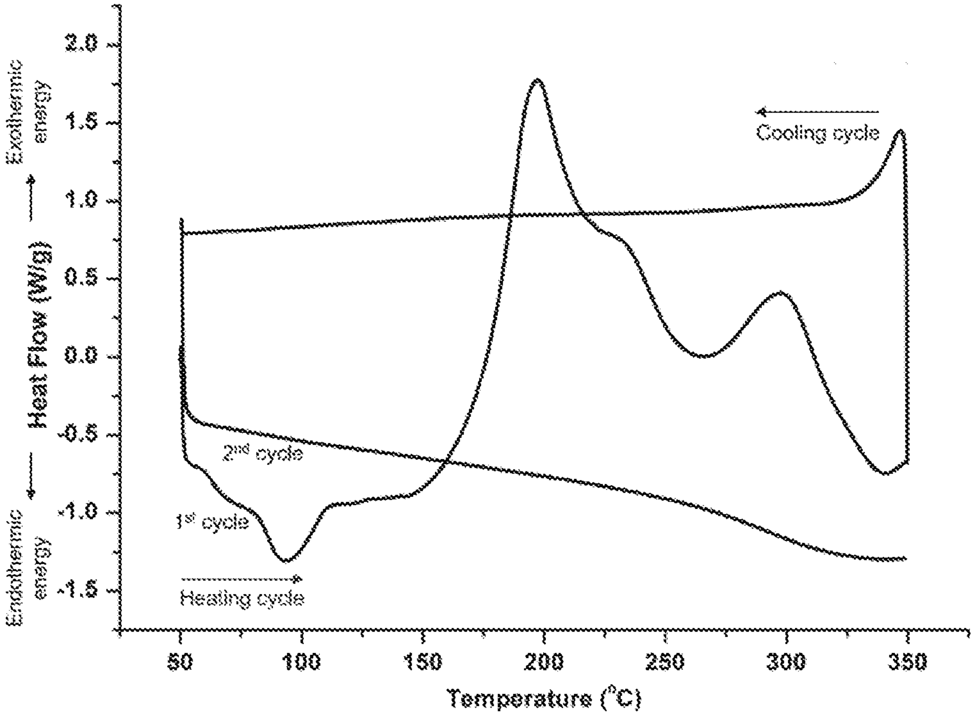
FIG. 10 shows DSC thermograms of RODA-Bis(MI-BZ).
Figure 11:
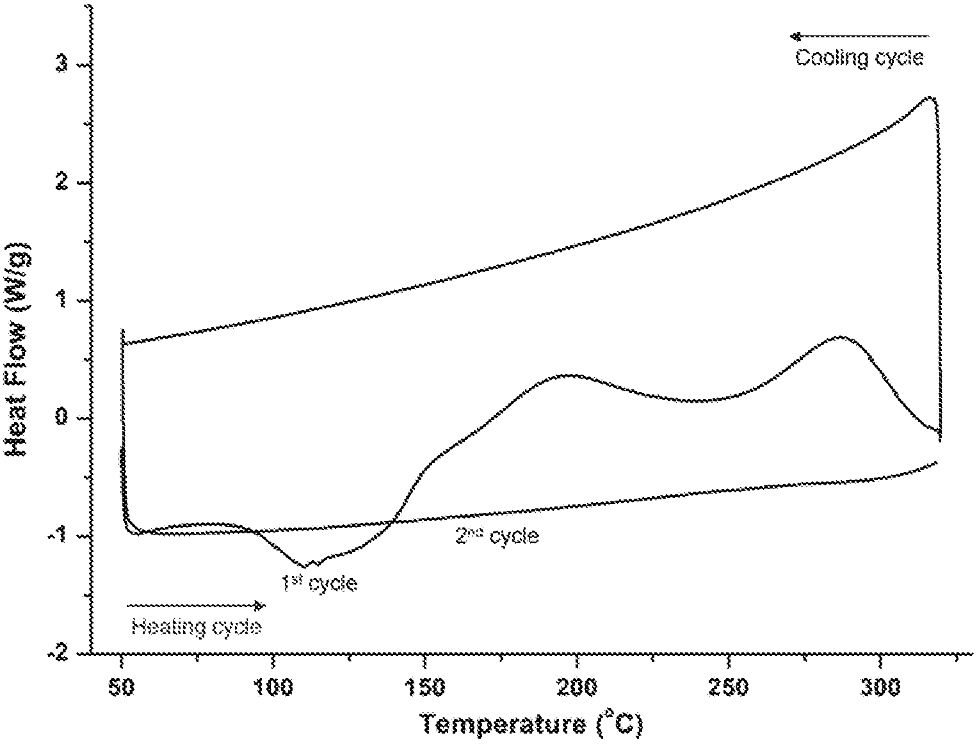
FIG. 11 shows DSC thermograms of BAPP-Bis(MI-BZ).
Figure 12:
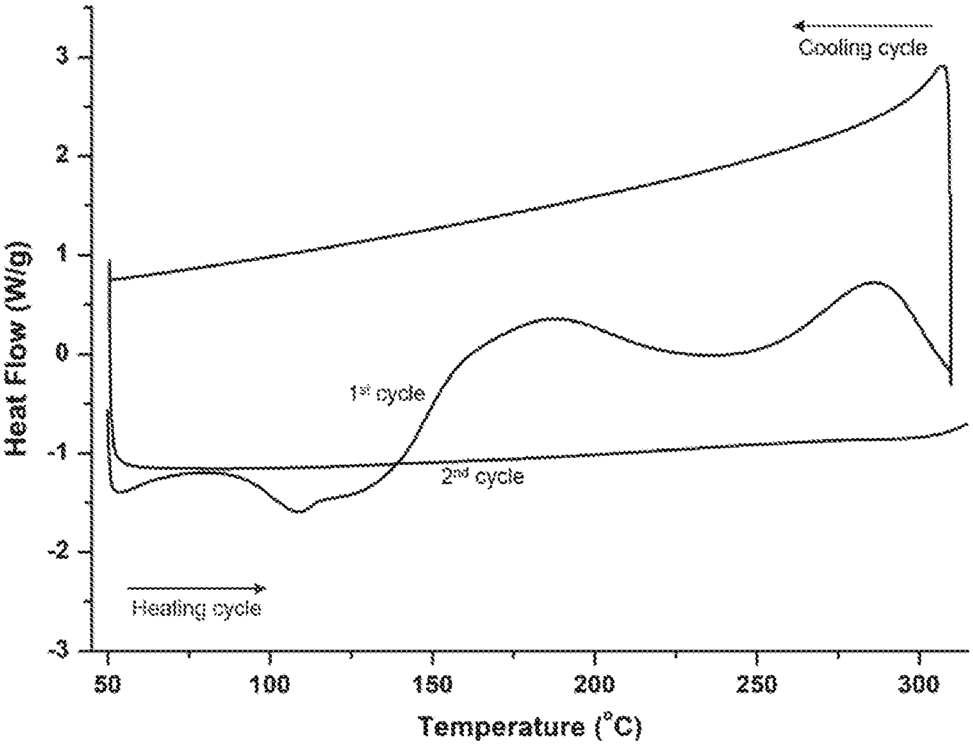
FIG. 12 shows DSC thermograms of pTPEQ-Bis(MI-BZ).

Thermal curing behavior of the benzoxazine resins and $T_g$ of the cured resins were investigated by DSC by heating at 5° C. per min, as shown in FIGS. 10-12. For RODA-Bis (MI-BZ), three exothermal curing peaks, having maximum peaks at 197, 230, and 298° C., were observed on the $1^{st}$ heating cycle. On the $2^{nd}$ heating cycle, $T_g$ of the cured resin appeared at 291° C. For BAPP-Bis(MI-BZ), while three exothermal peaks, with maximum peaks at 154, 195, and 288° C., were observed on the $1^{st}$ heating cycle, the first and the second peaks overlapped. On the $2^{nd}$ heating cycle, $T_g$ of the cured resin appeared at 280° C. For pTPEQ-Bis(MI-BZ), similarly, three exothermal peaks with maximum peaks at 156, 183, and 287° C. were found on the $1^{st}$ heating cycle, and the first and second exothermal peaks overlapped. On the $2^{nd}$ heating cycle, $T_g$ of the cured resin appeared at 273° C.

It is noteworthy that the benzoxazine resins containing pendant groups, such as, phenyl or alkyl group(s), and/or an asymmetric geometry within those pendant groups, could hinder the formation of aggregated structure of the resins, resulting in a decrease of onset curing temperatures. Indeed, onset temperatures of exothermal curing peaks of BAPP-Bis(MI-BZ) and pTPEQ-Bis(MI-BZ) were significantly lower than those of RODA-Bis(MI-BZ) and Bis(MI-DPDA), disclosed by Ishida et al. (Bis(benzoxazine-maleimide)s as a Novel Class of High Performance Resin: Synthesis and properties. *Eur. Polym. J.* 2010, 46, 354-363.) For example, for BAPP-Bis(MI-BZ), onset temperatures of the $1^{st}$ and $3^{rd}$ exothermal peaks were 125 and 240° C. For pTPEQ-Bis(MI-BZ), onset temperatures of the $1^{st}$ and the $3^{rd}$ exothermal peaks were 124 and 238° C. In comparison, those of RODA-Bis(MI-BZ) were 145 and 265° C., respectively, and those of Bis(MI-DPDA) were 194 and 280° C., respectively. Again, this decrease of onset temperatures of exothermal curing peaks of BAPP-Bis(MI-BZ) and pTPEQ-Bis(MI-BZ), was ascribed to the asymmetric structure of these resins in the existence of pendant phenyl or isopropyl group, which led to avoidance of the formation of aggregated structures.

Figure 13:
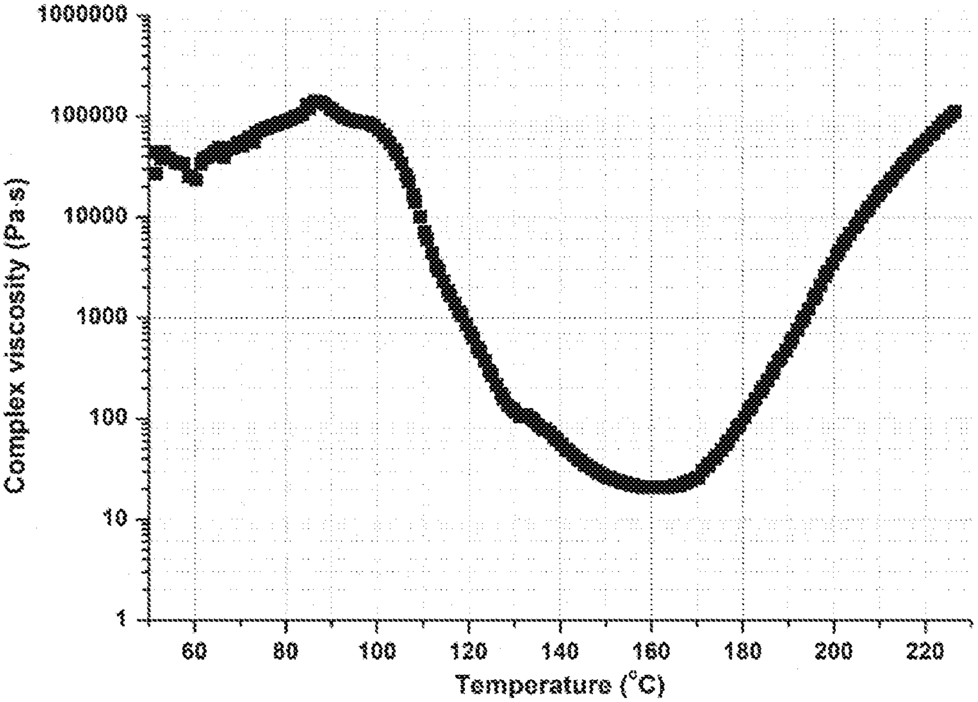
FIG. 13 shows a graph of complex viscosity of RODA-Bis(MI-BZ) as a function of temperature.
Figure 14:
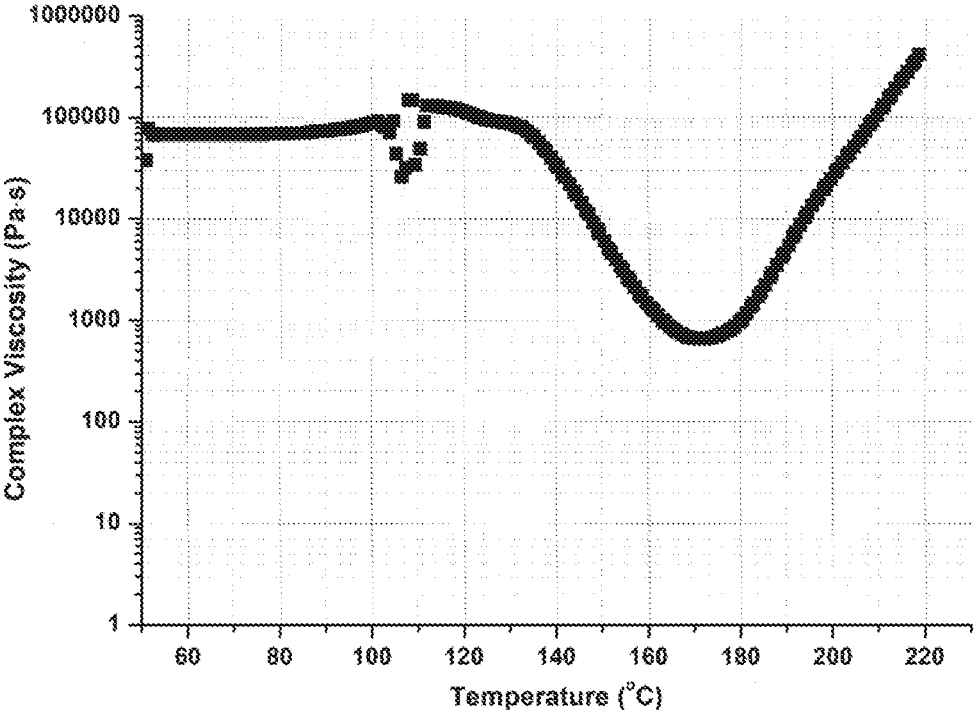
FIG. 14 shows a graph of complex viscosity of BAPP-Bis(MI-BZ) as a function of temperature.
Figure 15:
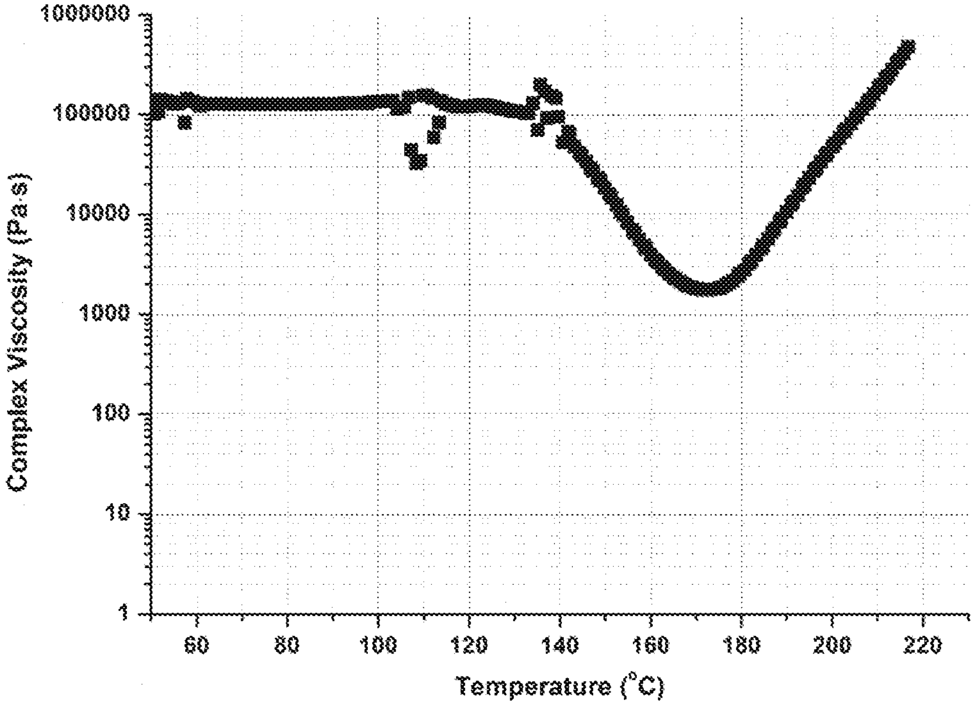
FIG. 15 shows a graph of complex viscosity of pTPEQ-Bis(MI-BZ) as a function of temperature.

The structural integration of benzoxazine and maleimide moieties into one chemical compound allowed for a low melt-viscosity of the benzoxazine resins to be achieved. The complex viscosities (or melt-viscosity) for the benzoxazine resins as a function of temperature are shown in FIGS. 13-15. For instance, in a particular embodiment, the complex viscosity of RODA-Bis(MI-BZ) could reach below 5000 Pa·s, a critical viscosity threshold for prepregging, in the temperature range of 112-202° C. and below 100 Pa·s, a critical viscosity threshold for pre-molding, in the temperature range of 133-180° C. The complex viscosity values of BAPP-Bis(MI-BA) and pTPEQ-Bis(MI-BZ) were relatively higher than those of RODA-Bis(MI-BZ). The temperature ranges of 152-190° C. and 158-185° C. were required to reach below 5000 Pa·s for BAPP-Bis(MI-BZ) and pTPEQ-Bis(MI-BZ), respectively.

It is important to note that onset melting temperature of RODA-Bis(MI-BZ) (100° C.), was significantly lower than that of BAPP-Bis(MI-BZ) (135° C.), and pTPEQ-Bis(MI-BZ) (140° C.). Also, the minimum complex viscosity of RODA-Bis(MI-BZ) (20 Pa s at 161° C.) turned out to be lower than that of BAPP-Bis(MI-BZ) (660 Pa·s at 171° C.) and pTPEQ-Bis(MI-BZ) (1757 Pa·s at 173° C.). These two phenomena—that is, both the lower onset melting temperature and the lower minimum complex viscosity of RODA-Bis(MI-BZ) (as compared with BAPP-Bis(MI-BZ) and pTPEQ-Bis(MI-BZ)) were attributed to the delayed onset curing temperature of the $1^{st}$ exothermal peak at 145° C.

Figure 16:
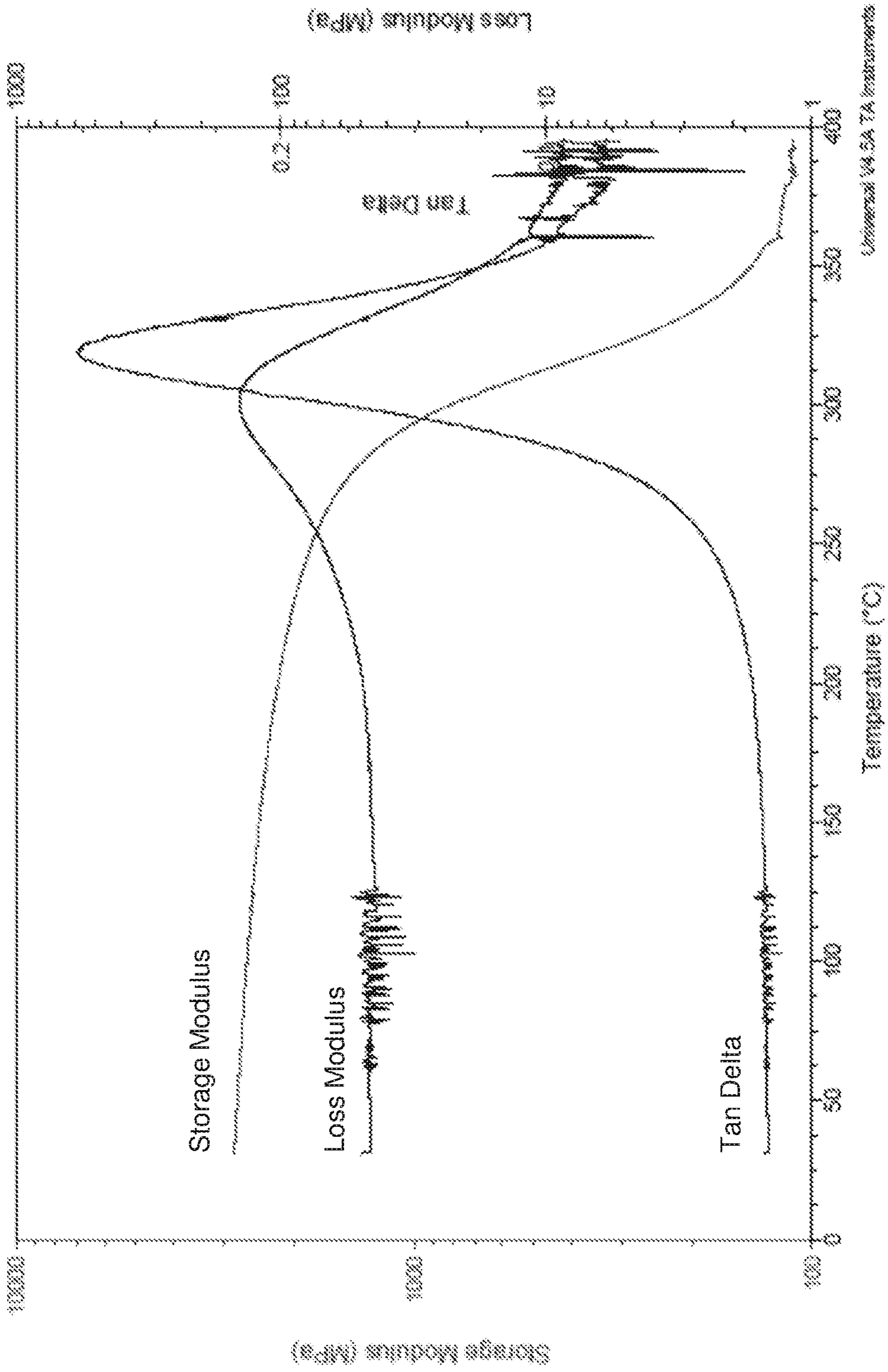
FIG. 16 shows a graph of storage modulus (MPa) and loss modulus (MPa) of RODA-Bis(MI-BZ) as a function of temperature.
Figure 19:
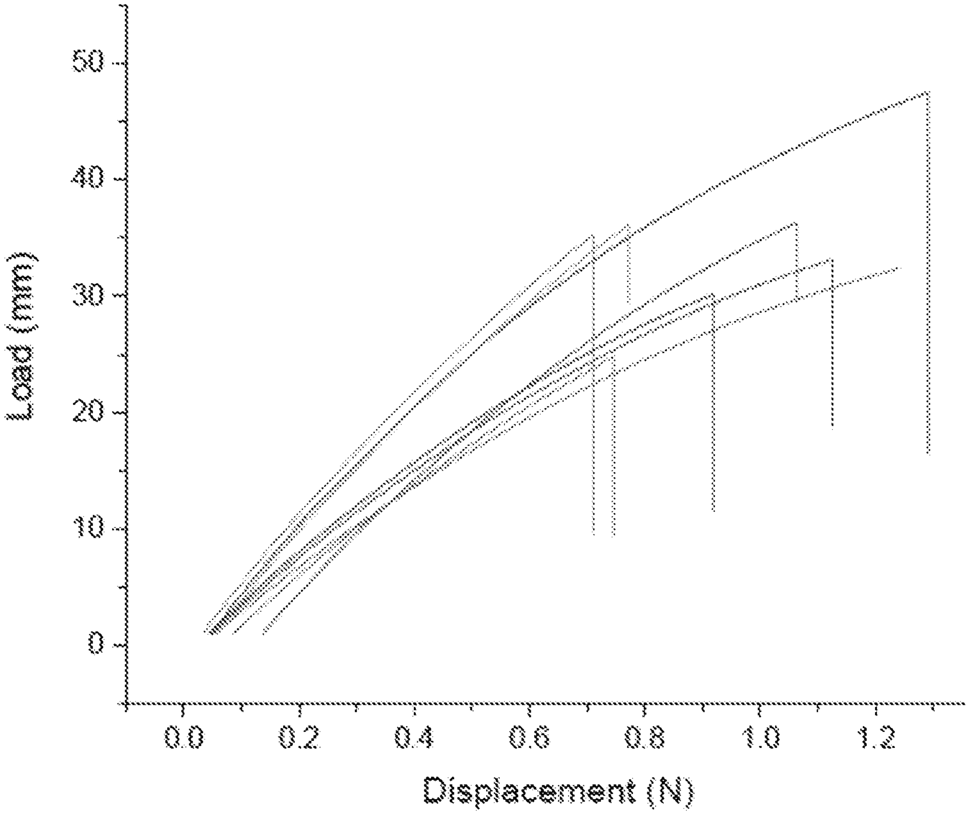
FIG. 19 shows stress-strain curves from a tensile test of RODA-Bis(MI-BZ).

Subsequently, RODA-Bis(MI-BZ) was molded into a thin film of 100 μm in thickness. DMA indicated $T_g$ of the molded film of the resin to be at 268° C. (FIG. 16). According to the tensile test results, the prepared molded film displayed 98±13 MPa of strength, 3.6±0.19 GPa of modulus, and 5.0±1.1% of elongation, which was unusually higher than elongation % of typical thermoset composite (i.e., 1-2%) (FIG. 19 and Table 2).

Figure 17:
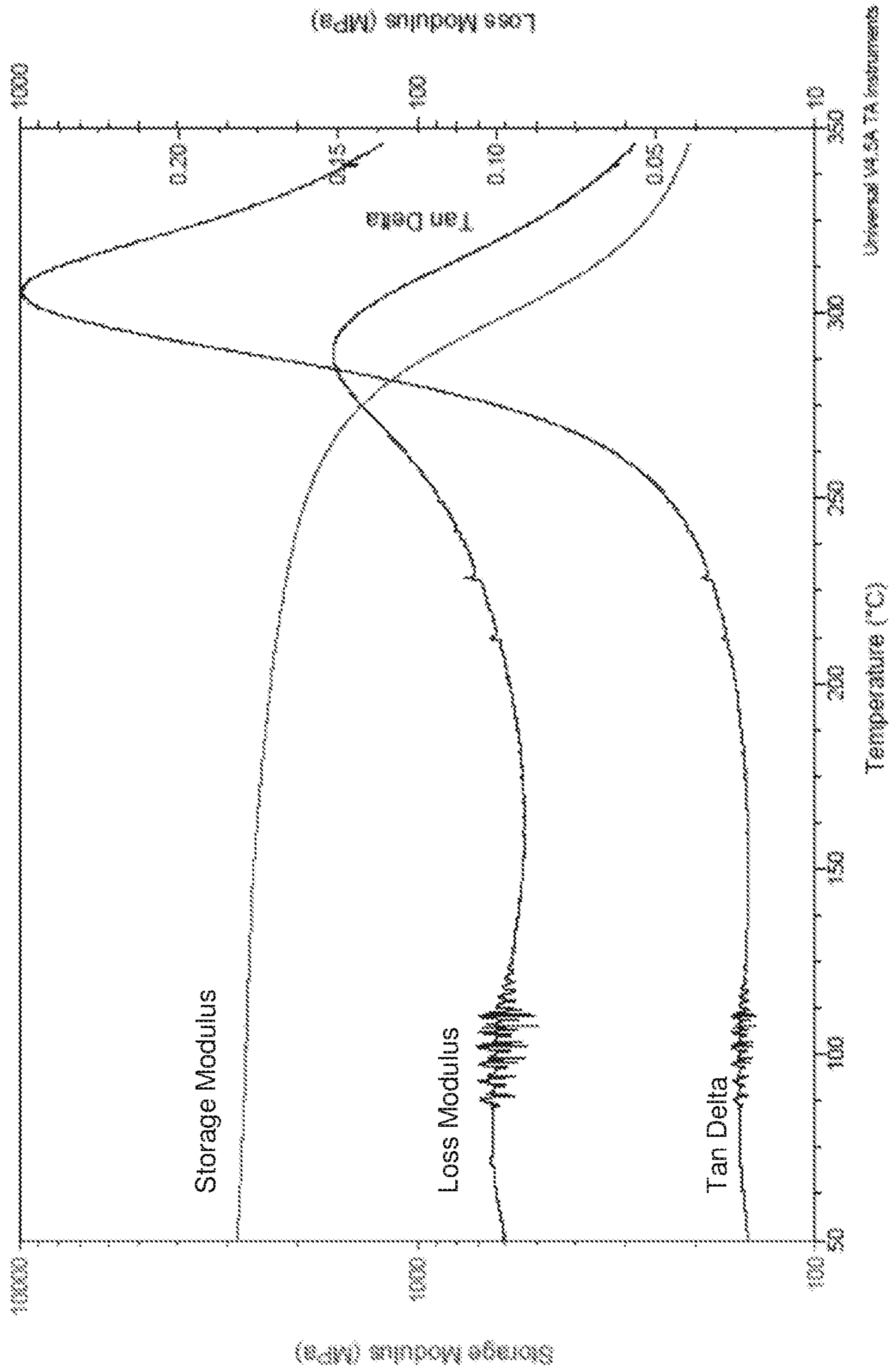
FIG. 17 shows a graph of storage modulus (MPa) and loss modulus (MPa) of BAPP-Bis(MI-BZ) as a function of temperature.
Figure 18:
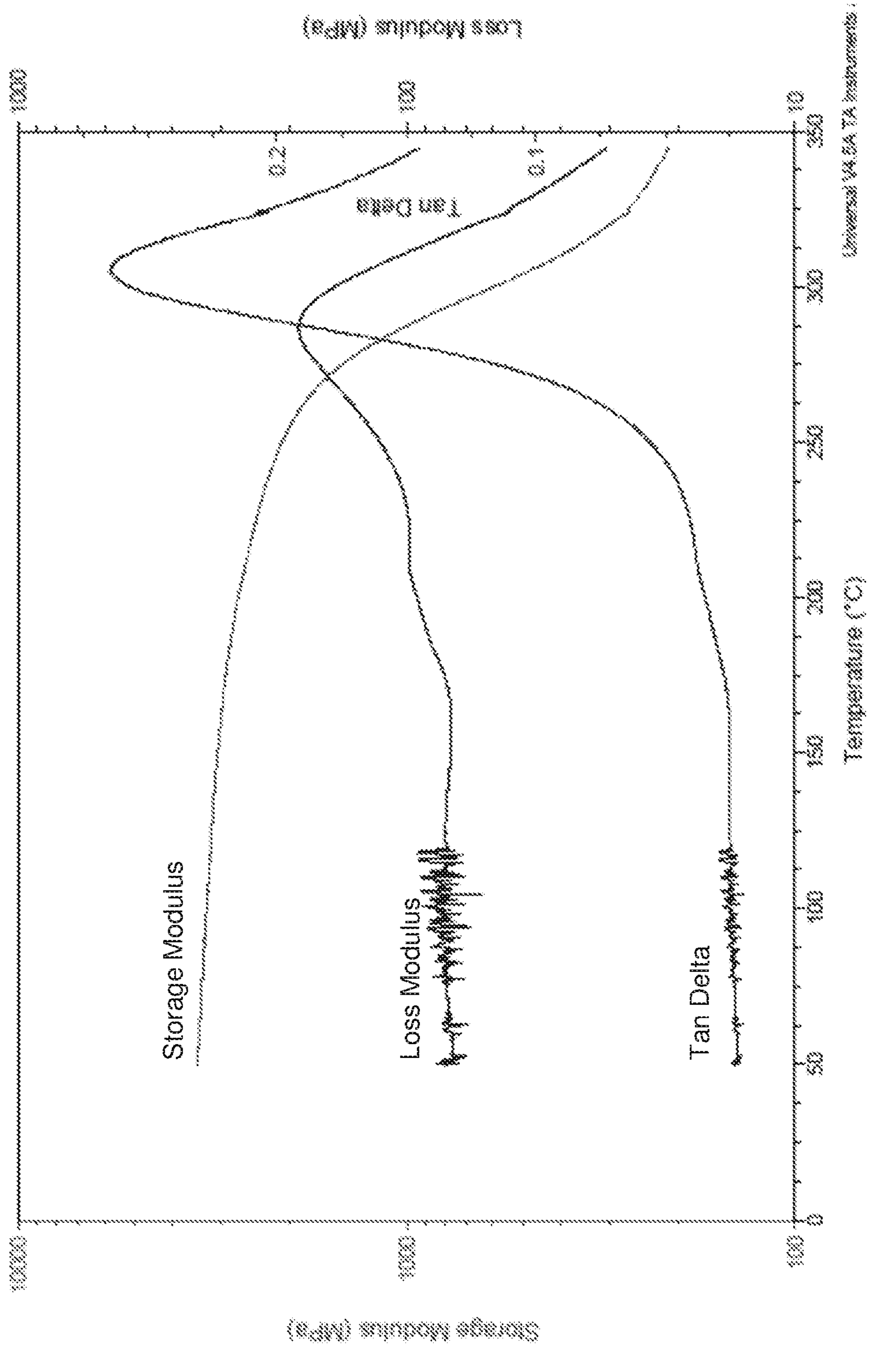
FIG. 18 shows a graph of storage modulus (MPa) and loss modulus (MPa) of pTPEQ-Bis(MI-BZ) as a function of temperature.
Figure 20:
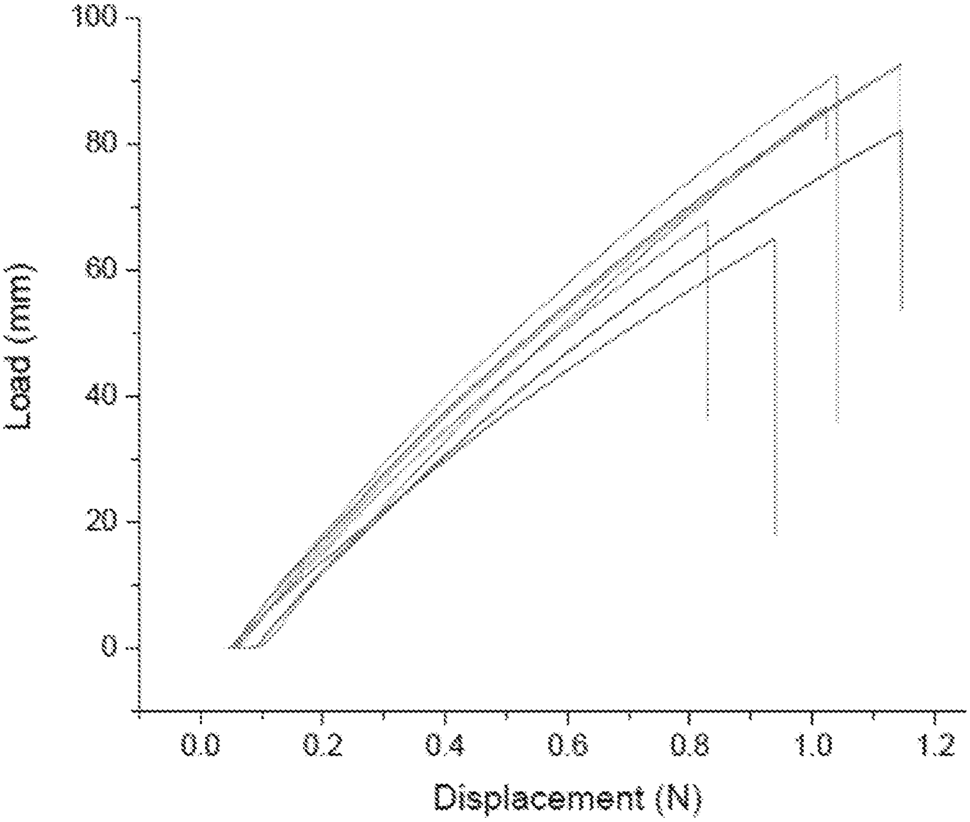
FIG. 20 shows stress-strain curves from a tensile test of BAPP-Bis(MI-BZ).
Figure 21:
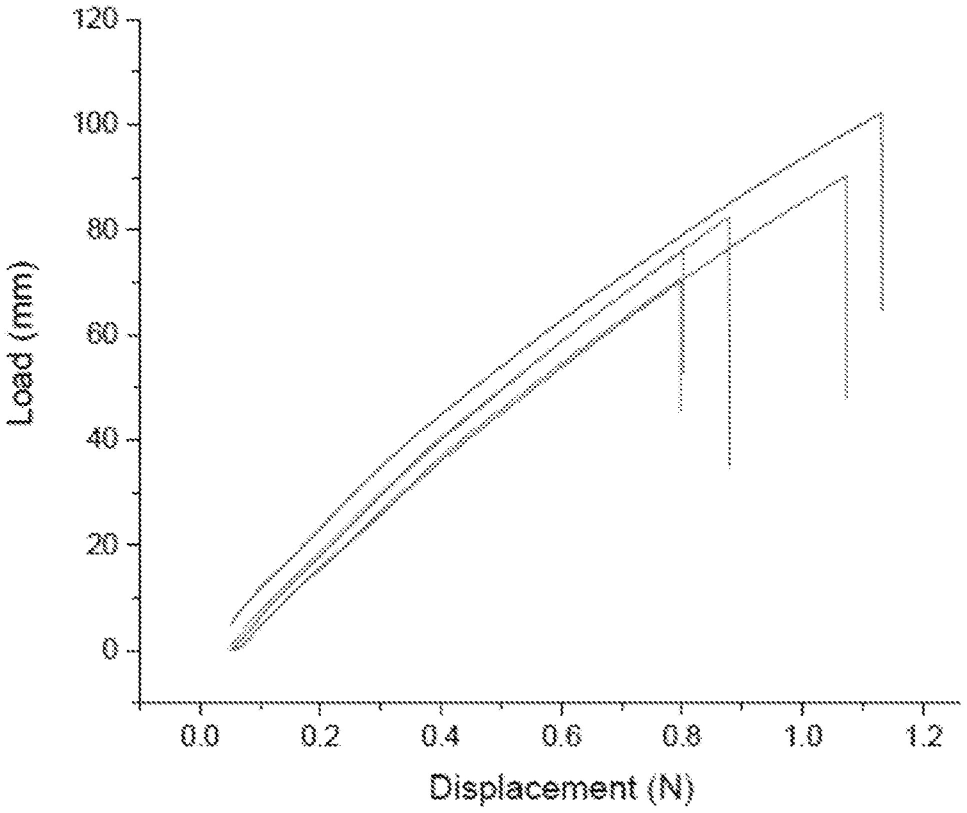
FIG. 21 shows stress-strain curves from the tensile test of pTPEQ-Bis(MI-BZ).

BAPP-Bis(MI-BZ) was molded into a thin film of 190 μm in thickness. DMA indicated $T_{g,onset}$ of the molded film of the resin to be at 273° C. (FIG. 17). According to the tensile test results, the prepared molded film displayed 83±7.0 MPa of strength, 3.0±0.12 GPa of modulus, and 3.9±0.42% of elongation, which was also unusually higher than elongation % of typical thermoset composite (i.e., 1-2%) (FIG. 20 and Table 2).

pTPEQ-Bis(MI-BZ) was molded into a thin film of 195 μm in thickness by molding. DMA indicated $T_{g,onset}$ of the molded film of pTPEQ-Bis(MI-BZ) to be at 269° C. (FIG. 18). According to the tensile test results, the prepared molded film displayed 77±5.9 MPa of strength, 3.2±0.14 GPa of modulus, and 3.6±0.67% of elongation, which was also unusually higher than elongation % of typical thermoset composite (i.e., 1-2%) (FIG. 21 and Table 2).

The aforementioned properties are summarized in Table 2 below:

TABLE 2

Thermal and mechanical properties of benzoxazine resins

| Property | | CYCOM ® 4250 (BMI) | P-d | Bis(MI-DPDA) | RODA-Bis(MI-BZ) | BAPP-Bis(MI-BZ) | pTPEQ-Bis(MI-BZ) |
|---|---|---|---|---|---|---|---|
| Onset temp. of 1st and 3rd exothermal peaks (° C.) | | 163 (BMI-1000) | 200 | 194 (1st) 280 (3nd) | 145 (1st) 265 (3rd) | 125 (1st) 240 (3rd) | 238 (3rd) |
| Dry $T_g$ (° C.) | | 300 | 187 | N/A | 268 | 273 | 269 |
| Tensile properties | Strength (MPa) | 103 | 82 ± 6.5 | N/A | 98 ± 13 | 83 ± 7.0 | 77 ± 5.9 |
| | Modulus (GPa) | 4.6 | 3.1 ± 0.2 | N/A | 3.6 ± 0.19 | 3.0 ± 0.12 | 3.2 ± 0.14 |
| | Strain (%) | 4.8 | 3.2 ± 0.4 | N/A | 5.0 ± 1.1 | 3.9 ± 0.42 | 3.6 ± 0.67 |
| Viscosity profile (° C.) | @5000 Pa · s | N/A | 80-222 | N/A | 112-202 | 152-190 | 158-185 |
| | @100 Pa · s | 78-183 | 88-218 | N/A | 133-180 | N/A | N/A |

Example 10: Synthesis of N-(4-hydroxyphenyl)citraconic amic acid (HPCAA)

In a 500 mL 3-necked flask equipped with a magnetic stir bar and a reflux condenser, citraconic anhydride (26.9000 g, 0.2400 mol) was dissolved in acetone (270 mL). The solution was stirred at ambient temperature, and 4-aminophenol (26.7200 g, 0.2448 mol) was added in portions over 30 min. The reaction solution turned into a yellow slurry. After stirring for additional 30 min, the slurry was filtered. The solid was washed with cold acetone, and then, dried in vacuo overnight to give a yellow powder product (Yield ~95%)

Example 11: Synthesis of N-(4-hydroxyphenyl)citraconic imide (HPCI)

HPCAA (24.9970 g, 0.1130 mol) was dispersed in a 250 mL round bottom flask containing toluene (100 mL). p-toluene sulfonic acid (1.9460 g, 0.0113 mol,) and DMF (11.3 mL) were added into the reaction mixture, and the mixture solution was refluxed for 5 h. After cooling the solution to room temperature, the solution was poured into large quantities of crushed ice. The slurry was filtered, washed with ice cold water, and dried in vacuo at elevated temperature overnight (Yield ~70%).

Figure 22A:
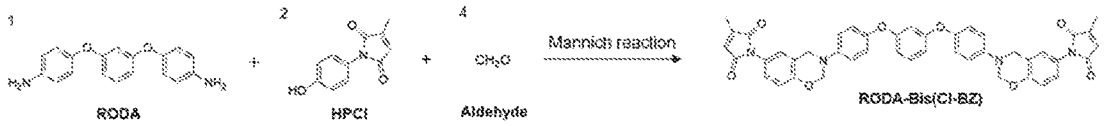
FIG. 22A shows the reaction scheme for the formation of RODA-Bis(CI-BZ) in accordance with one or more embodiments of the present disclosure.

Example 12: Synthesis of 1,3-bis(4-aminophenoxy) benzene-bis(citraconic imide-benzoxazine) (RODA-Bis(CI-BZ)) Shown in FIG. 22A In a 150 mL of round-bottom flask equipped with a magnetic stir bar, HPCI (5.4864 g, 0.0270 mol), RODA (3.9466 g, 0.0135 mol), and paraformaldehyde (1.6216 g, 0.0540 mol) were placed, and then, 1,4-dioxane (40 mL) was added. After stirring for 30 min at ambient temperature, the solution was refluxed for 2 days while vigorously stirring. Once the solution was cooled down to room temperature, it was precipitated into hexane while stirring. Finally, the desired product, RODA-Bis(CI-BZ), was obtained after drying in vacuo overnight (Yield ~90%).

Figure 22B:
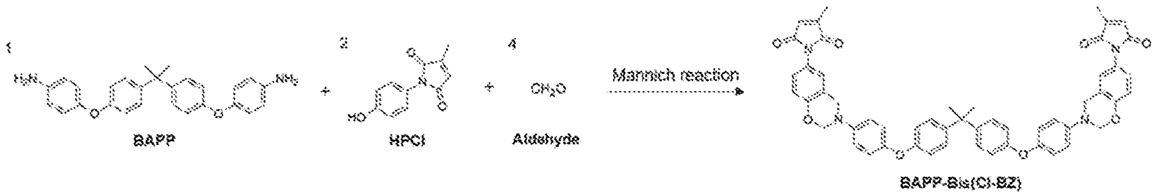
FIG. 22B shows the reaction scheme for the formation of BAPP-Bis(CI-BZ) in accordance with one or more embodiments of the present disclosure.

Example 13: Synthesis of 2,2-bis[4-(4-aminophenoxy)phenyl]propane-bis(citraconic imide-benzoxazine) (BAPP-Bis(CI-BZ)) Shown in FIG. 22B In a 150 mL of round-bottom flask equipped with a magnetic stir bar, HPCI (5.2832 g, 0.0260 mol), BAPP (5.3368 g, 0.0130 mol), and paraformaldehyde (1.5616 g, 0.0520 mol) were placed, and then, 1,4-dioxane (40 mL) was added. After stirring for 30 min at ambient temperature, the solution was refluxed for 2 days while vigorously stirring. Once the solution was cooled down to room temperature, it was precipitated into hexane while stirring. Finally, the desired product, BAPP-Bis(CI-BZ), was obtained after drying in vacuo overnight (Yield ~90%).

Figure 22C:
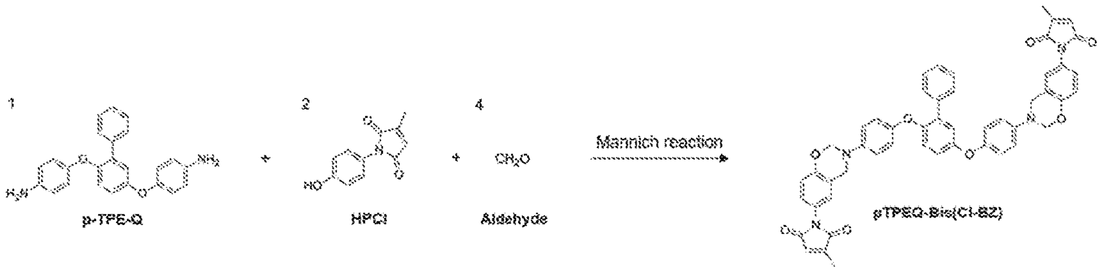
FIG. 22C shows the reaction scheme for the formation of pTPEQ-Bis(CI-BZ) in accordance with one or more embodiments of the present disclosure.

Example 14: Synthesis of 4-[4-(4-aminophenoxy)-3-phenylphenoxy]aniline-bis(citraconic imide-benzoxazine) (pTPEQ-Bis(CI-BZ)) Shown in FIG. 22C In a 150 mL of round-bottom flask equipped with a magnetic stir bar, HPCI (5.4864 g, 0.0270 mol), p-TEP-Q (4.9739 g, 0.0135 mol), and paraformaldehyde (1.6216 g, 0.0540 mol) were placed, and then, 1,4-dioxane (40 mL) was added. After stirring for 30 min at ambient temperature, the solution was refluxed for 2 days while vigorously stirring. Once the solution was cooled down to room temperature, it was precipitated into hexane while stirring. Finally, the desired product, pTPEQ-Bis(CI-BZ), was obtained after drying in vacuo overnight (Yield ~90%).

Figure 23A:
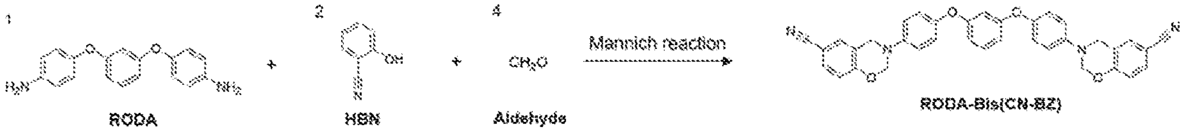
FIG. 23A shows the reaction schemes for the formation of RODA-Bis(CN-BZ) in accordance with one or more embodiments of the present disclosure.

Example 15: Synthesis of 1,3-bis(4-aminophenoxy) benzene-bis(nitrile-benzoxazine) (RODA-Bis(CN-BZ)) Shown in FIG. 23A In a 250 mL of round-bottom flask equipped with a magnetic stir bar, 2-HBN (8.3384 g, 0.0700 mol), RODA (10.2319 g, 0.0350 mol), and paraformaldehyde (4.2042 g, 0.1400 mol) were placed, and then, 1,4-dioxane (105 mL) was added. After stirring for 30 min at ambient temperature, the solution was refluxed for 2 days while vigorously stirring. Once the solution was cooled down to room temperature, it was precipitated into hexane while stirring. Finally, the desired product, RODA-Bis(CN-BZ), was obtained after drying in vacuo overnight (Yield ~90%).

Figure 23B:
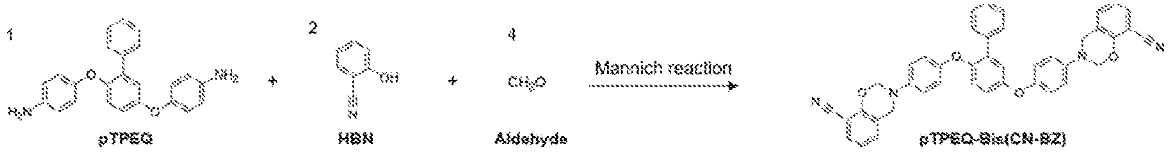
FIG. 23B shows the reaction schemes for the formation of pTPEQ-Bis(CN-BZ) in accordance with one or more embodiments of the present disclosure.

Example 16: Synthesis of 4-[4-(4-aminophenoxy)-3-phenylphenoxy]aniline-bis(nitrile-benzoxazine) (pTPEQ-Bis(CN-BZ)) Shown in FIG. 23B In a 250 mL of round-bottom flask equipped with a magnetic stir bar, 2-HBN (8.3384 g, 0.0700 mol), p-TEP-Q (12.8954 g, 0.0350 mol), and paraformaldehyde (4.2042 g, 0.1400 mol) were placed, and then, 1,4-dioxane (105 mL)

was added. After stirring for 30 min at ambient temperature, the solution was refluxed for 2 days while vigorously stirring. Once the solution was cooled down to room temperature, it was precipitated into hexane while stirring. Finally, the desired product, pTPEQ-Bis(CN-BZ), was obtained after drying in vacuo overnight (Yield ~90%).

Figure 23C:
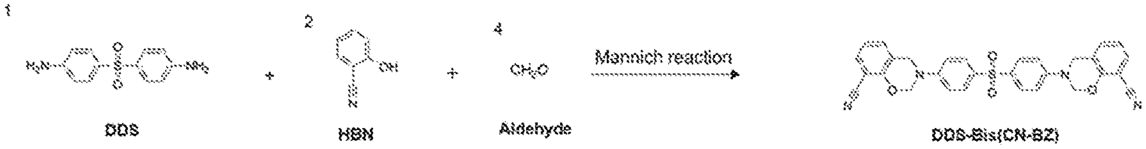
FIG. 23C shows the reaction schemes for the formation of DDS-Bis(CN-BZ) in accordance with one or more embodiments of the present disclosure.

Example 17: Synthesis of 4,4'-diaminodiphenyl sulfone-bis(nitrile-benzoxazine) (DDS-Bis(CN-BZ)) Shown in FIG. 23C In a 150 mL of round-bottom flask equipped with a magnetic stir bar, 2-HBN (5.4795 g, 0.0460 mol), DDS (5.7109 g, 0.0230 mol), and paraformaldehyde (2.7628 g, 0.0920 mol) were placed, and then, a mixture of 1,4-dioxane (47 mL) and 2-methoxyehtanol (23 mL) was added. After stirring for 30 min at ambient temperature, the solution was refluxed for 2 days while vigorously stirring. Once the solution was cooled down to room temperature, solvents were removed in vacuo. After dissolving in THF, it was precipitated into hexane while stirring. Finally, the desired product, DDS-Bis(CN-BZ), was obtained after drying in vacuo overnight (Yield ~90%).

Film Molding for RODA-Bis(CI-BZ) (a Film of 170 μm in Thickness)

A thin film was made on a hot press using the following cure cycle: preheated press to 160° C.→placed sample and applied bumping (10 bumps) at 1 MPa after the sample was fully melted→ramped to 220° C. at 5° C./min→held for 40 min→ramped to 270° C. at 5° C./min→held for 60 min→cooled down to room temp at 5° C./min at 1 MPa pressure Film Molding for BAPP-Bis(CI-BZ) (a Film of 180 μm in Thickness)

A thin film was made on a hot press using the following cure cycle: preheated press to 160° C.→placed sample and applied bumping (10 bumps) at 1 MPa after the sample was fully melted→ramped to 220° C. at 5° C./min→held for 40 min→ramped to 270° C. at 5° C./min→held for 60 min→cooled down to room temp at 5° C./min at 1 MPa pressure Film Molding for pTPEQ-Bis(CI-BZ) (a Film of 160 μm in Thickness)

A thin film was made on a hot press using the following cure cycle: preheated press to 160° C.→placed sample and applied bumping (10 bumps) at 1 MPa after the sample was fully melted→ramped to 220° C. at 5° C./min→held for 40 min→ramped to 270° C. at 5° C./min→held for 60 min→cooled down to room temp at 5° C./min at 1 MPa pressure Film Molding for RODA-Bis(CN-BZ) (a Film of 200 μm in Thickness)

A thin film was made on a hot press using the following cure cycle: preheated press to 160° C.→placed sample and applied bumping (10 bumps) at 1 MPa after the sample was fully melted→ramped to 220° C. at 5° C./min→held for 40 min→ramped to 270° C. at 5° C./min→held for 60 min→cooled down to room temp at 5° C./min at 1 MPa pressure Film Molding for pTPEQ-Bis(CN-BZ) (a Film of 190 μm in Thickness)

A thin film was made on a hot press using the following cure cycle: preheated press to 160° C.→placed sample and applied bumping (10 bumps) at 1 MPa after the sample was fully melted→ramped to 220° C. at 5° C./min→held for 40 min→ramped to 270° C. at 5° C./min→held for 60 min→cooled down to room temp at 5° C./min at 1 MPa pressure Film Molding for DDS-Bis(CN-BZ)

A thin film was made on a hot press using the following cure cycle: preheated press to 160° C.→placed sample and applied bumping (10 bumps) at 1 MPa after the sample was fully melted→ramped to 220° C. at 5° C./min→held for 40 min→ramped to 290° C. at 5° C./min→held for 60 min→cooled down to room temp at 5° C./min at 1 MPa pressure All of the benzoxazine resins synthesized herein were easily dissolved in common organic solvents, such as, acetone, chloroform, ethyl acetate, 1,4-dioxane, tetrahydrofuran, N-methyl-2-pyrrolidone, dimethylacetamide, and N,N-dimethylformamide, demonstrating easy processability.

N-(4-hydroxyphenyl)citraconic imide (HPCI) was synthesized by condensation followed by ring-closing reaction, using citraconic anhydride and 4-aminophenol as starting materials.

Figure 24:
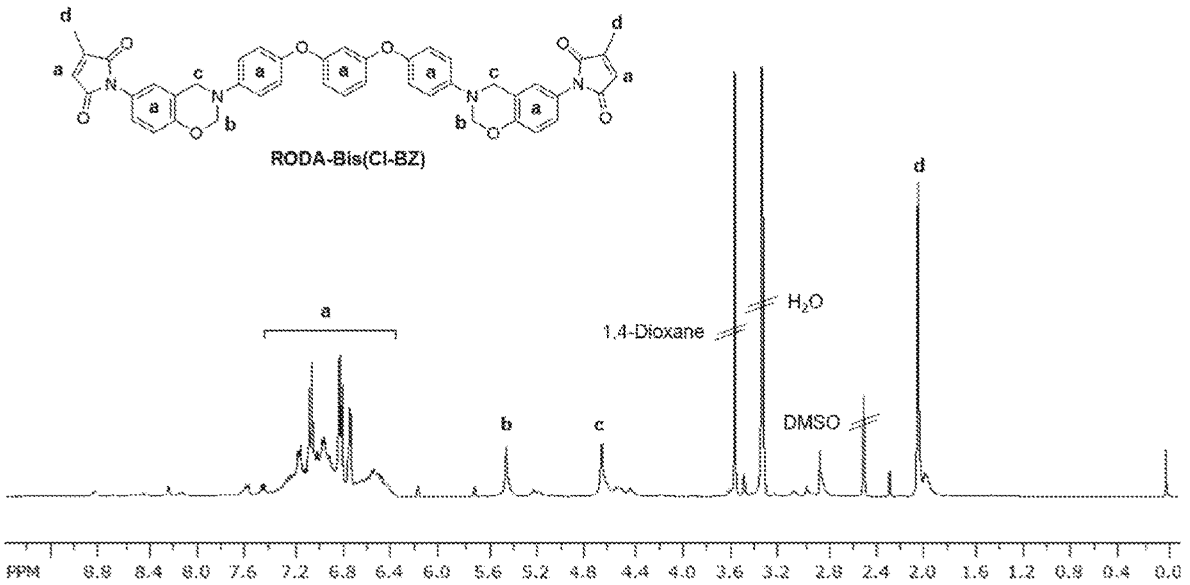
FIG. 24 shows 1H NMR spectra of RODA-Bis(CI-BZ) in accordance with one or more embodiments of the present disclosure.
Figure 25:
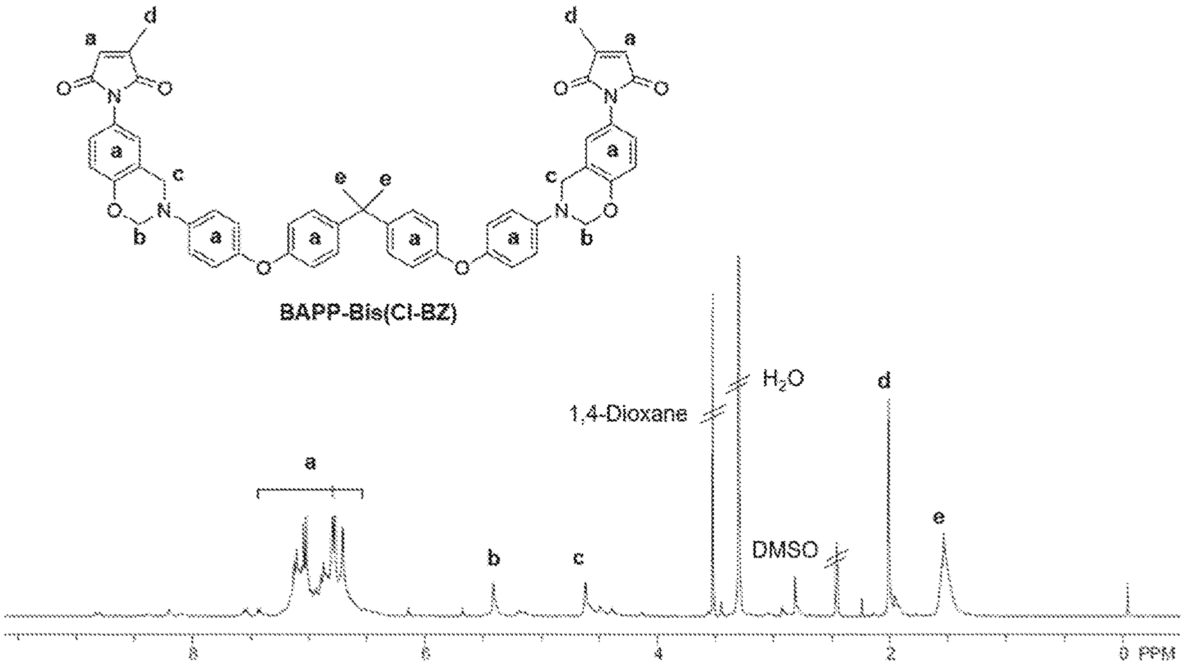
FIG. 25 shows 1H NMR spectra of BAPP-Bis(CI-BZ) in accordance with one or more embodiments of the present disclosure.
Figure 26:
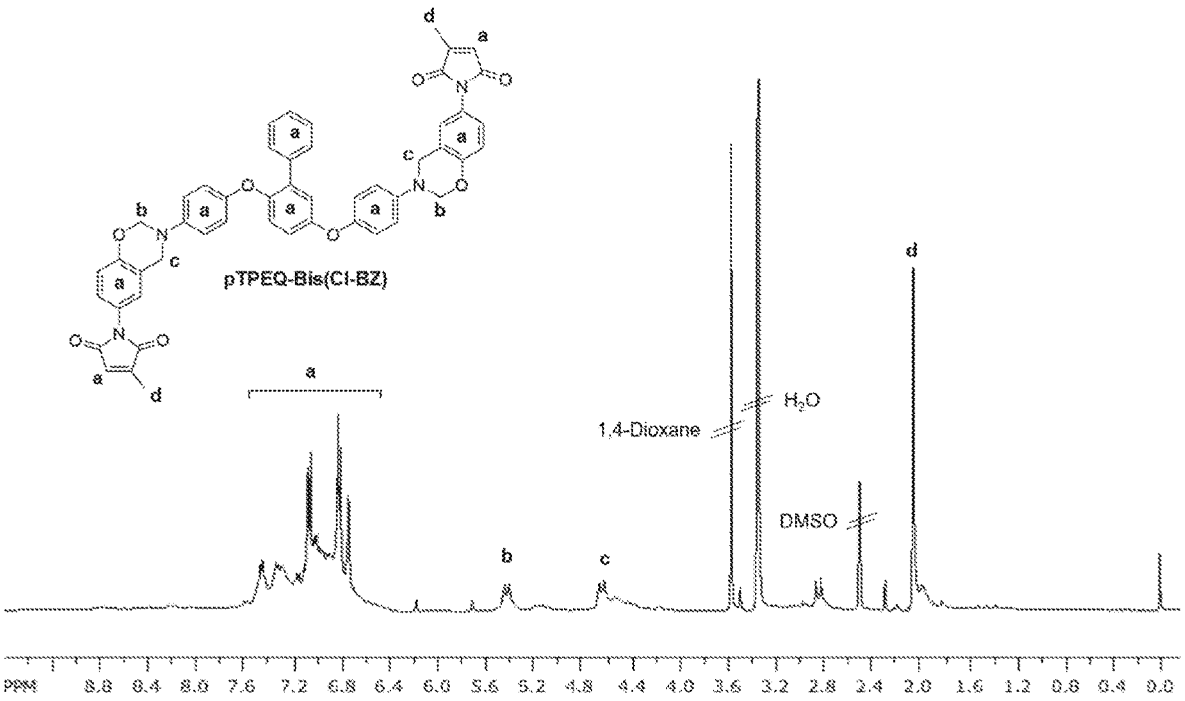
FIG. 26 shows 1H NMR spectra of pTPEQ-Bis(CI-BZ) in accordance with one or more embodiments of the present disclosure.

FIGS. 24, 25 and 26 show the $^1$H NMR spectra of the benzoxazine resins prepared in Examples 12, 13, and 14, respectively. The formation of benzoxazine ring via Mannich reaction was confirmed by the assignment of two resonance peaks around 4.6 and 5.4 ppm with equivalent integration ratio to $CH_2$ groups in the benzoxazine ring in the $^1$H NMR spectra. Also, a resonance peak around 1.9 ppm was assigned to a $CH_3$ group of citraconic imide functional group. The residual unreacted phenolic starting material (i.e., HPCI) was observed in the $^1$H NMR spectra. However, it is not anticipated to be detrimental to the properties of the resin and the cured resin, considering that the residual starting material may act as an additional crosslinker. Meanwhile, alkenyl proton resonance peaks from citraconic imide moieties overlapped with multiple aromatic resonance peaks in the range of 6.4-7.5 ppm.

Figure 27:
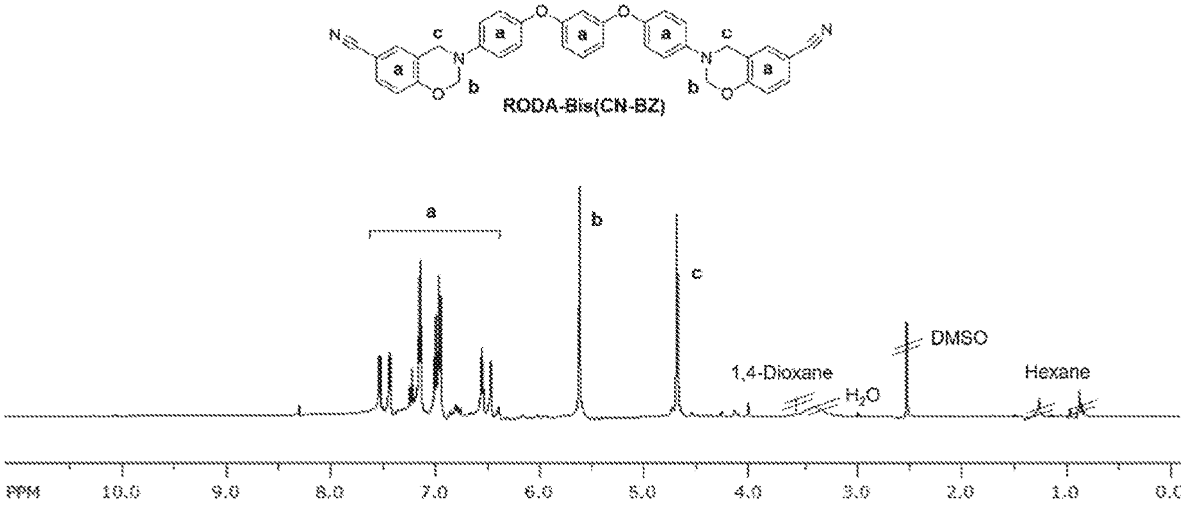
FIG. 27 shows 1H NMR spectra of RODA-Bis(CN-BZ) in accordance with one or more embodiments of the present disclosure.
Figure 28:
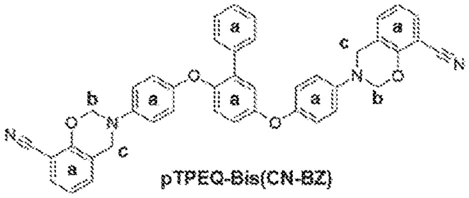
FIG. 28 shows 1H NMR spectra of pTPEQ-Bis(CN-BZ) in accordance with one or more embodiments of the present disclosure.
Figure 28:
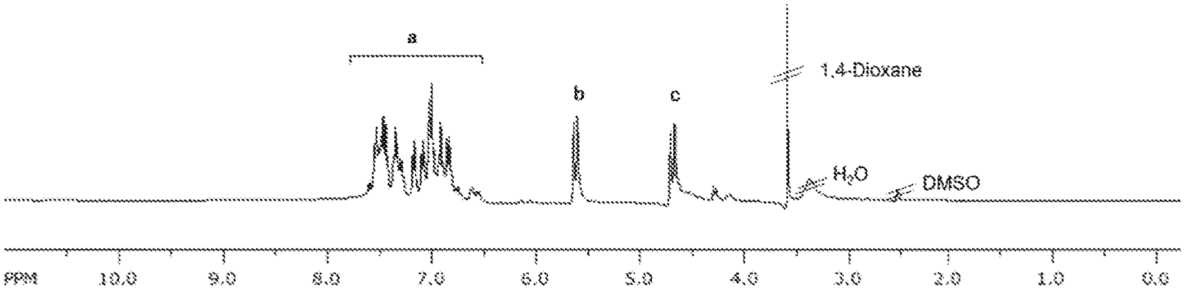
Figure 29:
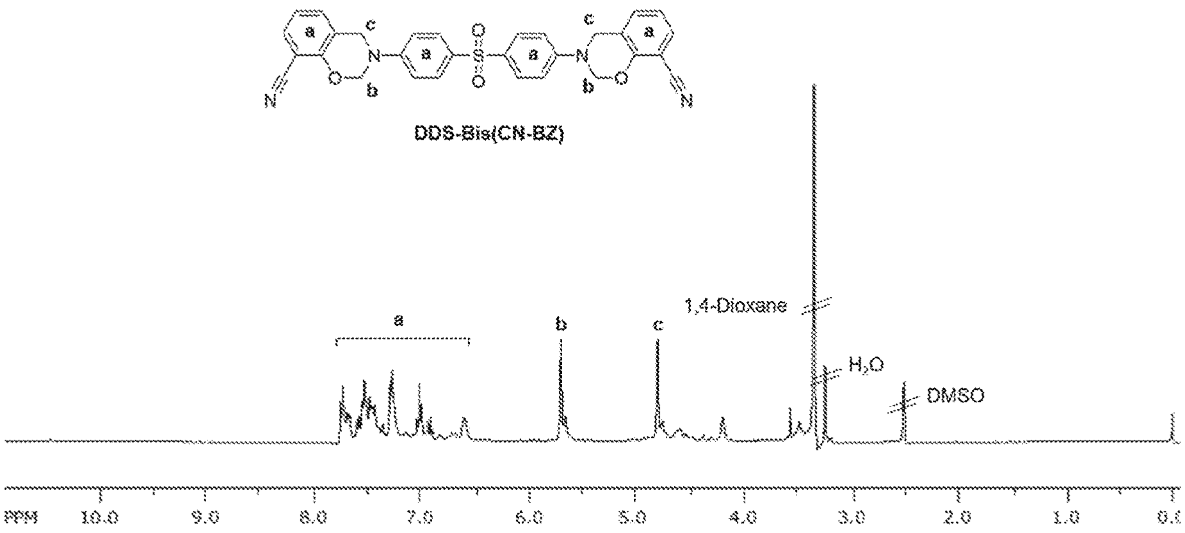
FIG. 29 shows 1H NMR spectra of DDS-Bis(CN-BZ) in accordance with one or more embodiments of the present disclosure.

FIGS. 27, 28 and 29 show the $^1$H NMR spectra of the benzoxazine resins prepared in Examples 15, 16 and 17, respectively. The formation of benzoxazine ring via Mannich reaction was confirmed by the assignment of two resonance peaks around 4.7 and 5.6 ppm with equivalent integration ratio to $CH_2$ groups in the benzoxazine ring in the $^1$H NMR spectra. The residual unreacted phenolic starting material (i.e., 2-HBN) was observed in the $^1$H NMR spectra. However, it is not anticipated to be detrimental to the properties of the resin and the cured resin, considering that the residual starting material may act as an additional crosslinker.

Figure 30:
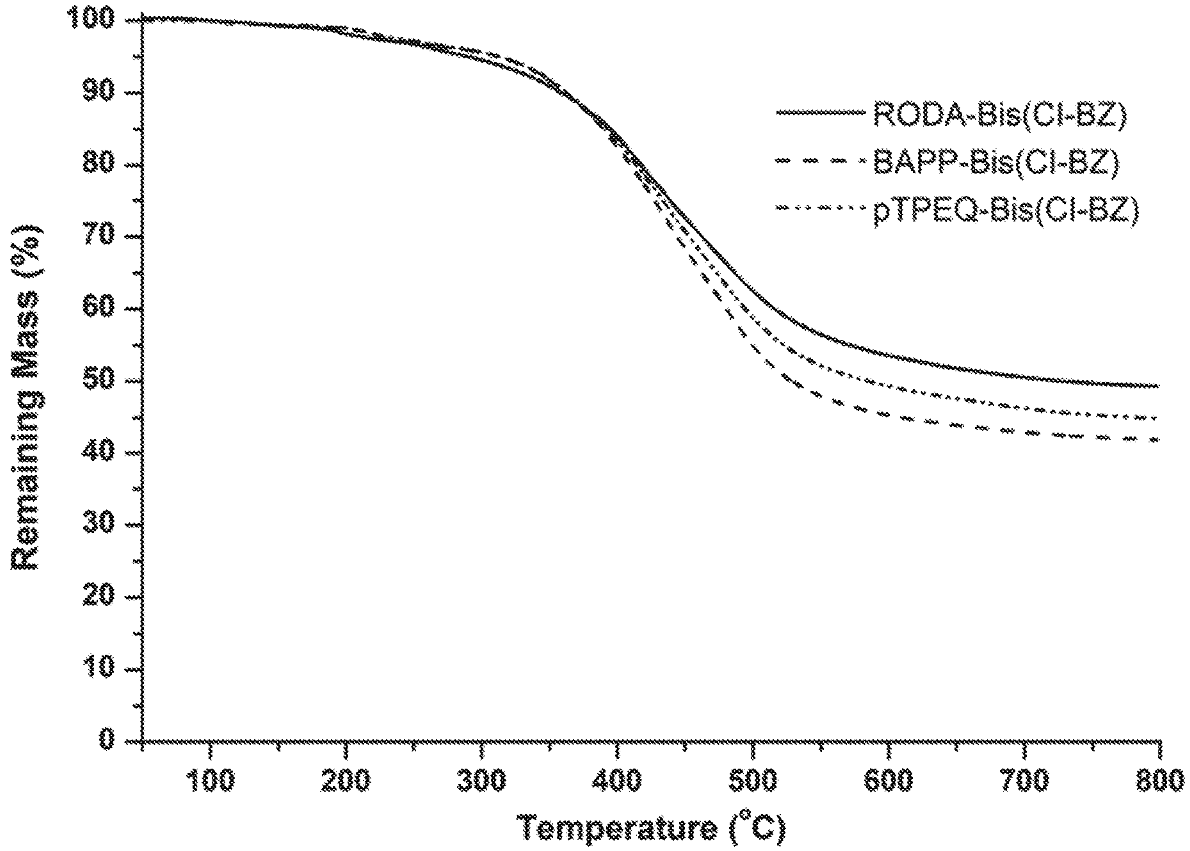
FIG. 30 shows TGA thermograms of RODA-Bis(CI-BZ), BAPP-Bis(CI-BZ), and pTPEQ-Bis(CI-BZ) in accordance with one or more embodiments of the present disclosure.
Figure 31:
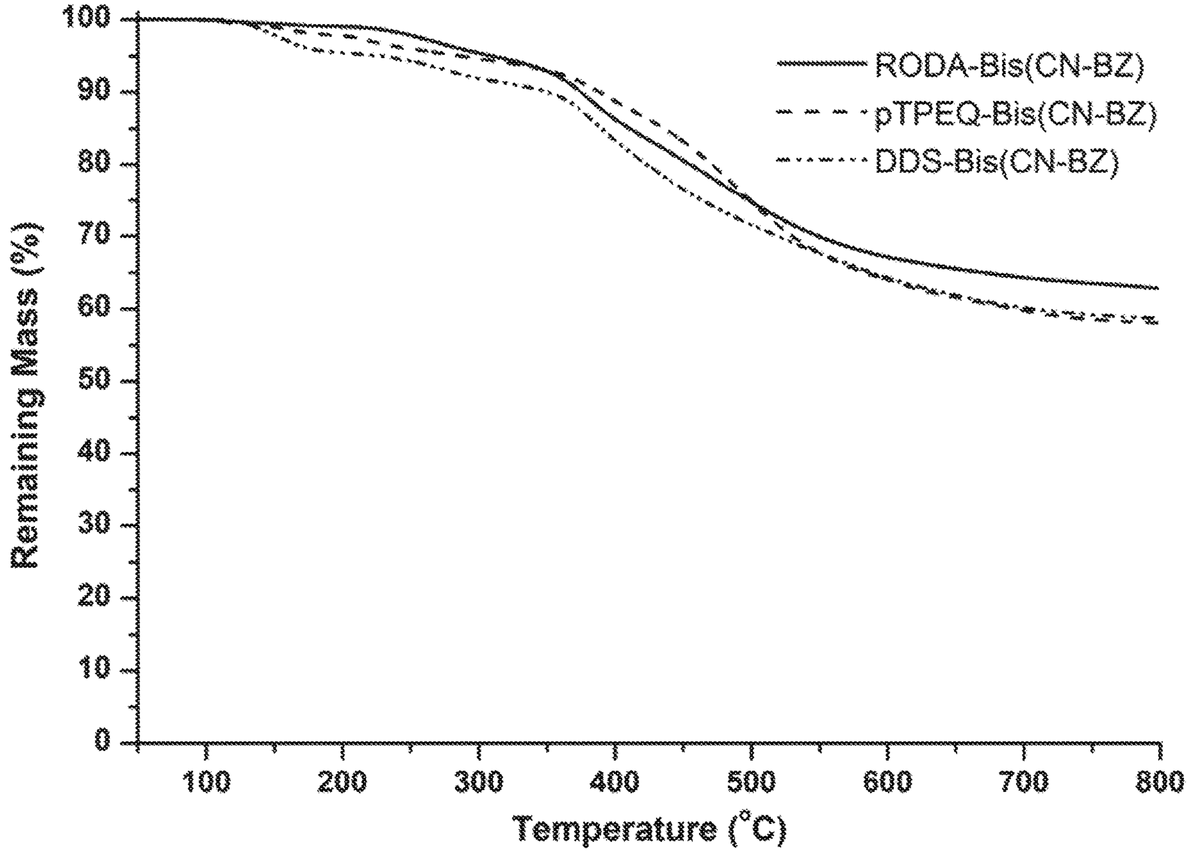
FIG. 31 shows TGA thermograms of RODA-Bis(CN-BZ), pTPEQ-Bis(CN-BZ), and DDS-Bis(CN-BZ) in accordance with one or more embodiments of the present disclosure.
Figure 32:
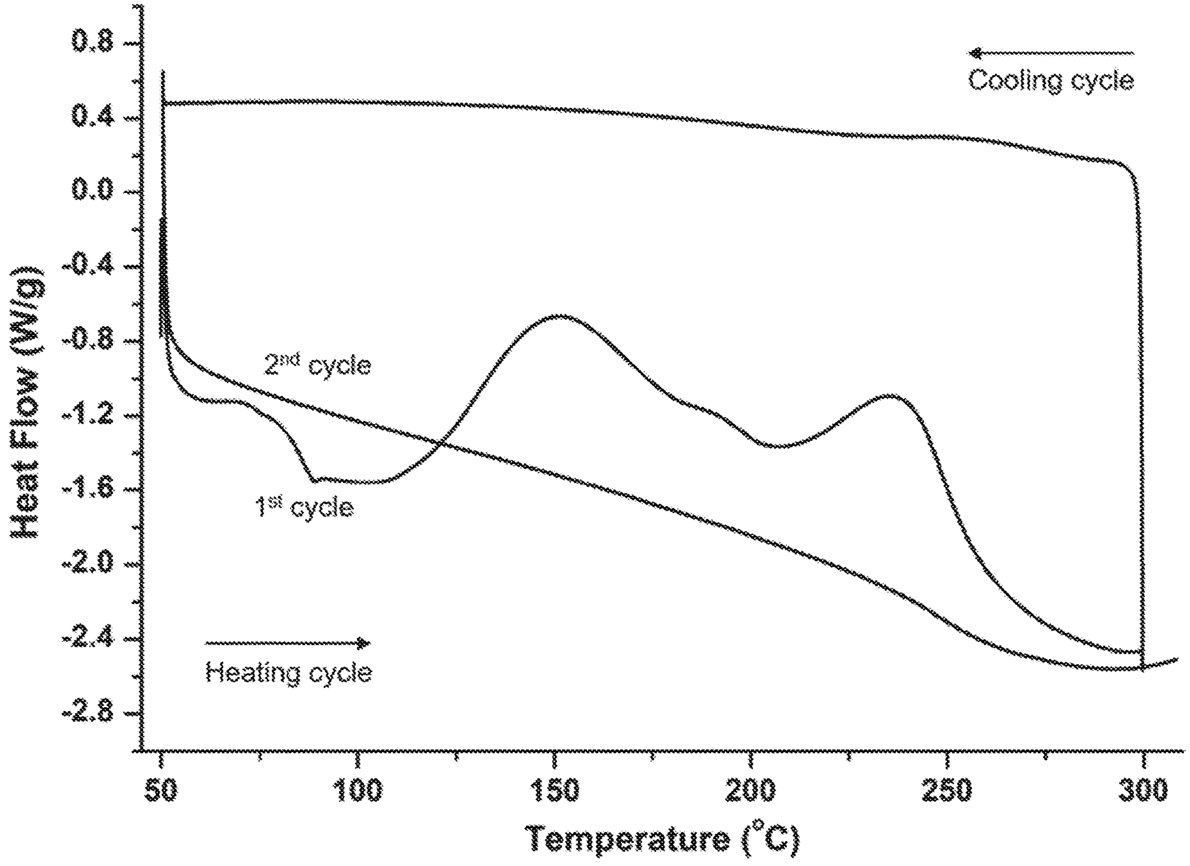
FIG. 32 shows DSC thermograms of RODA-Bis(CI-BZ) in accordance with one or more embodiments of the present disclosure.
Figure 33:
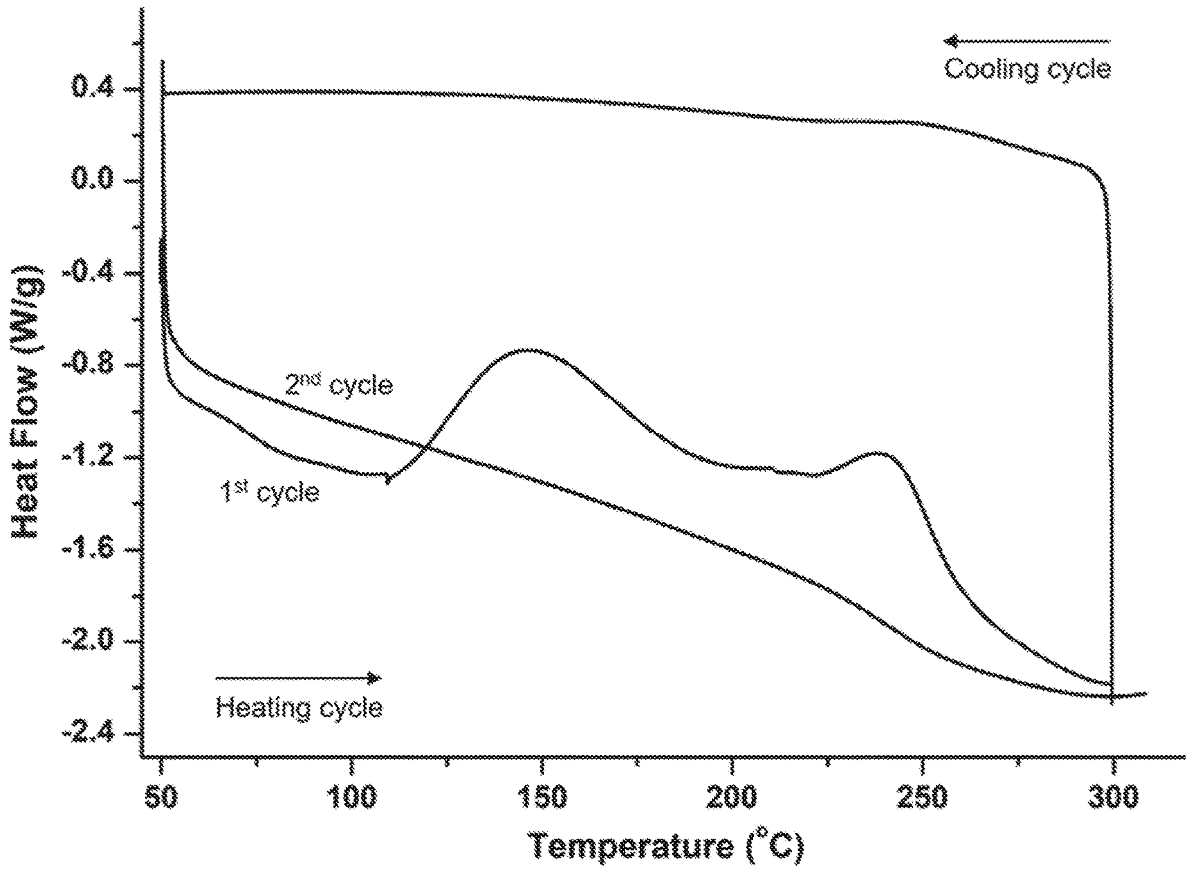
FIG. 33 shows DSC thermograms of BAPP-Bis(CI-BZ) in accordance with one or more embodiments of the present disclosure.
Figure 34:
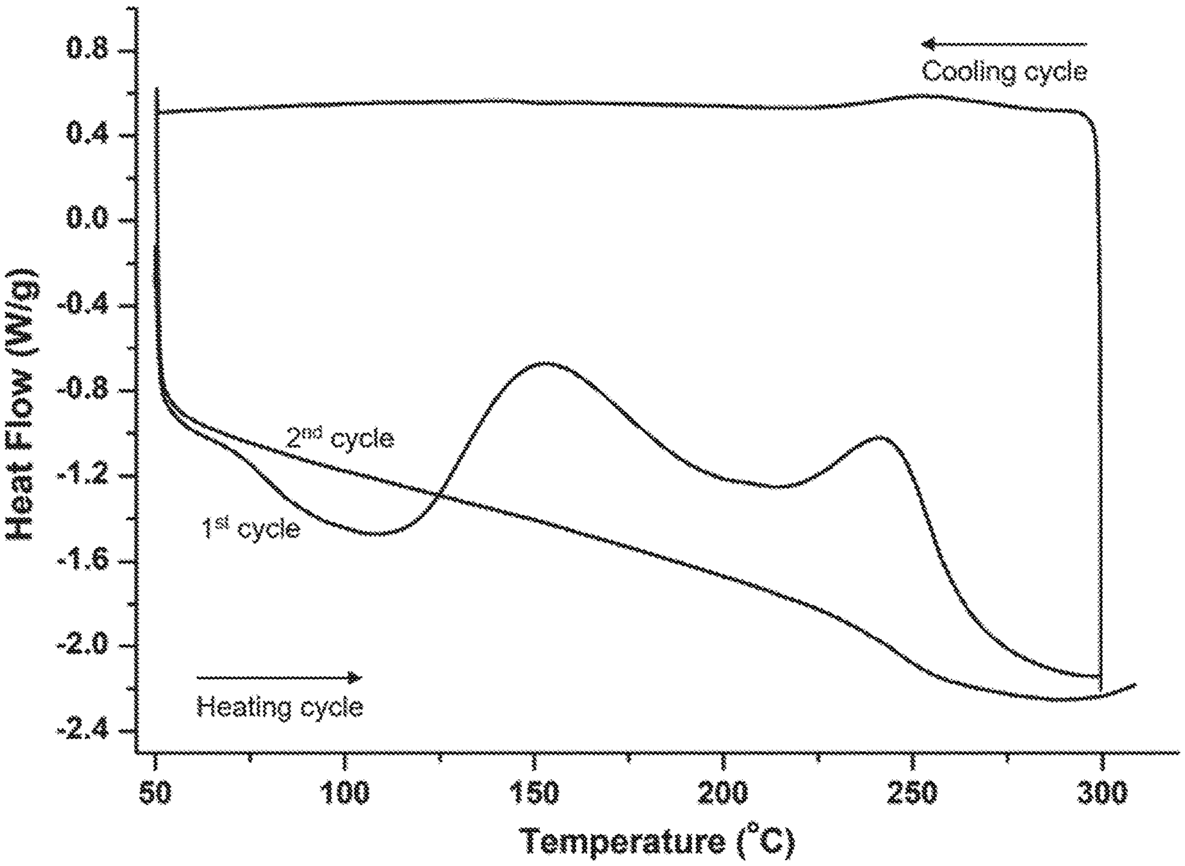
FIG. 34 shows DSC thermograms of pTPEQ-Bis(CI-BZ) in accordance with one or more embodiments of the present disclosure.
Figure 35:
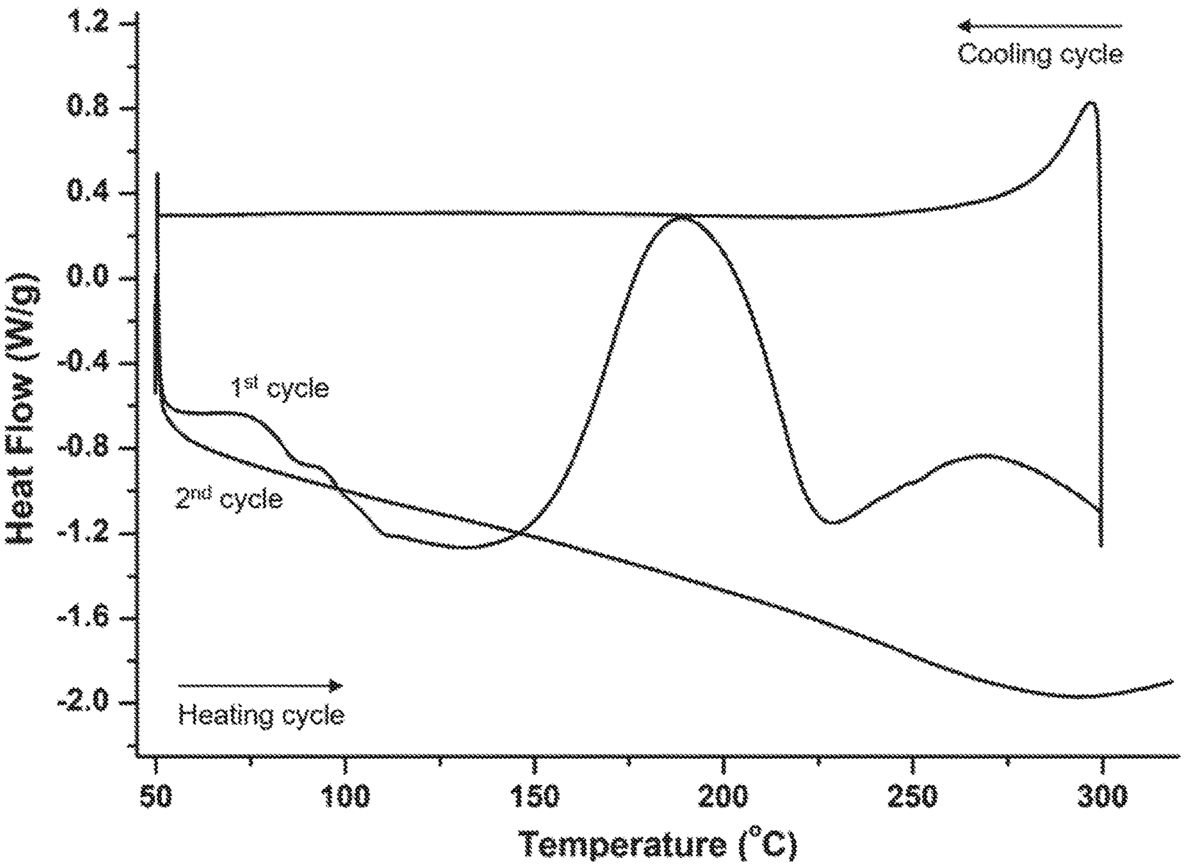
FIG. 35 shows DSC thermograms of RODA-Bis(CN-BZ) in accordance with one or more embodiments of the present disclosure.
Figure 36:
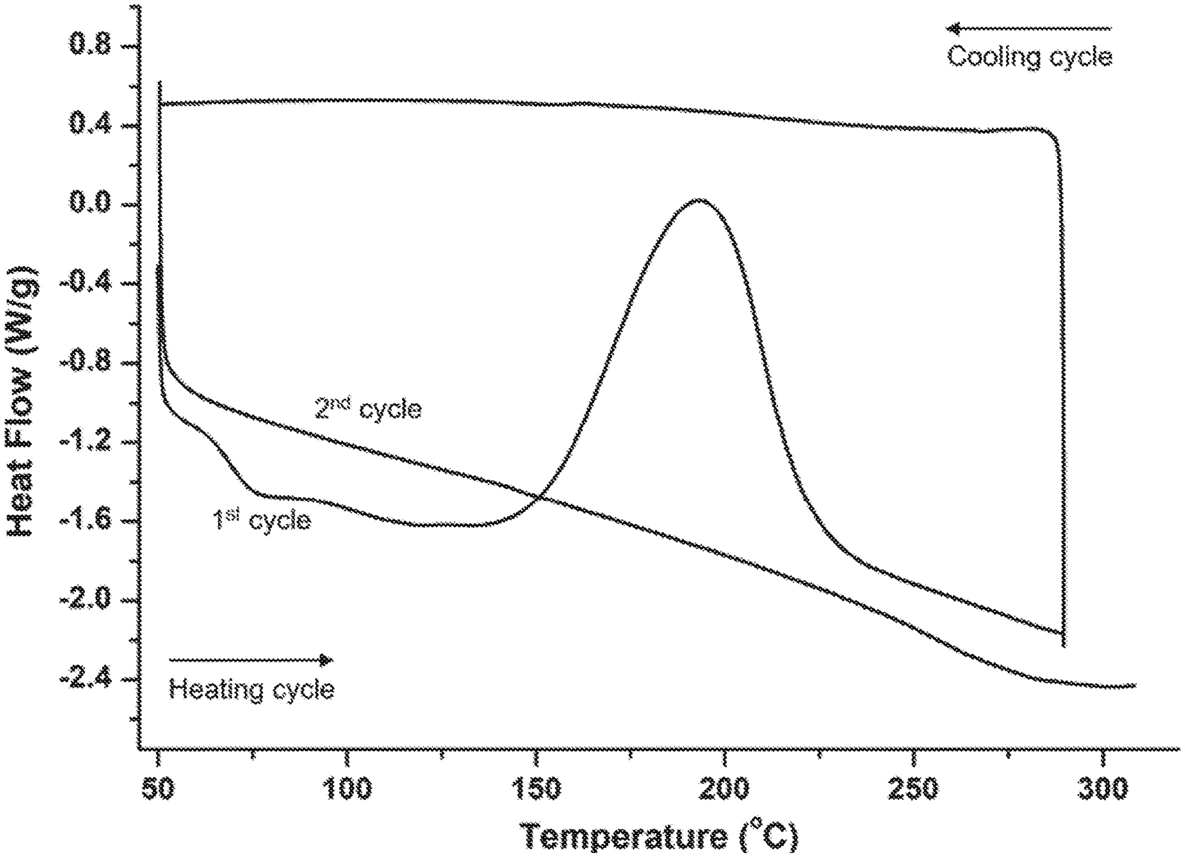
FIG. 36 shows DSC thermograms of pTPEQ-Bis(CN-BZ) in accordance with one or more embodiments of the present disclosure.
Figure 37:
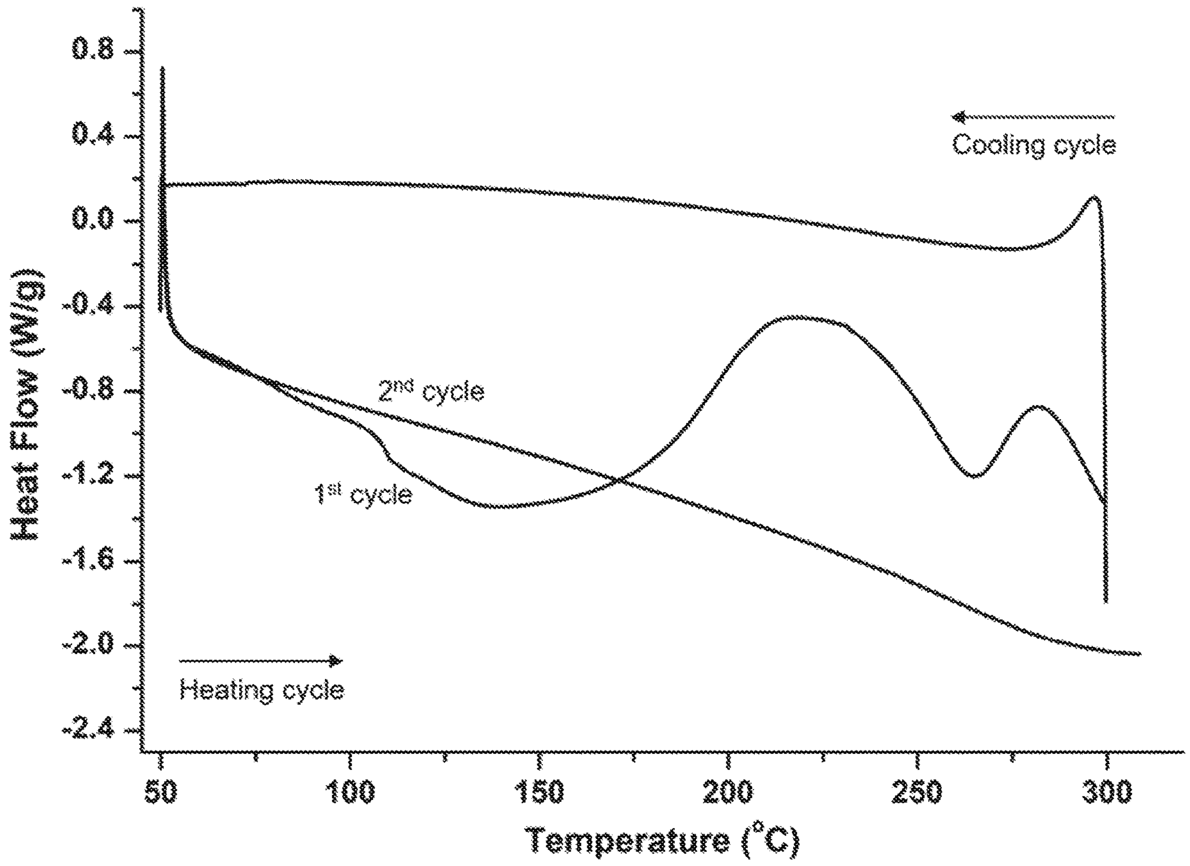
FIG. 37 shows DSC thermograms of DDS-Bis(CN-BZ) in accordance with one or more embodiments of the present disclosure.

Thermal stability of the benzoxazine resins was determined by TGA, as shown in FIGS. 30 and 31. Table 3 summaries the TGA thermograms of the resins under $N_2$ atmosphere. The char yield illustrated in this disclosure indicates the remaining mass of the resin at 800° C. under $N_2$ atmosphere. Benzoxazine resins containing citraconic imide functional groups (Examples 12-14) displayed high thermal stability in general. Upon heating at 5° C./min on TGA, RODA-Bis(CI-BZ) displayed 5% mass loss ($T_{d,5\%}$) at 305° C., 10% mass loss ($T_{d,10\%}$) at 365° C., and 49% of char yield at 800° C. BAPP-Bis(CI-BZ) displayed $T_{d,5\%}$ at 322° C., $T_{d,10\%}$ at 365° C., and 42% of char yield at 800° C. Finally, pTPEQ-Bis(CI-BZ) revealed $T_{d,5\%}$ at 324° C., $T_{d,10\%}$ at 367° C., and 45% of char yield at 800° C.

Benzoxazine resins containing nitrile functional groups (Examples 15-17) also showed high thermal stability and char yield. RODA-Bis(CN-BZ) displayed $T_{d,5\%}$ at 322° C., $T_{d,10\%}$ at 378° C., and 63% of char yield at 800° C. pTPEQ-Bis(CN-BZ) had $T_{d,5\%}$ at 322° C., $T_{d,10\%}$ at 398° C., and 58% of char yield at 800° C. Finally, DDS-Bis(CI-BZ) showed $T_{d,5\%}$ at 282° C., $T_{d,10\%}$ at 372° C., and 59% of char yield at 800° C.

In comparison, P-d (a commercial benzoxazine resin) and CYCOM® 4250 (a commercial bismaleimide resin) showed higher $T_{d,5\%}$ (i.e., 343° C. and 462° C., respectively) than Examples 3-8. Meanwhile, char yields of both P-d and CYCOM® 4250 at 800° C. were 49%, which was higher than those of Examples 12-14 and lower than those of Examples 15-17.

TABLE 3

TGA profiles ($T_{d,5\%}$, $T_{d,10\%}$, and char yield at 800° C.) of P-d, CYCOM ® 4250 (BMI), and Examples 12-15

| Sample | $T_{d,5\%}$ (° C.) | $T_{d,10\%}$ (° C.) | Char yield at 800° C. |
|---|---|---|---|
| P-d | 343 | 384 | 49 |
| CYCOM ® 4250 (BMI) | 462 | 474 | 49 |
| RODA-Bis(CI-BZ) (Example 12) | 305 | 365 | 49 |
| BAPP-Bis(CI-BZ) (Example 13) | 322 | 365 | 42 |
| pTPEQ-Bis(CI-BZ) (Example 14) | 324 | 367 | 45 |
| RODA-Bis(CN-BZ) (Example 15) | 322 | 378 | 63 |
| pTPEQ-Bis(CN-BZ) (Example 16) | 322 | 398 | 58 |
| DDS-Bis(CN-BZ) (Example 17) | 282 | 372 | 59 |

Thermal curing behavior of the benzoxazine resins and $T_g$ of the cured resins were investigated by DSC by heating at 5° C. per min, as shown in FIGS. 32-37. Table 4 describes the temperatures for onset curing and maximum curing peaks of Examples 12-14, observed on the $1^{st}$ cycle of DSC curve. It is noteworthy that the effect of citraconic imide functional group moieties of benzoxazine resins on lowering the overall curing temperature, as well as the onset curing temperature, was evident when compared with those temperatures of typical maleimide-containing thermosetting resins.

TABLE 4

Temperatures for onset curing and maximum curing peaks of Examples 12-14, as observed on the $1^{st}$ cycle of DSC curve

| | Example 12 | Example 13 | Example 14 |
|---|---|---|---|
| Onset curing temperature (° C.) | 106 | 108 | 110 |
| $1^{st}$ Max. curing peak temp. (° C.) | 150 | 145 | 152 |
| $2^{nd}/3^{rd}$ Max. curing peak temp. (° C.) | 237 | 240 | 243 |

Onset glass transition temperature ($T_{g,onset}$) of each of Examples 12, 13, and 14 was measured on the $2^{nd}$ cycle of DSC curve—235, 223, and 236° C., respectively.

On the $1^{st}$ cycle of DSC curve of Examples 15 and 17, there were two distinct exothermal peaks due to the predicted two-step curing mechanism, that is, the crosslinking reaction between two benzoxazine moieties followed by formation of a triazine structure comprising three nitrile functional group moieties upon heating. Example 15 showed onset curing temperature at 130° C., $1^{st}$ max. curing exothermal peak at 189° C., and $2^{nd}$ max. curing exothermal peak at 267° C. Similarly, Example 17 showed onset curing temperature at 140° C., $1^{st}$ max. curing exothermal peak at 215° C., and $2^{nd}$ max. curing exothermal peak at 282° C. A more rigid sulfone linkage of Example 17 when compared with an ether linkage of Example 15 appeared to delay the curing rate by limiting its intermolecular mobility and interaction. Interestingly, Example 16 had a monomodal exothermal curing peak with maximum curing exothermal peak at 193° C. Crosslinking of nitrile functional group moieties seemed to occur at much lower temperature, simultaneously with crosslinking of benzoxazine moieties. On the $2^{nd}$ cycle, $T_{g,onset}$ appeared at 239, 240, and 244° C. for Examples 15, 16, and 17, respectively.

Figure 38:
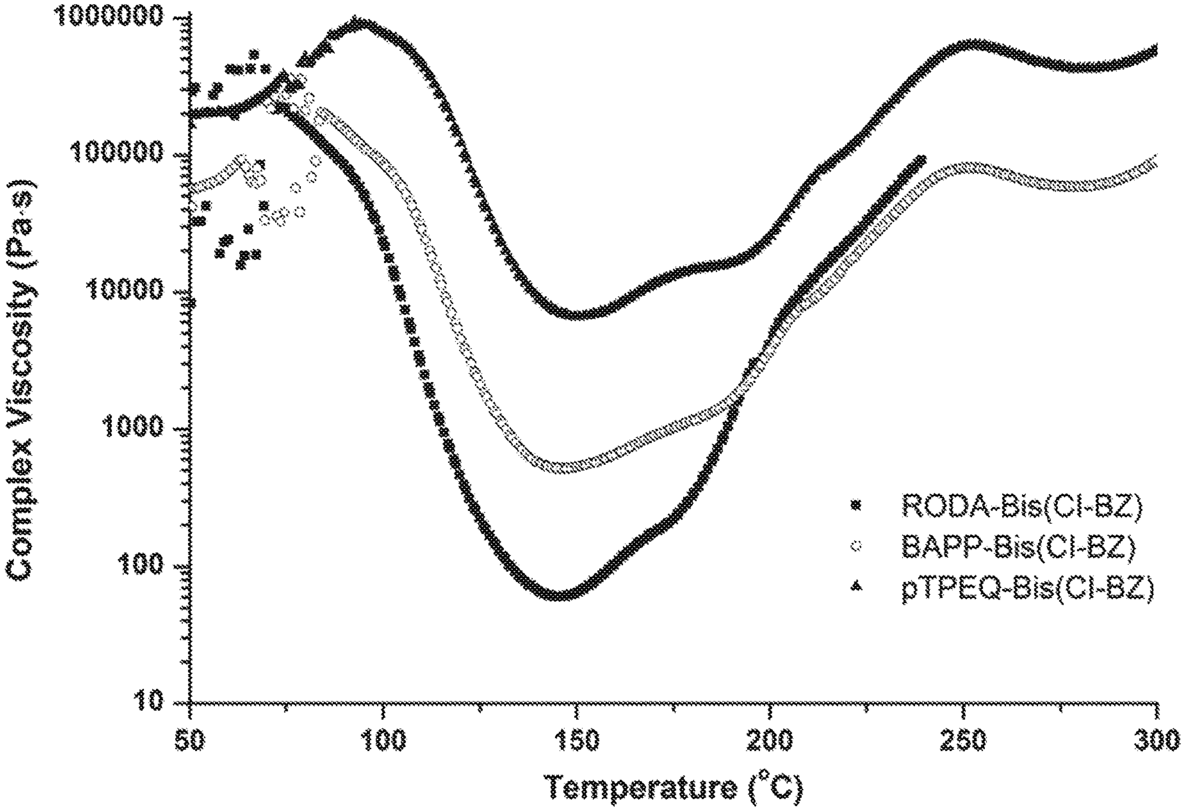
FIG. 38 shows a graph of complex viscosities of RODA-Bis(CI-BZ), BAPP-Bis(CI-BZ), and pTPEQ-Bis(CI-BZ) as a function of temperature in accordance with one or more embodiments of the present disclosure.
Figure 39:
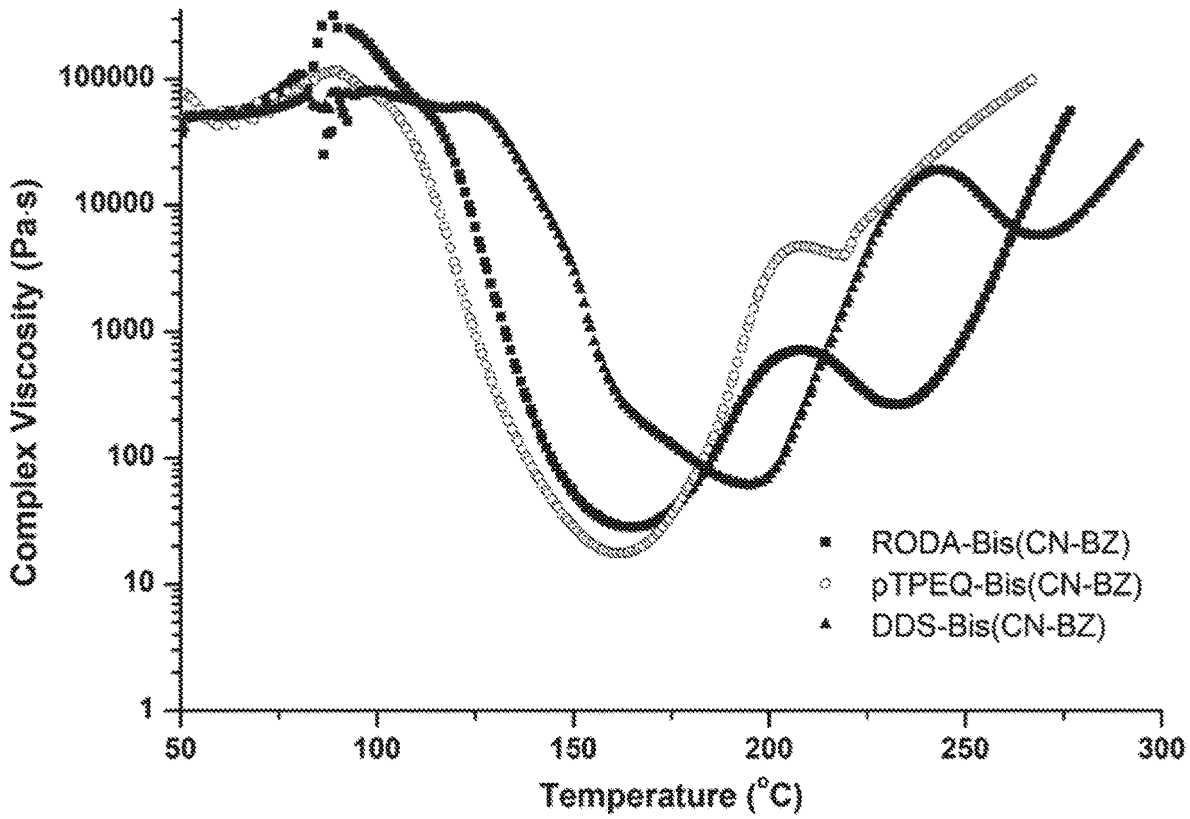
FIG. 39 shows a graph of complex viscosities of RODA-Bis(CN-BZ), pTPEQ-Bis(CN-BZ), and DDS-Bis(CN-BZ) as a function of temperature in accordance with one or more embodiments of the present disclosure.

The structural integration of benzoxazine and citraconic or nitrile functional groups in one chemical compound allowed for a low melt-viscosity of the benzoxazine resins. Complex viscosities (or melt-viscosity) for the benzoxazine resins as a function of temperature are shown in FIGS. 38 and 39. For instance, in a particular embodiment, the complex viscosity of Example 12 could reach below 5000 Pa·s, a critical viscosity threshold for prepregging, in the temperature range of 107-202° C. and below 100 Pa·s, a critical viscosity threshold for pre-molding, in the temperature range of 133-159° C. with the minimum complex viscosity, 60° C., at 145° C. The complex viscosity values of Examples 13 and 14 were higher than those of Example 12. Example 13 displayed complex viscosity lower than 5000 Pa·s in the temperature range of 120 and 202° C. and lowest value, 517 Pa·s, at 147° C. Finally, Example 14 had the lowest complex viscosity, 6597 Pa·s at 151° C.

Nitrile functional group-containing benzoxazine resins also showed very high melt-flowability when measured by rheometer. Complex viscosity of Example 15 was less than 5000 Pa·s in the temperature range of 126 and 261° C. and less than 100 Pa·s in the temperature range of 144 and 186° C., with the minimum viscosity, 28 Pa·s, at 165° C. Complex viscosity of Example 16 was less than 5000 Pa·s in the temperature range of 118 and 221° C. and less than 100 Pa·s in the temperature range of 138 and 184° C., with the minimum viscosity, 17 Pa·s, at 162° C. Finally, complex viscosity of Example 17 was less than 5000 Pa·s in the temperature range of 147 and 226° C. and 100 Pa·s in the temperature range of 180 and 204° C., with the minimum viscosity, 60 Pa·s, at 196° C.

Figure 40A:
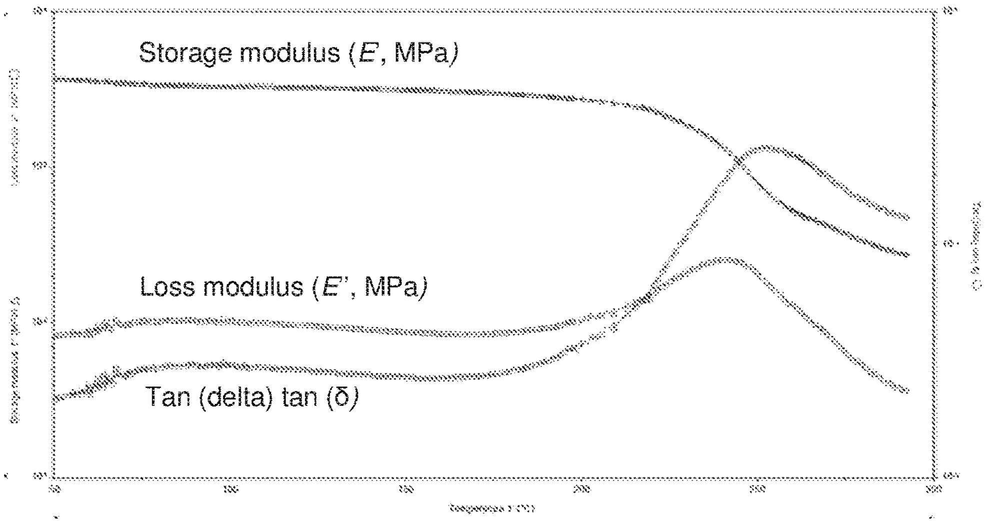
FIGS. 40A-C show graphs of storage modulus (MPa) and loss modulus (MPa) of RODA-Bis(CI-BZ), BAPP-Bis(CI-BZ), and pTPEQ-Bis(CI-BZ), respectively, as a function of temperature in accordance with one or more embodiments of the present disclosure.
Figure 41A:
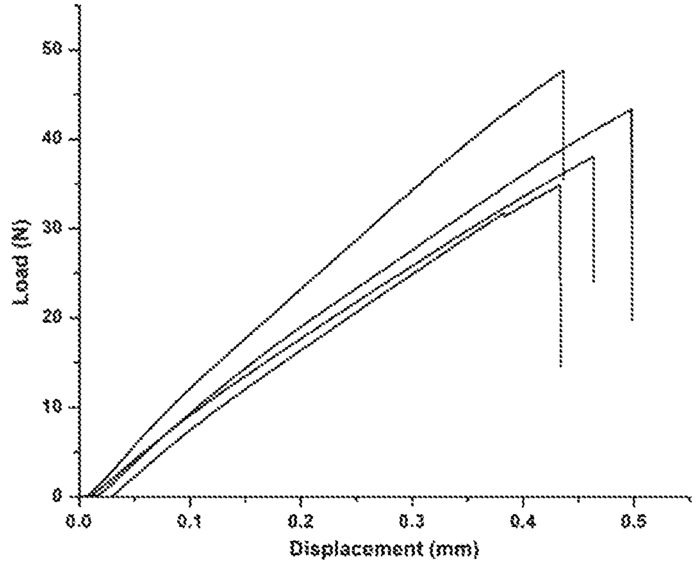
FIGS. 41A-C show stress-strain curves from tensile test of RODA-Bis(CI-BZ), BAPP-Bis(MI-BZ), and pTPEQ-Bis (CI-BZ), respectively, in accordance with one or more embodiments of the present disclosure.

Example 12 was molded into a thin film of 170 μm in thickness. DMA indicated $T_g$ of the molded film of the resin to be at 230° C. (FIG. 40A and Table 5). According to the tensile test results, the prepared molded film displayed 47±14 MPa of strength, 3.0±0.4 GPa of modulus, and 2.0±0.4% of elongation, (FIG. 41A and Table 5).

Figure 40B:
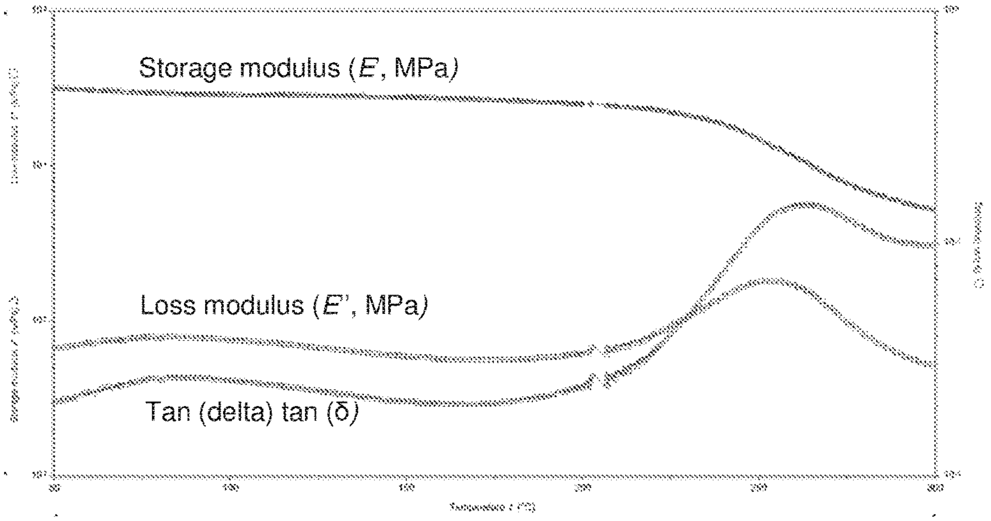
Figure 41B:
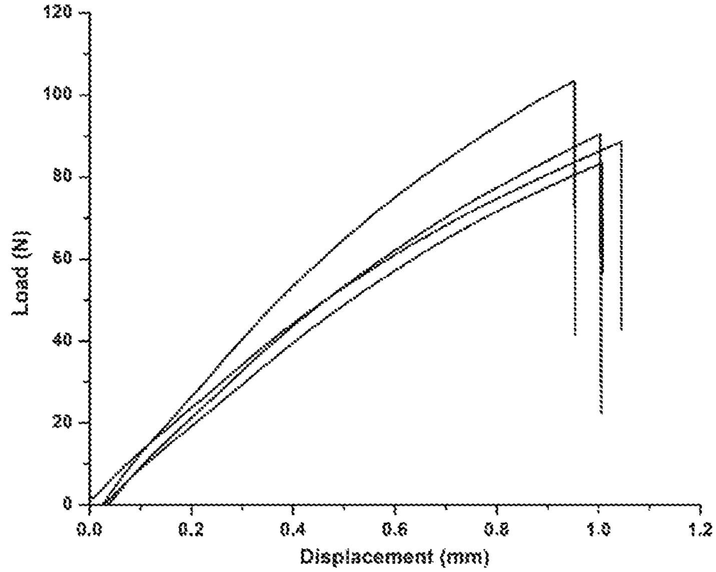

Example 13 was molded into a thin film of 180 μm in thickness. DMA indicated $T_g$ of the molded film of the resin to be at 238° C. (FIG. 40B and Table 5). According to the tensile test results, the prepared molded film displayed 76±18 MPa of strength, 2.8±0.6 GPa of modulus, and 4.0±0.2% of elongation (FIG. 41B and Table 5).

Figure 40C:
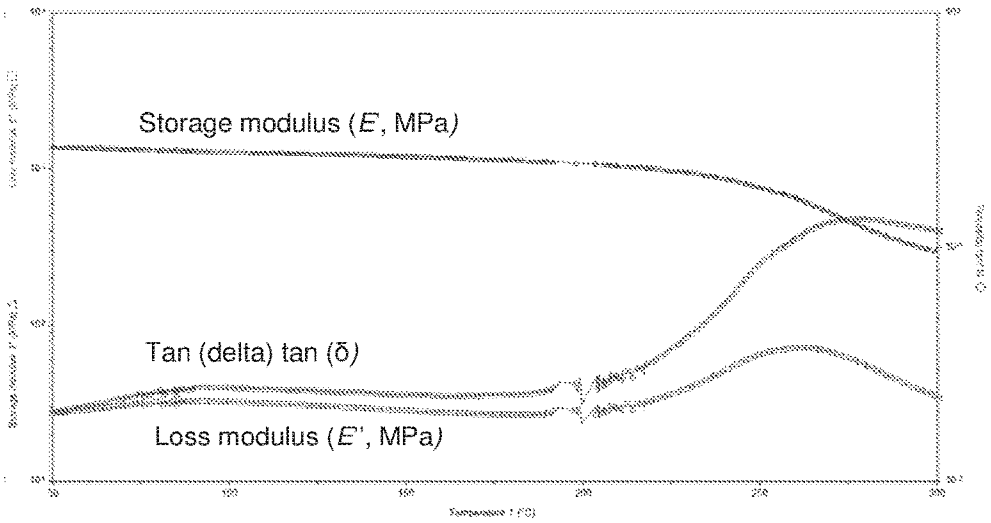
Figure 41C:
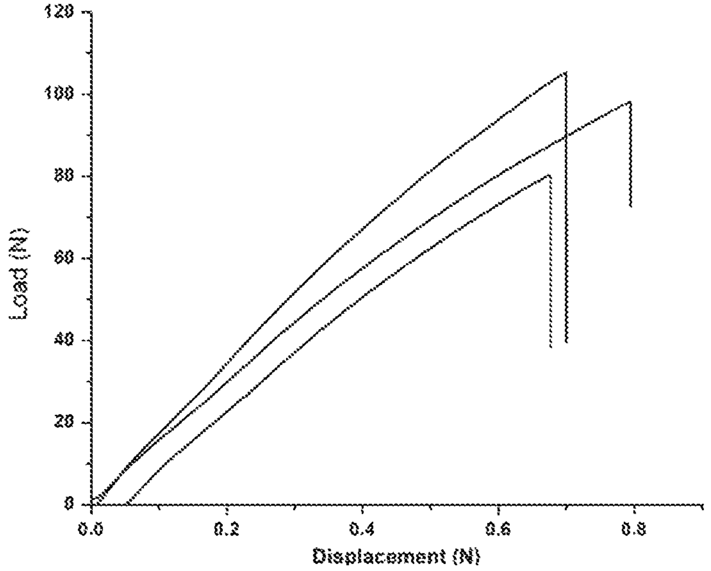

Example 14 was molded into a thin film of 160 μm in thickness. DMA indicated $T_g$ of the molded film of the resin to be at 246° C. (FIG. 40C and Table 5). According to the tensile test results, the prepared molded film displayed 59±26 MPa of strength, 2.5±0.7 GPa of modulus, and 2.9±0.3% of elongation (FIG. 41C and Table 5).

Figure 42A:
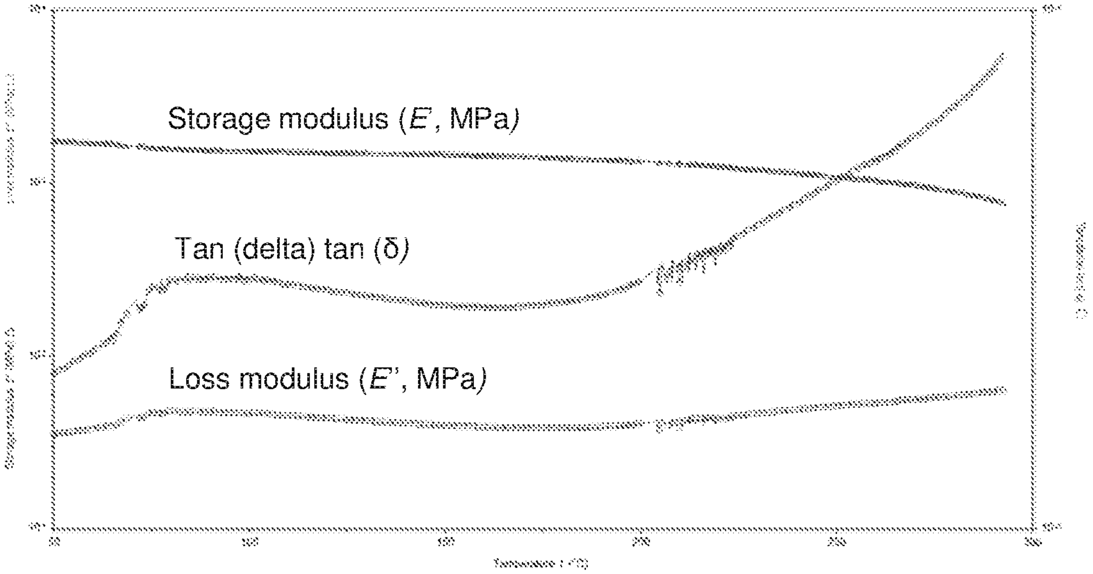
FIGS. 42A-B show graphs of storage modulus (MPa) and loss modulus (MPa) of RODA-Bis(CN-BZ) and pTPEQ-Bis(CN-BZ), respectively, as a function of temperature in accordance with one or more embodiments of the present disclosure.
Figure 43A:
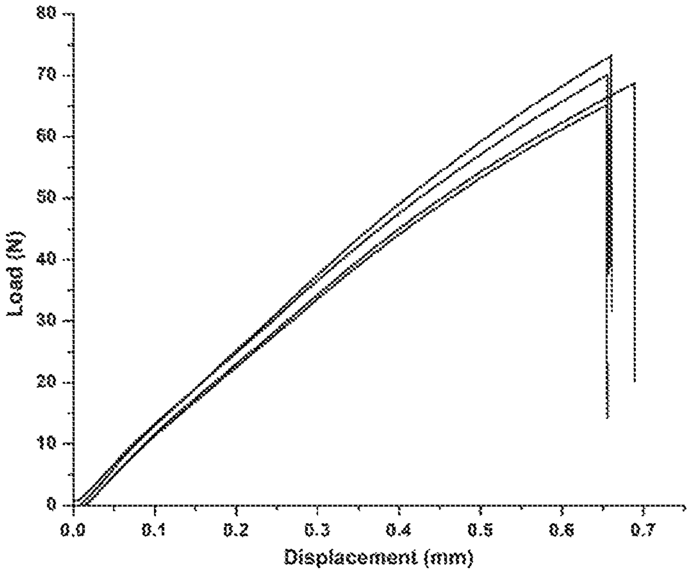
FIGS. 43A-B show stress-strain curves from the tensile test of RODA-Bis(CN-BZ) and pTPEQ-Bis(CN-BZ), respectively, in accordance with one or more embodiments of the present disclosure.

Example 15 was molded into a thin film of 200 μm in thickness. $T_g$ of the molded film of the resin was not found in the evaluated temperature range (50-300° C.) on DMA measurement (FIG. 42A and Table 5). According to the tensile test results, the prepared molded film displayed 62±8.0 MPa of strength, 3.0±0.3 GPa of modulus, and 2.7±0.1% of elongation (FIG. 43A and Table 5).

Figure 42B:
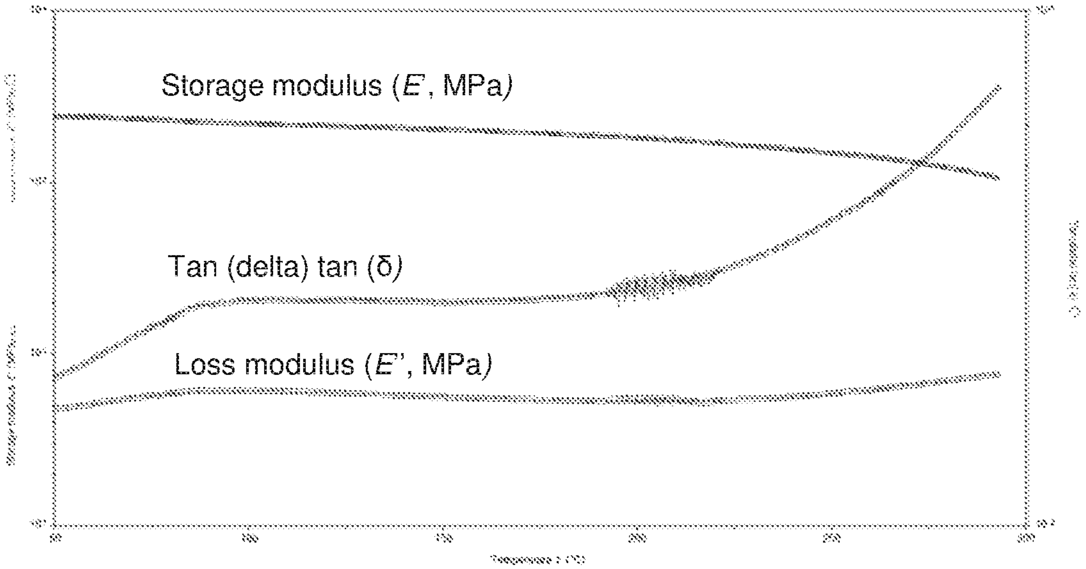
Figure 43B:
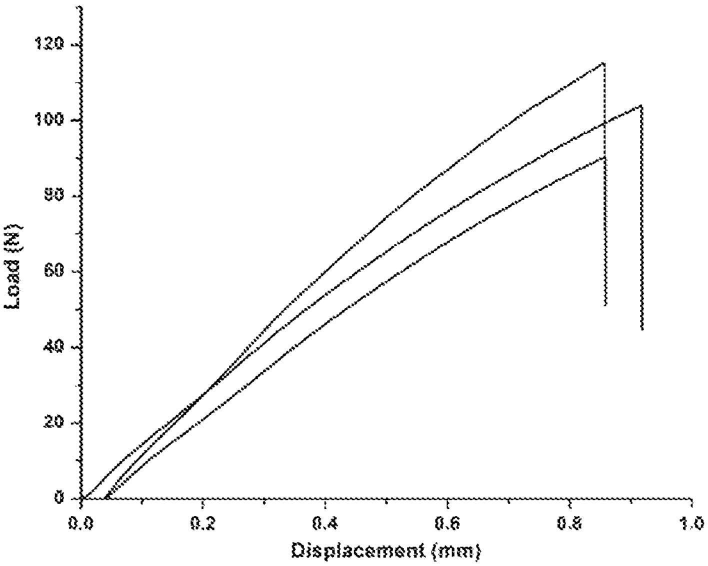

Example 16 was molded into a thin film of 190 μm in thickness. $T_g$ of the molded film of the resin was not found in the evaluated temperature range (50-300° C.) on DMA measurement (FIG. 42B and Table 5). According to the tensile test results, the prepared molded film displayed 78±7.0 MPa of strength, 3.0±0.5 GPa of modulus, and 3.5±0.1% of elongation (FIG. 43B and Table 5).

An attempt was made to mold Example 17 into a thin film, but the resulting film was too brittle to be used for evaluation (Table 5).

The aforementioned properties are summarized in Table 5 below:

TABLE 5

Thermal and mechanical properties of benzoxazine resins

| | Onset temp. exothermal peaks ($1^{st}$) (° C.) | Dry $T_g$ (° C.) | Tensile properties Strength (MPa) | Modulus (GPa) | Strain (%) | Viscosity profile (° C.) @5000 Pa · s | @100 Pa · s |
|---|---|---|---|---|---|---|---|
| CYCOM ® 4250 (BMI) | 163 (BMI-1000) | 300 | 103 | 4.6 | 4.8 | N/A | 78-183 |
| P-d | 200 | 187 | 82 ± 6.5 | 3.1 ± 0.2 | 3.2 ± 0.4 | 80-222 | 88-218 |
| RODA-Bis(CI-BZ) (Example 12) | 106 | 230 | 47 ± 14 | 3.0 ± 0.4 | 2.0 ± 0.4 | 107-202 | 133-159 |
| BAPP-Bis(CI-BZ) (Example 13) | 108 | 238 | 76 ± 18 | 2.8 ± 0.6 | 4.0 ± 0.2 | 120-202 | N/A |
| pTPEQ-Bis(CI-BZ) (Example 14) | 110 | 246 | 59 ± 26 | 2.5 ± 0.7 | 2.9 ± 0.3 | N/A | N/A |
| RODA-Bis(CN-BZ) (Example 15) | 130 | Not observed up to 300° C. | 62 ± 8.0 | 3.0 ± 0.3 | 2.7 ± 0.1 | 126-261 | 144-186 |
| pTPEQ-Bis(CN-BZ) (Example 16) | 140 | Not observed up to 300° C. | 78-7.0 | 3.0 ± 0.5 | 3.5 ± 0.1 | 118-221 | 138-184 |
| DDS-Bis(CN-BZ) (Example 17) | 140 | N/A | N/A | N/A | N/A | 147-226 | 180-204 |

A furan functional group-containing benzoxazine resin (i.e., BPA-Bis(F-BZ)) was formulated into a series of curable compositions with three types of maleimide functional group-containing benzoxazine resin (i.e., RODA-Bis(MI-BZ) of Example 1, BAPP-Bis(MI-BZ) of Example 4, and pTPEQ-Bis(MR-BZ) of Example 7) as summarized in Table 6 below in accordance with the followed detailed descriptions.

TABLE 6

Content of Prepared Curable Compositions

| Formulation | Content |
|---|---|
| 1 | BPA-Bis(F-BZ):RODA-Bis(MI-BZ) = 1.0:0.5 |
| 2 | BPA-Bis(F-BZ):RODA-Bis(MI-BZ) = 1.0:1.0 |
| 3 | BPA-Bis(F-BZ):RODA-Bis(MI-BZ) = 0.5:1.0 |
| 4 | BPA-Bis(F-BZ):BAPP-Bis(MI-BZ) = 1.0:1.0 |
| 5 | BPA-Bis(F-BZ):pTPEQ-Bis(MI-BZ) = 1.0:1.0 |
| 6 (Comparative) | BPA-Bis(F-BZ):RODA-Bis(MI-BZ) = 0:1.0 |
| 7 (Comparative) | BPA-Bis(F-BZ):BAPP-Bis(MI-BZ) = 0:1.0 |
| 8 (Comparative) | BPA-Bis(F-BZ):pTPEQ-Bis(MI-BZ) = 0:1.0 |

Example 18: Synthesis of Bisphenol A-bis(furan-benzoxazine) (BPA-Bis(F-BZ))

Furfuryl amine (23.3088 g, 0.2400 mol), bisphenol A (BPA) (27.3948 g, 0.1200 mol), and paraformaldehyde (14.4144 g, 0.4800 mol) were placed in a 500 mL of round-bottom flask equipped with a magnetic stir bar, and xylene (360 mL) was added. After stirring for 30 min at ambient temperature, the solution was heated at 120° C. in air for 2 days while vigorously stirring. Once the solution was cooled to room temperature, it was precipitated into hexane while stirring. The desired product, BPA-Bis(F-BZ), was obtained after drying in vacuo overnight.

Example 19: Formulation 1 Curable Composition of BPA-Bis(F-BZ) (1.0) and RODA-Bis(MI-BZ) (0.5)

BPA-Bis(F-BZ) (0.0941 g, 0.2 mmol), RODA-Bis(MI-BZ) (0.0719 g, 0.1 mmol), and THE (5 mL) were placed in a 20 mL glass vial equipped with a magnetic stir bar. The solution was stirred for 10 minutes at room temperature until it became a clear solution. THE was removed in vacuo at ambient temperature followed by holding at 40° C. overnight. The dried solid was ground into a fine powder by using a mortar and pestle.

Example 20: Formulation 2 Curable Composition of BPA-Bis(F-BZ) (1.0) and RODA-Bis(MI-BZ) (1.0)

BPA-Bis(F-BZ) (0.0706 g, 0.15 mmol), RODA-Bis(MI-BZ) (0.1078 g, 0.15 mmol), and THE (5 mL) were placed in a 20 mL glass vial equipped with a magnetic stir bar. The solution was stirred for 10 minutes at room temperature until it became a clear solution. THE was removed in vacuo at ambient temperature followed by holding at 40° C. overnight. The dried solid was ground into a fine powder by using a mortar and pestle.

Example 21: Formulation 3 Curable Composition of BPA-Bis(F-BZ) (0.5) and RODA-Bis(MI-BZ) (1.0)

BPA-Bis(F-BZ) (0.0471 g, 0.1 mmol), RODA-Bis(MI-BZ) (0.1437 g, 0.2 mmol), and THE (5 mL) were placed in a 20 mL glass vial equipped with a magnetic stir bar. The solution was stirred for 10 min at room temperature until it became a clear solution. THE was removed in vacuo at ambient temperature followed by holding at 40° C. overnight. The dried solid was ground into a fine powder by using a mortar and pestle.

Example 22: Formulation 4 Curable Composition of BPA-Bis(F-BZ) (1.0) and BAPP-Bis(MI-BZ) (1.0)

BPA-Bis(F-BZ) (2.0235 g, 4.3 mmol), BAPP-Bis(MI-BZ) (3.5987 g, 4.3 mmol), and THE (10 mL) were placed in a 20 mL glass vial equipped with a magnetic stir bar. The solution was stirred for 10 min at room temperature until it became a clear solution. THE was removed in vacuo at ambient temperature followed by holding at 40° C. overnight. The dried solid was ground into a fine powder by using a mortar and pestle.

Example 23: Formulation 5 Curable Composition of BPA-Bis(F-BZ) (1.0) and pTPEQ-Bis(MI-BZ) (1.0)

BPA-Bis(F-BZ) (2.0705 g, 4.4 mmol), pTPEQ-Bis(MI-BZ) (3.4972 g, 4.4 mmol), and THE (10 mL) were placed in a 20 mL glass vial equipped with a magnetic stir bar. The solution was stirred for 10 min at room temperature until it became a clear solution. THE was removed in vacuo at ambient temperature followed by holding at 40° C. overnight. The dried solid was ground into a fine powder by using a mortar and pestle.

Film Molding

Thin films (in the range of 150 and 300 μm in thickness) of formulations described above were made on a hot press using the following cure cycle: the press was preheated to 155° C.; the sample was placed in the press and after the sample was fully melted, bumping (10 bumps) at 3 MPa was applied; the press was held for 60 min; the press was ramped to 180° C. at 5° C./min and then held for 50 min; the press was ramped to 220° C. at 5° C./min and then held for 40 min; the press was ramped to 260° C. at 5° C./min and then held for 60 min; and finally, the press was cooled down to room temp at 5° C./min at a pressure of 3 MPa.

Tensile, Thermal, and Melt-Viscosity Data of Formulations 1-8

Thin films from the above described Formulations 2, 4, and 5 and comparative examples (Formulations 6-8), and the thermal and tensile properties were measured from the molded thin films. The results, along with the thermal and melt-viscosity data of the curable compositions, are summarized in Table 2 below.

TABLE 7

Comparisons of Formulations 1-8 in Thermal and Mechanical Properties

| | | Formulation | | | | | | | |
|---|---|---|---|---|---|---|---|---|---|
| | | 1 | 2 | 3 | 4 | 5 | 6 (CE) | 7 (CE) | 8 (CE) |
| Onset temp. of exothermal peaks (° C.) | | 132 | 136 | 138 | 136 | 137 | 145 | 125 | 124 |
| Dry $T_g$ (° C.) | | N/A | 285 | N/A | 288 | 285 | 268 | 273 | 269 |
| Tensile properties | Strength (MPa) | N/A | 72 ± 21 | N/A | 61 ± 11 | 60 ± 10 | 98 ± 13 | 83 ± 7.0 | 77 ± 5.9 |
| | Modulus (GPa) | N/A | 2.7 ± 0.7 | N/A | 2.7 ± 0.5 | 2.7 ± 0.3 | 3.6 ± 0.19 | 3.0 ± 0.12 | 3.2 ± 0.14 |
| | Strain (%) | N/A | 3.3 ± 0.6 | N/A | 3.0 ± 0.6 | 2.6 ± 0.3 | 5.0 ± 1.1 | 3.9 ± 0.42 | 3.6 ± 0.67 |
| Viscosity profile (° C.) | @5000 Pa · s | N/A | 132-192 | N/A | 132-194 | 136-192 | 112-202 | 152-190 | 158-185 |
| | @100 Pa · s | N/A | 152-162 | N/A | 152-167 | 157-165 | 133-180 | N/A | N/A |

Figure 44:
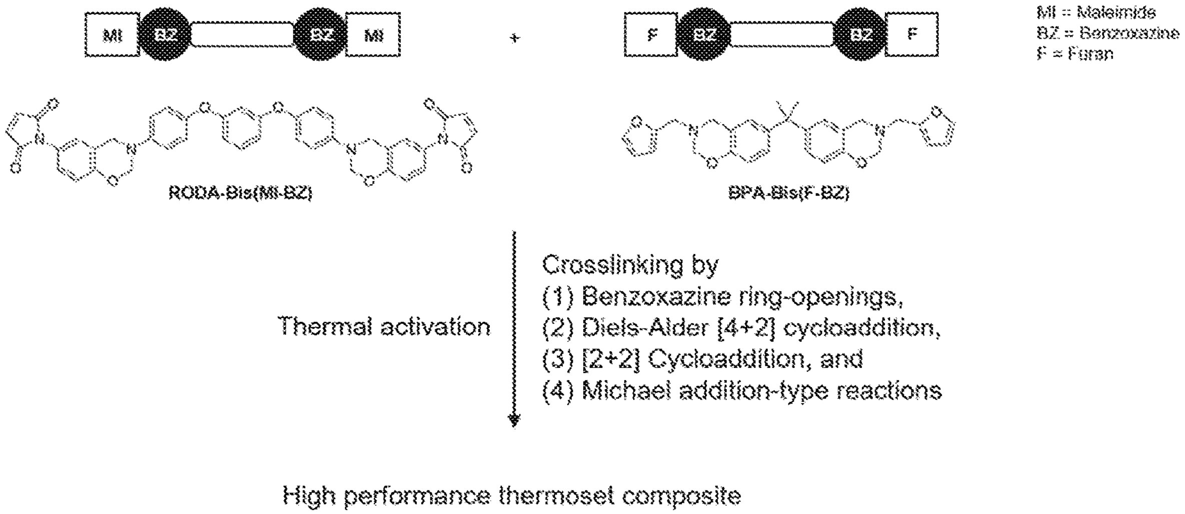
FIG. 44 shows a schematic illustration of the curing of curable composition by thermal activation, in accordance with one or more embodiments of the present disclosure.

The effect of a furan functional group-containing benzoxazine resin (BPA-Bis(F-BZ)) on lowering the curing temperature of a maleimide functional group-containing benzoxazine resin (RODA-Bis(MI-BZ)) was studied by comparing four formulations (Formulations 1-3 and 6) having different content ratios of BPA-Bis(F-BZ) and RODA-Bis(MI-BZ) (Table 6 and FIG. 44). While not wishing to be bound by any particular mechanism or theory, it is believed that the Diels-Alder [4+2] cycloaddition reaction between a furan group of BPA-Bis(F-BZ) and a maleimide group of RODA-Bis(MI-BZ) is more favorable than the [2+2] cycloaddition of two maleimide moieties of RODA-Bis(MI-BZ). This favorability may result in lower cured temperature of RODA-Bis(MI-BZ) resins. A formulation containing equimolar ratio of BPA-Bis(FF-BZ) and RODA-Bis(MI-BZ) (i.e., Formulation 2) is expected to have the lowest curing temperature of Formulations 1-3 and 6 due to a complete consumption of furan and maleimide moieties by the Diels-Alder reaction at lower curing temperature. However, if either BPA-Bis(FF-BZ) or RODA-Bis(MI-BZ) is in excess (Formulations 1, 3, and 4), a less favorable interaction between two furan moieties or between two maleimide moieties would require higher temperature for the complete curing conversion.

Figure 45:
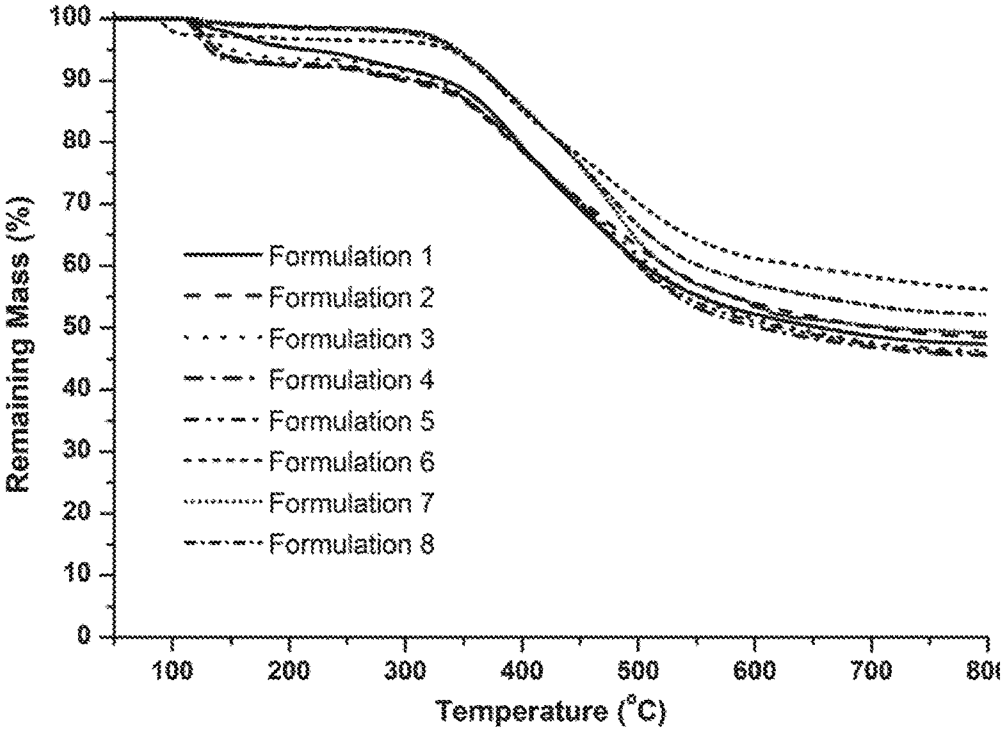
FIG. 45 shows a TGA profile of Formulations 1-8, in accordance with one or more embodiments of the present disclosure.

As shown in FIG. 45, thermogravimetric analysis data shows that all of the formulations were thermally stable up to 350° C. For instance, Formulation 2 displayed a $T_{d,5\%}$ at 342° C., $T_{d,10\%}$ at 374° C., and 53% of char yield at 800° C. Formulation 4 displayed a $T_{d,5\%}$ at 342° C., $T_{d,10\%}$ at 376° C., and 49% of char yield at 800° C. Formulation 5 displayed a $T_{d,5\%}$ at 341° C., $T_{d,10\%}$ at 374° C., and 49% of char yield at 800° C.

Figure 46:
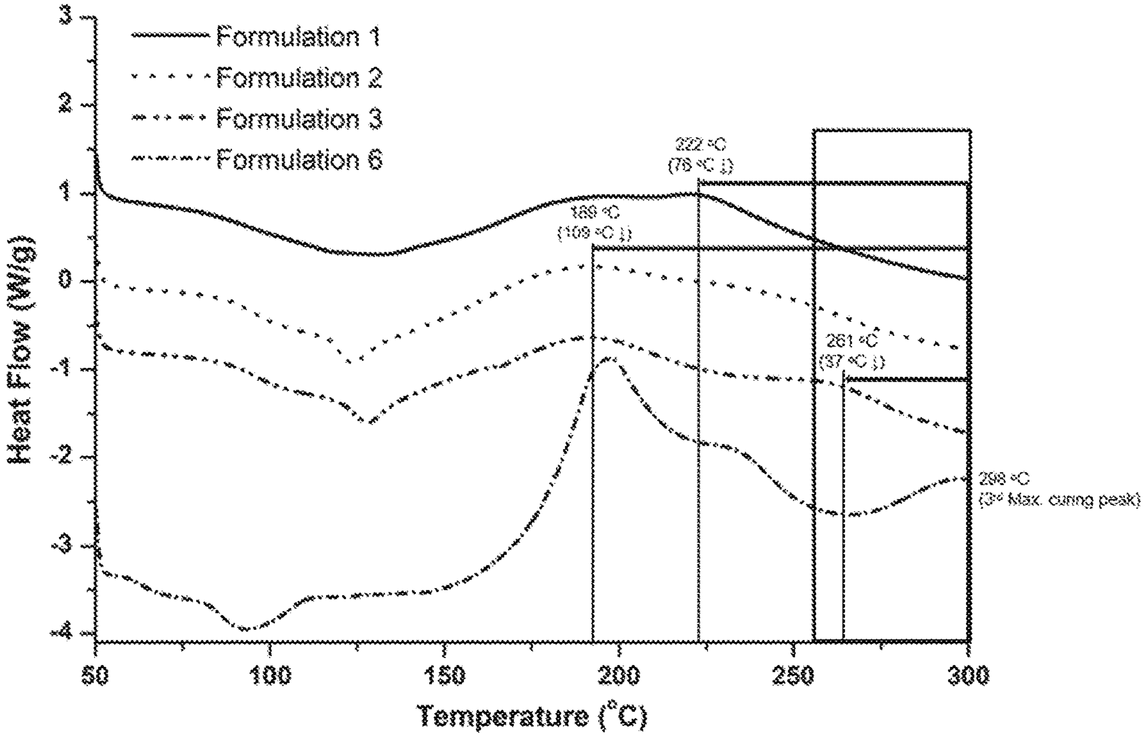
FIG. 46 shows DSC curves of Formulations 1, 2, 3, and 6, in accordance with one or more embodiments of the present disclosure.

Thermal behavior of each formulation was evaluated using dynamic scanning calorimetry (DSC), and the results are shown in FIG. 46. On the 1st cycle of DSC curve, it was evident that the addition of BPA-Bis(FF-BZ) as a co-monomer in Formulations 1-3 contributed to lowering the curing temperature of RODA-Bis(MI-BZ) (RODA-Bis(MI-BZ) without BPA-Bis(FF-BZ) as a co-monomer is Formulation 6). The 3rd exothermal curing peak of Formulation 5, with maximum peak at 298° C., disappeared or shifted to lower temperature region, indicating that curing temperature of RODA-Bis(MI-BZ) could be significantly lowered in the presence of BPA-Bis(FF-BZ).

Figure 47:
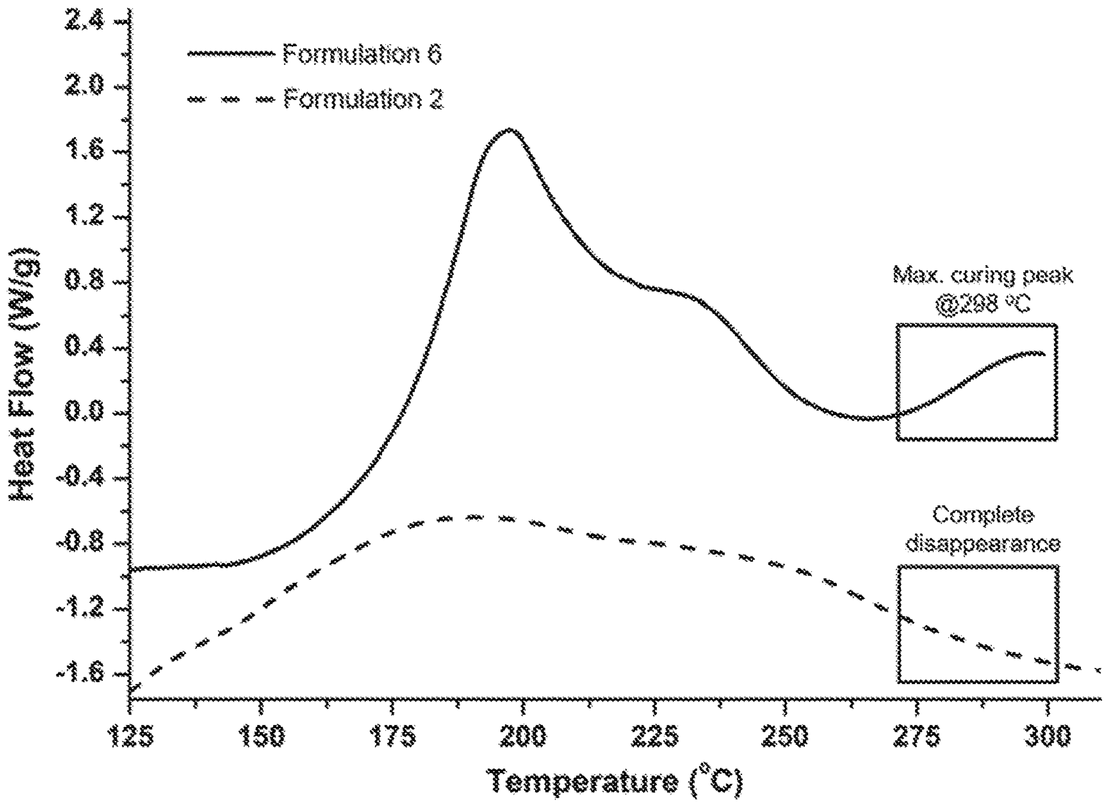
FIG. 47 shows DSC curves of Formulations 2 and 6, in accordance with one or more embodiments of the present disclosure.

Of Formulations 1-3, Formulation 2, containing equimolar ratio of BPA-Bis(FF-BZ) and RODA-Bis(MI-BZ), displayed the highest efficiency of decreasing the curing temperature of RODA-Bis(MI-BZ). As shown in FIG. 47, Formulation 2 displayed a mono-modal exothermal curing peak with maximum peak at 189° C., i.e., lowered by 109° C. as compared to Formulation 6. During this thermal curing of the curable compositions, two stages of curing reaction could occur simultaneously—i.e., ring-openings of benzoxazine moieties and the Diels-Alder [4+2] cycloaddition reaction of a benzoxazine and a maleimide functional group followed by the Michael addition-type reaction of a phenolic group of ring-opened benzoxazine moiety to an unsaturated α-positioned carbon of furan moiety. On the 2nd cycle of the DSC curve, the $T_g$ of Formulations 1, 2, and 3 was not apparent, which may be indicative of very high crosslinking density. Thus, it was concluded that curing temperature of RODA-Bis(MI-BZ) could be significantly lowered simply by blending it with BPA-Bis(F-BZ) and that the effect of BPA-Bis(F-BZ) on lowering the curing temperature could be maximized when the content ratio of furan moieties of BPA-Bis(F-BZ) and maleimide moieties of RODA-Bis(MI-BZ) are equivalent.

Figure 48:
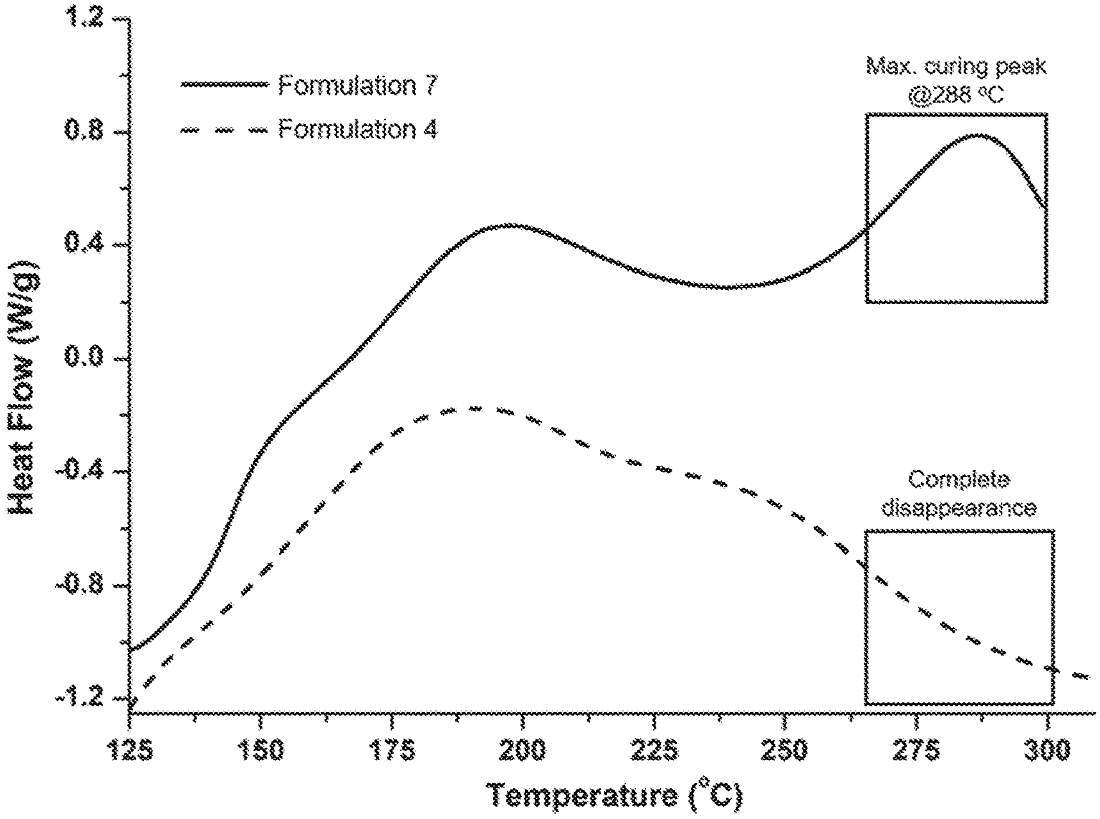
FIG. 48 shows DSC curves of Formulations 4 and 7, in accordance with one or more embodiments of the present disclosure.
Figure 49:
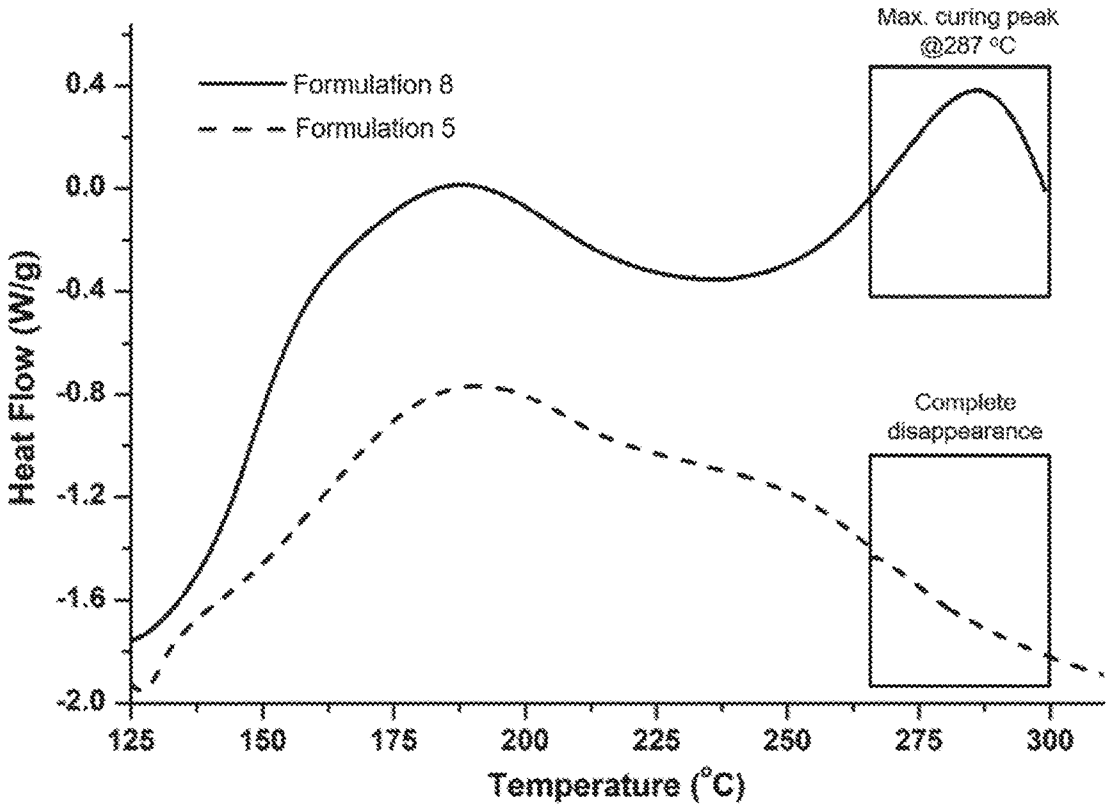
FIG. 49 shows DSC curves of Formulations 5 and 8, in accordance with one or more embodiments of the present disclosure.

Two additional formulations containing equimolar ratio of BAPP-Bis(MI-BZ) and BPA-Bis(F-BZ) (Formulation 4) or pTPEQ-Bis(MI-BZ) and BPA-Bis(F-BZ) (Formulation 5) were prepared and evaluated by DSC. As shown in FIGS. 48 and 49, similar to Formulation 2, the disappearance of an exothermal peak is observed for both formulations. BAPP-Bis(MI-BZ) has a maximum curing peak at 288° C., and pTPEQ-Bis(MI-BZ) has a maximum peak at 287° C. Neither of these peaks were obvious when BAPP-Bis(MI-BZ) or pTPEQ-Bis(MI-BZ) were mixed with BPA-Bis(F-BZ). Additionally, the $T_g$ of Formulations 4 and 5 were also not observed. Therefore, it was confirmed that the principle of lowering the curing temperature by blending with BPA-Bis (F-BZ) can be applied to a variety of maleimide functional group-containing benzoxazine resins.

Figure 50:
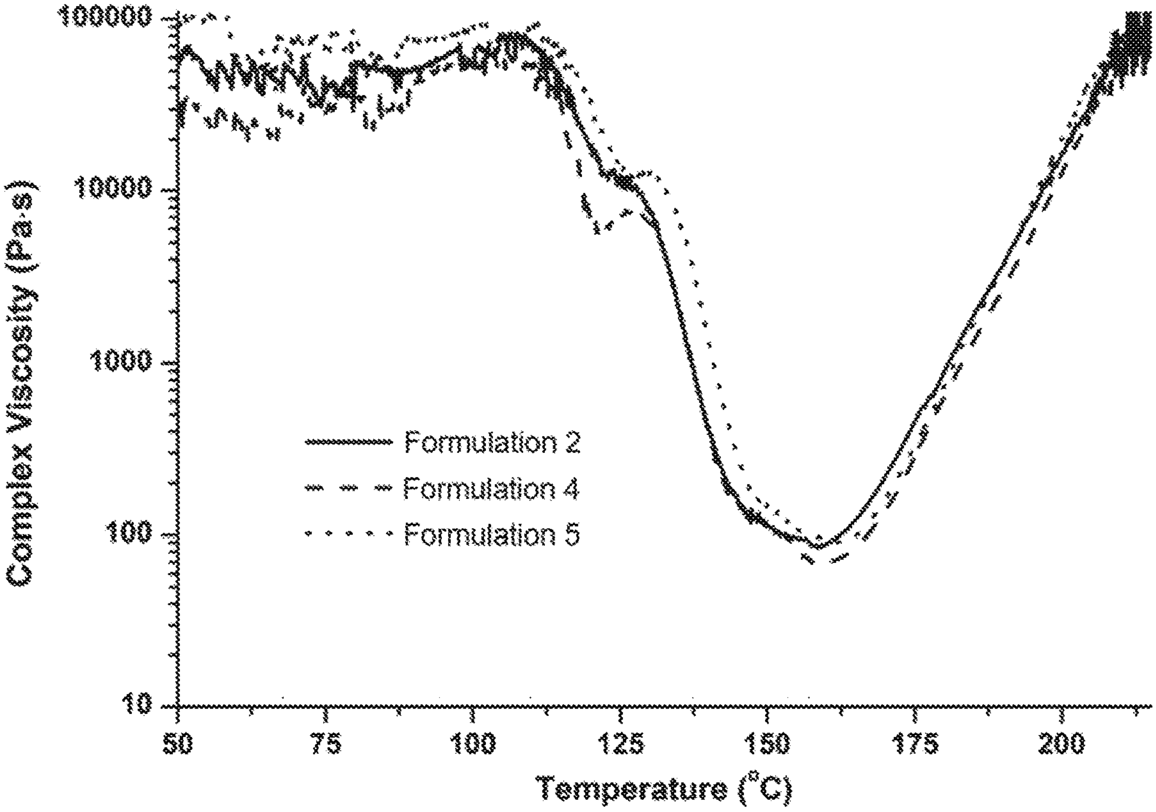
FIG. 50 shows the rheology behavior of Formulations 2, 4, and 5, in accordance with one or more embodiments of the present disclosure.
Figure 51A:
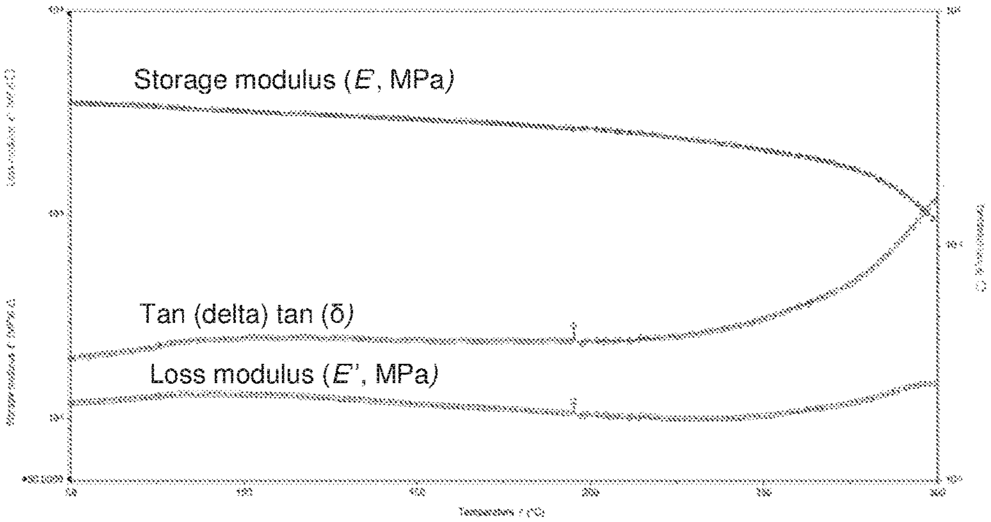
FIGS. 51A-C show graphs of storage modulus (MPa) and loss modulus (MPa) of Formulations 2, 4, and 5, respectively, in accordance with one or more embodiments of the present disclosure, as a function of temperature.
Figure 51B:
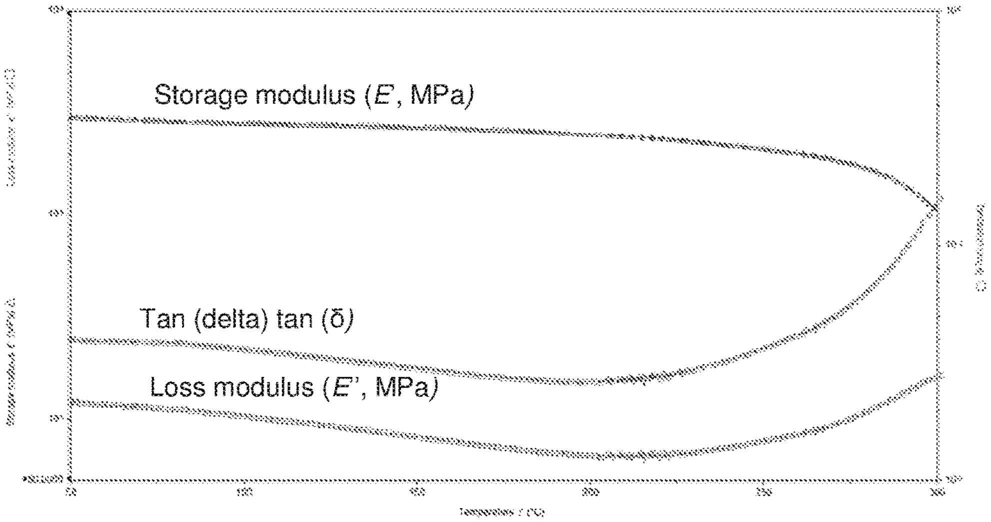
Figure 51C:
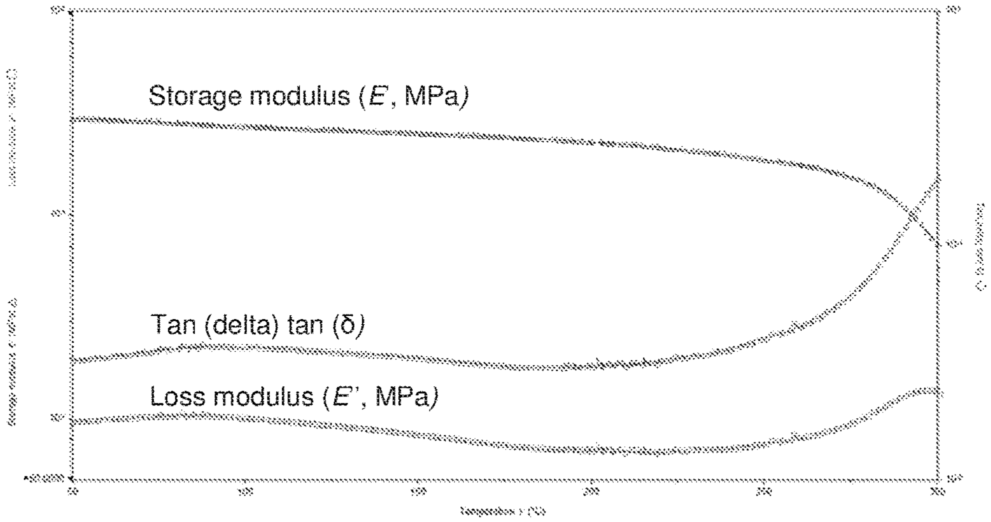
Figure 52A:
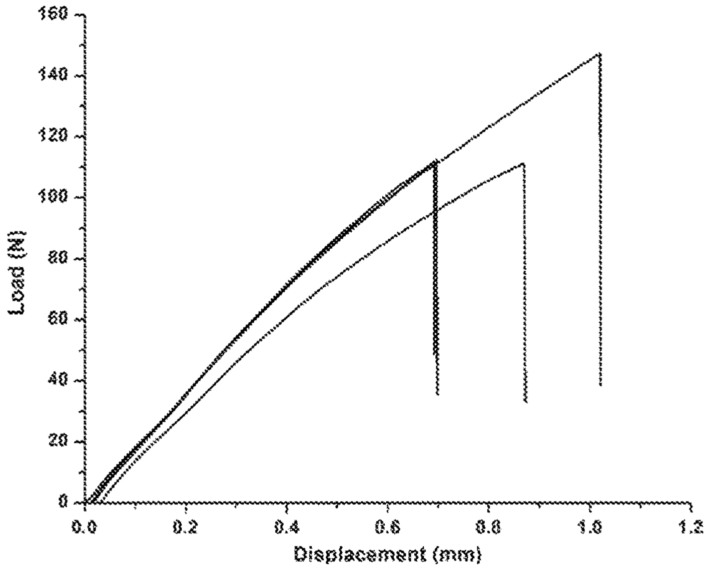
FIGS. 52A-C show stress-strain curves from tensile test of Formulations 2, 4, and 6, respectively, in accordance with one or more embodiments of the present disclosure.
Figure 52B:
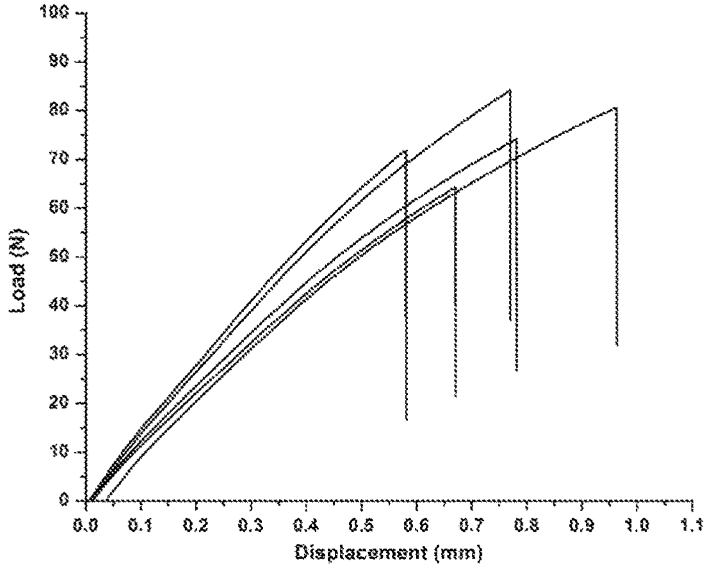
Figure 52C:
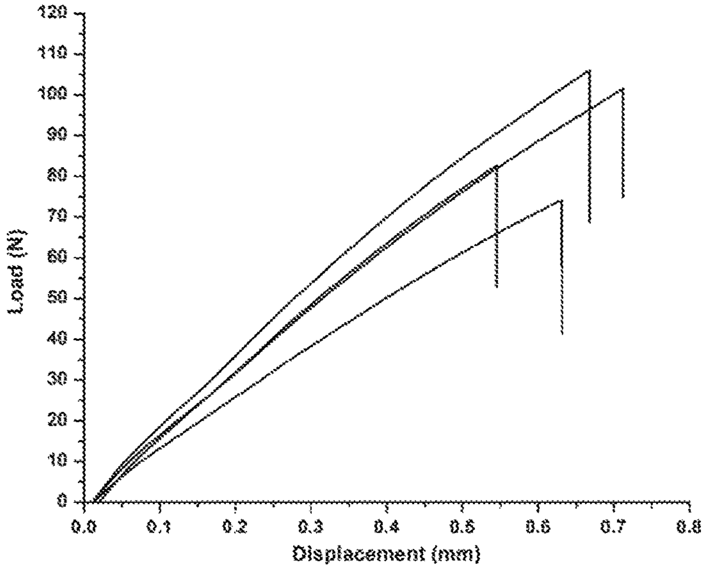

As shown in FIG. 50 and Table 7 Formulations 2, 4, and 5 also demonstrated very low complex viscosity, allowing for facile processing. For Formulation 2, a complex viscosity value of less than 100 Pa·s was observed in the temperature range of 152 to 162° C. with the minimum complex viscosity, 84 Pa·s, being at 159° C. The complex viscosity of Formulation 4 was less than 100 Pa·s in the temperature range of 152 to 167° C. with the minimum complex viscosity, 68 Pa·s, being at 158° C. For Formulation 5, a complex viscosity value of less than 100 Pa·s was observed in the temperature range of 157 to 165° C., with the minimum complex viscosity, 90 Pa·s, being at 162° C. Finally, it is noteworthy that relatively high complex viscosities of BAPP-Bis(MI-BZ) and pTPEQ-Bis(MI-BZ) alone could be lowered dramatically in the presence of BPA-Bis(F-BZ) (Formulations 4 and 5).

TABLE 8

Comparisons of Formulations 4 vs. 7 and Formulations 5 vs. 8 in Viscosity Profiles

| Property | | Formulation 4 | Formulation 7 (CE) | Formulation 5 | Formulation 8 (CE) |
|---|---|---|---|---|---|
| Viscosity profile (° C.) | @5000 Pa · s | 132-194 | 152-190 | 136-192 | 158-185 |
| | @100 Pa · s | 152-167 | N/A | 157-165 | N/A |
| | Minimum peak | 68 Pa · s @ 158° C. | 660 Pa · s @ 171° C. | 90 Pa · s @ 162° C. | 1757 Pa · s @173° C. |

Optimal curing temperatures for the curable compositions, as determined by DSC, were consecutive heating at 160° C. for 60 min, 180° C. for 50 min, 220° C. for 40 min, and 260 for 60 min.

As described above, Formulations 2, 4 and 5, without using any solvent, were molded into thin films of 150-300 μm in thickness by hot press using the molding conditions described above. DMA indicated $T_{g,onset}$ of the molded film of Formulations 2, 4, and 5 to be at 285, 288, and 285° C., respectively. According to the tensile test results, and as shown in FIGS. 51A-51C and 52A-52C, the cured product of Formulation 2 displayed 72±21 MPa of strength, 2.7±0.7 GPa of modulus, and 3.3±0.6% of elongation on average. The cured product of Formulation 4 displayed 61±11 MPa of strength, 2.7±0.5 GPa of modulus, and 3.0±0.6% of elongation on average. The cured product of Formulation 5 displayed 60±10 MPa of strength, 2.7±0.3 GPa of modulus, and 2.6±0.3% of elongation on average. Additionally, improved flexibility of the cured articles of the curable compositions is noted by way of folding the cured articles without resulting in breakage. This observation is also reflected in the elongation values.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed:

1. A benzoxazine resin composition, comprising:

a benzoxazine resin that is a reaction product of an amine, a phenol, and an aldehyde; and a second compound comprising at least one furan functional group and at least one benzoxazine group, wherein either the amine is a diamine or the phenol is a bisphenol, and wherein the benzoxazine resin has at least one nitrogen-containing crosslinking functional group selected from the group consisting of a maleimide functional group, a pyrocitric functional group, a nitrile functional group forming a triazine structure upon thermal activation, and combinations thereof.

2. The benzoxazine resin composition of claim 1, wherein the benzoxazine resin has the pyrocitric functional group selected from the group consisting of citraconic imide, itaconic imide, mesaconic imide, and combinations thereof.

3. The benzoxazine resin composition of claim 1, wherein the phenol is present in a molar ratio ranging from 1:1 to 2:1, relative to the diamine.

4. The benzoxazine resin composition of claim 1, wherein the second compound comprising the at least one furan functional group and the at least one benzoxazine group is included in the benzoxazine resin composition in an amount ranging between about 10% to about 90% by molar ratios (mol %), based on the total molar amount of the resin composition.

5. A method of forming a cured benzoxazine resin composition, comprising:

providing the benzoxazine resin composition of claim 1; and curing the benzoxazine resin by thermal activation to form the cured benzoxazine resin.

6. A composite material comprising reinforcement fibers and a curable matrix resin, wherein the curable matrix resin comprises the benzoxazine resin composition of claim 1.

7. The composite material of claim 6, wherein the composite material is a prepreg comprising a layer of reinforcement fibers impregnated with or embedded in the curable matrix resin.

8. The benzoxazine resin composition of claim 1, wherein the benzoxazine resin has the maleimide functional group selected from the group consisting of N-(2-hydroxyphenyl) maleimide, N-(3-hydroxyphenyl)maleimide, N-(4-hydroxyphenyl)maleimide, N-(4-carboxy-3-hydroxyphenyl)maleimide, N-(4-carboxy-2-hydroxyphenyl)maleimide, N-(3-carboxy-2-hydroxyphenyl)maleimide, N-(3-carboxy-4-hydroxyphenyl)maleimide, N-(2-carboxy-3-hydroxyphenyl)maleimide, and N-(2-carboxy-4-hydroxyphenyl)maleimide, and combinations thereof.

9. The benzoxazine resin composition of claim 1, wherein the benzoxazine resin has the nitrile functional group, the nitrile functional group being a cyano functional group.

10. A method of preparing a benzoxazine resin composition, comprising reacting an amine, a phenol, and an aldehyde to form a benzoxazine resin, wherein the benzoxazine resin has at least one nitrogen-containing crosslinking functional group selected from the group consisting of a maleimide functional group, a pyrocitric functional group, a nitrile functional group forming a triazine structure upon thermal activation, and combinations thereof, and wherein either the amine is a diamine or the phenol is a bisphenol, at a temperature of above 60° C., for 1 h to 5 days; and blending a second compound comprising at least one furan functional group and at least one benzoxazine group with the benzoxazine resin.

11. The method of claim 10, wherein the phenol is present in a molar ratio ranging from about 1:1 to about 2:1, relative to the diamine.

12. The method of claim 10, wherein prior to blending the second compound with the benzoxazine resin, the second compound is blended with a non-reactive diluent selected from the group consisting of 1,4-dioxane, benzene, toluene, chloroform, dimethyl sulfoxide, N-methylpyrrolidone, tetrahydrofuran, ethyl acetate, N,N-dimethylformamide, acetonitrile, propylene carbonate, N,N-dimethylacetamide, methanol, ethanol, isopropanol, nitromethane, and combinations thereof.

13. The method of claim 10, wherein the second compound comprising the at least one furan functional group and the at least one benzoxazine group is included in the benzoxazine resin composition in an amount ranging between 5% to 90% by molar ratios (mol %), based on the total molar amount of the resin composition.

14. A cured resin, comprising a cured benzoxazine resin, wherein the benzoxazine resin, prior to curing, comprises:

a reaction product of an amine, a phenol, and an aldehyde; and a second compound comprising at least one furan functional group and at least one benzoxazine group, wherein the benzoxazine resin has at least one nitrogen-containing crosslinking functional group selected from the group consisting of a maleimide functional group, a pyrocitric functional group, a nitrile functional group forming a triazine structure upon thermal activation, and combinations thereof, and wherein either the amine is a diamine or the phenol is a bisphenol.

15. The cured resin of claim 14, wherein the cured resin has a tensile strength, measured according to ASTM D1708, ranging from 30 to 150 MPa.

16. The cured resin of claim 14, wherein the cured resin has an elongation at break, measured according to ASTM D1708, ranging from 1 to 10%.

* * * * *